12) United States Patent
Laurent et al.

(10) Patent No.: US 10,562,893 B2
(45) Date of Patent: Feb. 18, 2020

(54) BENZIMIDAZOLES DERIVATIVES AS TEC KINASES FAMILY INHIBITORS

(71) Applicant: GB005, Inc., San Diego, CA (US)

(72) Inventors: Alain Laurent, Montreal (CA); Yannick Rose, Montreal (CA); Stephen J. Morris, Montreal (CA)

(73) Assignee: GB005, INC., San Diego, CA (US)

( * ) Notice: Subject to any disclaimer, the term of this patent is extended or adjusted under 35 U.S.C. 154(b) by 0 days.

(21) Appl. No.: 15/772,919

(22) PCT Filed: Sep. 22, 2016

(86) PCT No.: PCT/CA2016/051110
§ 371 (c)(1),
(2) Date: May 2, 2018

(87) PCT Pub. No.: WO2017/049401
PCT Pub. Date: Mar. 30, 2017

(65) Prior Publication Data
US 2018/0319781 A1 Nov. 8, 2018

(30) Foreign Application Priority Data
Sep. 25, 2015 (CA) ..................................... 2906137

(51) Int. Cl.
*C07D 409/12* (2006.01)
*A61P 37/00* (2006.01)
*A61P 31/12* (2006.01)
*A61P 29/00* (2006.01)
*A61P 35/00* (2006.01)
*A61K 47/02* (2006.01)
*A61K 47/16* (2006.01)
*C07D 235/32* (2006.01)
*C07D 409/14* (2006.01)

(52) U.S. Cl.
CPC ............ *C07D 409/12* (2013.01); *A61K 47/02* (2013.01); *A61K 47/16* (2013.01); *A61P 29/00* (2018.01); *A61P 31/12* (2018.01); *A61P 35/00* (2018.01); *A61P 37/00* (2018.01); *C07D 235/32* (2013.01); *C07D 409/14* (2013.01)

(58) Field of Classification Search
None
See application file for complete search history.

(56) References Cited

FOREIGN PATENT DOCUMENTS

| WO | WO 2013/184766 | * 12/2013 | ........... C07D 401/12 |
|---|---|---|---|
| WO | 2014/036016 A1 | 3/2014 | |
| WO | 2015/134210 A | 9/2015 | |

OTHER PUBLICATIONS

Bradshaw, "The Src, Syk, and Tec family kinases: Distinct types of molecular switches," *Cell Signalling* 22:1175-1184, 2010.

Carson et al., "IL-2 Inducible T-cell Kinase, a Novel Therapeutic Target in Melanoma," *Clin. Cancer Res.* 21(9):2167-2176, 2015. (22 pages).
Cenni et al., "BMX and Its Role in Inflammation, Cardiovascular Disease, and Cancer," *Int. Rev. Immunol.* 31(2):166-173, 2012. (9 pages).
Cho et al., "A Small Molecule Inhibitor of ITK and RLK Impairs Th1 Differentiation and Prevents Colitis Disease Progression," *J. Immunol.* 195:4822-4831, 2015.
Fan et al., "Role of Itk signalling in the interaction between influenza A virus and T-cells," *J. Gen. Virol.* 93:987-997, 2012.
Felices et al., "Tec Kinases in T Cell and Mast Cell Signaling," *Adv. Immunol.* 93:145-184, 2007.
Felices et al., "The Tec Kinases Itk and Rlk Regulate NKT Cell Maturation, Cytokine Production, and Survival," *J. Immunol.* 180:3007-3018, 2008. (13 pages).
Fowell et al., "Impaired NFATc Translocation and Failure of Th2 Development in Itk-Deficient CD4+ T cells," *Immunity* 11:399-409, 1999.
Gomez-Rodriguez et al., "Itk is required for Th9 differentiation via TCR-mediated induction of IL-2 and IRF4," *Nat. Commun.* 7:10857, 2016. (15 pages).
Gomez-Rodriguez et al., "Itk-mediated integration of T cell receptor and cytokine signaling regulates the balance between Th17 and regulatory T cells," *J. Exp. Med.* 211(3):529-543, 2014.
He et al., "Inhibition of IL-2 inducible T-cell kinase alleviates T-cell activation and murine myocardial inflammation associated with CVB3 infection," *Mol. Immunol.* 59:30-38, 2014.
Horwood et al., "Tec Family Kinases in Inflammation and Disease," *Int. Rev. Immunol.* 31(2):87-103, 2012. (18 pages).
Hu et al., "Identification of Rlk, a Novel Protein Tyrosine Kinase with Predominant Expression in the T Cell Lineage," *J. Biol. Chem.* 270(4):1928-1934, 1995.
International Search Report and Written Opinion, dated Dec. 1, 2016, for International Application No. PCT/CA2016/051110, 12 pages.
Kannan et al., "Requirement for Itk kinase activity for Th1, Th2, Th17 and iNKT cell cytokine production revealed by an allele sensitive mutant," *Eur. J. Immunol* 45(8):2276-2285, 2015. (19 pages).

(Continued)

*Primary Examiner* — Alicia L Otton
(74) *Attorney, Agent, or Firm* — Seed IP Law Group LLP

(57) ABSTRACT

The present invention relates to a novel family of covalent kinases inhibitors. Compounds of this class have been found to have inhibitory activity against members of the Tec kinase family, particularly ITK, BTK, BMX, Tec and/or RLK. The present invention is directed to a compound of Formula I or pharmaceutically acceptable salt, solvate, solvate of salt, stereoisomer, tautomer, isotope, prodrug, complex or biologically active metabolite thereof and its use in therapy.

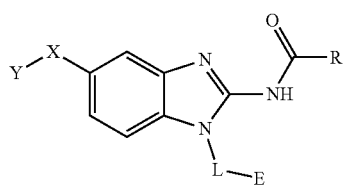

Formula I

10 Claims, No Drawings

(56) References Cited

OTHER PUBLICATIONS

Kanan et al., "Itk Signals Promote Neuroinflammation by Regulating CD4+T-Cell Activation and Trafficking," *J. Neurosci.* 35(1):221-233, 2015.

Lee et al., "The Association of a Single-Nucleotide Polymorphism of the IL-2 Inducible T-Cell Kinase Gene with Asthma," *Annals of Human Genetics* 75:359-369, 2011.

Lelais et al., "Discovery of (R,E)-N-(7-Chloro-1-(1-[4-(dimethylamino)but-2-enoyl]azepan-3-yl)-1H-benzo[d]imidazol-2-yl)-2-methylisonicotinamide (EGF816), a Novel, Potent, and WT Sparing Covalent Inhibitor of Oncogenic (L858R, exl9del) and Resistant (T790M) EGFR Mutants for the Treatment of EGFR Mutant Non-Small-Cell Lung Cancers," *J. Med. Chem.* 59(14):6671-6689, 2016.

Lin et al., "Selective Itk Inhibitors Block T-Cell Activation and Murine Lung Inflammation," *Biochemistry* 43:11056-11062, 2004.

Liu et al., "Reciprocal Regulation of C-Maf Tyrosine Phosphorylation by Tec and Ptpn22," *PLoS One* 10(5):e0127617, 2015. (16 pages).

Manning et al., "The Protein Kinase Complement of the Human Genome," *Science* 298:1912-1934, 2002. (8 pages).

Mano et al., "A novel protein-tyrosine kinase, tec, is preferentially expressed in liver," *Oncogene* 5:1781-1786, 1990.

Mueller et al., "Attenuation of Immunological Symptoms of Allergic Asthma in Mice Lacking the Tyrosine Kinase ITK," *J. Immunol.* 170:5056-5063, 2003. (9 pages).

Readinger et al., "Selective targeting of ITK blocks multiple steps of HIV replication," *Proc. Natl. Acad. Sci. USA* 105(18):6684-6689, 2008.

Sahu et al., "Selective expression rather than specific function of Txk and Itk regulate $T_H1$ and $T_H2$ responses," *J. Immunol.* 181(9):6125-6131, 2008. (15 pages).

Schaeffer et al., "Requirement for Tec Kinases Rlk and Itk in T cell Receptor Signaling and Immunity," *Science* 284:638-641, 1999. (5 pages).

Suzuki et al., "Skewed Th1 Responses Caused by Excessive Expression of Txk, a Member of the Tec Family of Tyrosine Kinases, in Patients with Behcet's Disease," *Clin. Med. Res.* 4(2):147-151, 2006.

Tomlinson et al., "Expression and Function of Tec, Itk, and Btk in Lymphocytes: Evidence for a Unique Role for Tec," *Mol. Cell Biol.* 24(6):2455-2466, 2004.

Von Bonin et al., "Inhibition of the IL-2-inducible tyrosine kinase (Itk) activity: a new concept for the therapy of inflammatory skin diseases," *Experimental Dermatology* 20:41-47, 2011.

Zwolanek et al., "The Non-receptor Tyrosine Kinase Tec Controls Assembly and Activity of the Noncanonical Caspase-8 Inflammasome," *PLOS Pathogens* 10(12):e1004525, 2014. (17 pages).

\* cited by examiner

BENZIMIDAZOLES DERIVATIVES AS TEC KINASES FAMILY INHIBITORS

CROSS REFERENCE TO RELATED APPLICATIONS

This application is a U.S. national phase pursuant to 35 U.S.C. § 371 of International Patent Application No. PCT/CA2016/051110, filed Sep. 22, 2016, which claims priority to Canadian Patent Application No. 2906137, filed Sep. 25, 2015, the disclosures of which are all herein incorporated by reference in their entireties.

FIELD OF INVENTION

The present invention relates to a novel family of protein kinase inhibitors, their pharmaceutically acceptable salts, to pharmacological compositions that contain them and to their use of the inhibitors to treat or prevent diseases, disorders and conditions associated with kinase function.

BACKGROUND OF THE INVENTION

Protein kinases are a large group of intracellular and transmembrane signalling proteins in eukaryotic cells (Manning G. et al, (2002) Science, 298: 1912-1934). Phosphorylation of specific amino acid residues in target proteins by protein kinases can modulate their activity leading to profound changes in cellular signalling and metabolism. Kinases play key roles in the regulation of cellular proliferation, survival, differentiation and function. Many kinases have been implicated in disease and, as such, are attractive therapeutic targets.

The Tec family of kinases consists of Tyrosine kinase expressed in hepatocellular carcinoma (TEC), Interleukin-2 inducible T-cell kinase (ITK, also known as TSK and EMT), Resting lymphocyte kinase (RLK, also known as TXK), Bruton's tyrosine kinase (BTK), Bone marrow kinase on the X-chromosome (BMX, also known as ETK) (Bradshaw J M Cell Signal. 2010; 22(8):1175-84). These intracellular kinases play important roles in the development and function of lymphocytes and myeloid cells (Horwood et al. Int Rev Immunol. 2012; 31(2):87-103, Felices M et al. Adv Immunol. 2007; 93:145-84). Additionally, selected Tec family members such as ITK, TEC and BMX are expressed in cancerous cells where they may play a role in cancer cell survival and malignancy (Carson C C et al. Clin Cancer Res. 2015; 21(9):2167-76, Mano H. et al. Oncogene. 1990; 5(12):1781-6, Cenni B et al. Int Rev Immunol. 2012; 31(2): 166-73).

ITK is an important component of T-cell signaling function and differentiation. ITK is activated upon stimulation of T-cell receptors and initiates a signaling cascade that results in cellular activation, cytokine release and rapid proliferation. ITK is important in T-helper (Th) cell development and function including Th1, Th2, Th9, Th17 and T-regulatory cell development (Fowell D J et al. 1999 Immunity 11:399-409; Gomez-Rodriguez J. et al. 2014 J. Exp Med 211:529-543, Gomez-Rodriguez J. et al 2016 Nat Commun. 2016; 7:10857). For example, ITK−/− CD4+ T-cells show significant reduction in the production of Th1 and Th17 cytokines and exhibit skewed T-effector/Treg-cell ratios with a bias towards FoxP3+ Treg (Kannan A et al 2015. J Neurosci. 35:221-233, Gomez-Rodriguez J. et al. 2014 J. Exp Med 211:529-543). Furthermore, specific inhibition of an allele-sensitive ITK mutant shows that ITK is important in Th1, Th2, Th17, and iNKT-cell cytokine production (Kannan A et al Eur. J. Immunol. 2015. 45: 2276-2285). Consequently, ITK is an important target for prevention or treatment of diseases involving Th cytokines, or where modulation of immunosuppressive Treg cells is desired. Furthermore, polymorphisms in the ITK promoter that increase ITK expression in humans have been linked to increased asthma incidence (Lee, S. H. et al. 2011 Ann Hum Genet 75:359-369) and ITK preferentially regulates the secretion of the Th2 cytokines IL-5 and IL-13 in models of allergic asthma suggesting that ITK inhibitors may be useful in the treatment of asthma (Muller C et al. 2003J Immunol. 170:5056-63). Also, ITK is upregulated in lesional skin from patients with allergic contact dermatitis, atopic dermatitis and psoriasis (von Bonin A et al. 2010. Exp. Derm; 20, 41-47).

RLK (TXK) is another Tec family member that is expressed in T-cells (Hu Q et al. 1995 J. Biol Chem. 270:1928-1934). TXK and ITK regulate Th cell-mediated responses via their differential expression in Th1 and Th2 cells, respectively (Sahu N et al. J. Immunol. 2008, 181: 6125-6131). Furthermore, while ITK−/− mice have impaired in NKT cell generation this defect is exacerbated in the absence of both RLK and ITK (Felices M. et al. 2008, J Immunol. 180:3007-3018). Increased expression of RLK has been reported in patients with Behcet's disease, an inflammatory disorder associated with increased inflammation and Th1 cytokine production (Suzuki N et al. 2006 Clin Med Res. 4:147-151). Knockout of both ITK and RLK produces stronger effects on T-cell function than knockout of either kinase alone (Schaeffer et al. 1999 Science 284:638-641; Felices et al. 2008 J. Immunol. 180:3007-3018).

TEC kinase, first shown to be expressed in hepatocellular carcinoma (Mano et al. 1990 Oncogene. 5:1781-6), is expressed in normal B and T-cells and is up-regulated upon T-cell activation in Th1 and Th2 cells (Tomlinson M G et al 2004 Mol. Cell. Biol., 24:2455-2466). TEC may have different roles from either ITK or RLK. TEC has a unique subcellular distribution differential protein interactions compared with ITK and RLK (Tomlinson M G et al 2004 Mol. Cell. Biol., 24:2455-2466) and TEC, but not RLK or LTK, is a tyrosine kinase of c-Maf leading to enhancement of c-Maf-dependent IL-4 promoter activity (Liu C C et al. 2015 PLoS One. 10:e0127617). Lastly, TEC controls assembly of the non-cannonical caspase 8 inflammasome involved in fungal sepsis and Tec-deficient mice are highly resistant to candidiasis (Zwolanek F et al. 2014 PLoS Pathog 10, e1004525).

Experimental data using Tec-kinase family null animals supports the therapeutic benefit of kinase inhibition in human disease. ITK modulates neuroinflammation due to experimental autoimmune encephalomyelitis (EAE), the animal model of multiple sclerosis (MS). ITK−/− mice exhibit reduced disease severity, and transfer of ITK−/− CD4+ T-cells into T-cell-deficient mice results in lower EAE disease severity (Kannan Ak et al. J. Neurosci, 2015; 35:221-233). ITK−/− mice exhibit decreased inflammatory response in contact hypersensitivity models (Von Bonin et al. Experimental Dermatology, 2010; 20, 41-47) and secretion of the Th2 cytokines IL-5 and IL-13 is decreased in models of allergic asthma in ITK−/− mice (Mueller C et al. J Immunol. 2003; 170(10):5056-63).

Data obtained with inhibitors of select Tec family kinases suggests that inhibitors of these kinases may be useful in the treatment of disease. Inhibitors of ITK, RLK and other Tec family members may be useful in the prevention or treatment of T-cell related diseases such as multiple sclerosis, asthma, atopic dermatitis, psoriasis and inflammatory bowel diseases as well as viral infections. For example, a small molecule inhibitor of ITK and RLK has shown efficacy in the mouse adoptive T-cell transfer model of colitis (Cho H-S et al. 2015; J. Immunol. 195: 4822-31).

Also, a selective ITK inhibitor blocked leukocyte lung infiltration following ovalbumin challenge in a rat model of asthma (Lin T A et al. 2004 Biochemistry. 43:11056-11062). Additionally, an ITK inhibitor was effective in mouse models of skin contact hypersensitivity (von Bonin A et al. 2010. Exp. Derm; 20, 41-47). Furthermore, ITK inhibitors can alter the HIV replication at various stages of viral life cycle including viral entry, gp120-induced actin reorganization, transcription from viral long terminal repeats (LTR) and virion assembly release from T-cells (Readinger J A et al. Proc Natl Acad Sci USA. 2008; 105(18):6684-9). Similarly ITK inhibition alleviates T-cell activation and murine myocardial inflammation associated with Coxsackie virus CVB3 infection (He F et al. Mol Immunol. 2014; 59(1):30-8) and ITK is required for efficient replication of influenza virus in infected T-cells (Fan K et al. J Gen Virol. 2012; 93(Pt 5):987-97). These data suggest that inhibitors of the Tec family kinases may be useful in the treatment of a variety of human and animal diseases.

SUMMARY OF THE INVENTION

The present invention relates to a novel family of covalent kinase inhibitors. Compounds of this class have been found to have inhibitory activity against members of the Tec kinase family, particularly ITK, BTK, BMX and/or RLK (TXK) and/or TEC.

One aspect of the present invention is directed to a compound of Formula I:

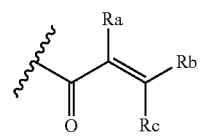

Formula I or pharmaceutically acceptable salt, solvate, solvate of salt, stereoisomer, tautomer, isotope, prodrug, complex or biologically active metabolite thereof, wherein R is selected from substituted or unsubstituted aryl, or substituted or unsubstituted heteroaryl;

L is independently selected from

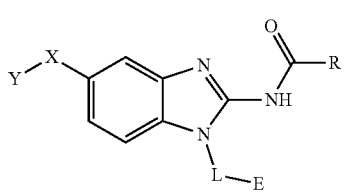

where the ring $B_1$ is selected from substituted or unsubstituted cycloalkyl, substituted or unsubstituted heterocyclyl, substituted or unsubstituted aryl, or substituted or unsubstituted heteroaryl;

or

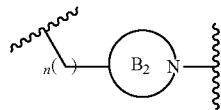

where the ring $B_2$ is selected from substituted or unsubstituted polycyclic ring system;

$R^1$ is selected from hydrogen, lower alkyl or lower cycloalkyl;

n is an integer from 0 to 1;

E is:

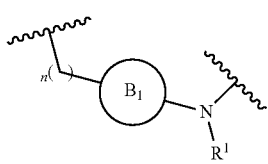

wherein:

Ra, Rb and Rc are independently selected from hydrogen, halogen, —CN, substituted or unsubstituted alkyl, substituted or unsubstituted heteroalkyl, substituted or unsubstituted cycloalkyl, and substituted or unsubstituted heterocyclyl; or Ra and Rb taken together with the carbon atoms to which they are attached form a 3- to 8-membered substituted or unsubstituted cycloalkyl ring, or form a 3- to 8-membered substituted or unsubstituted heterocyclyl ring, and Rc is selected as above; or Rb and Rc taken together with the carbon atom to which they are attached form a 3- to 8-membered substituted or unsubstituted cycloalkyl ring, or form a 3- to 8-membered substituted or unsubstituted heterocyclyl ring, and Ra is selected as above; or Ra and Rb taken together with the carbon atoms to which they are attached form a triple bond and Rc is selected as above;

provided L-E is selected from

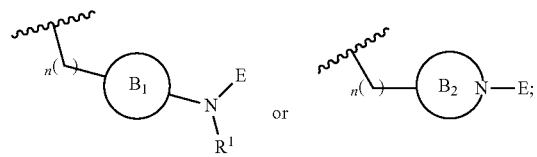

X is either:

1) selected from alkylene, -(alkylene)-NR²—, -(alkylene)-NR³—, -(alkylene)-O—, —O—, —S—, —S(O)$_m$—, —NR²—, —NR³—, —C(O)—, —C(O)O—, —C(O)NR²—, —C(O)ONR²—, or —S(O)$_m$NR²—;

$R^2$ is selected from hydrogen, lower alkyl or lower cycloalkyl;

$R^3$ is selected from —C(O)R⁴, —C(O)OR⁴ or —S(O)$_m$R⁴;

R⁴ is selected from lower alkyl or lower cycloalkyl; and
m is an integer selected from 1 to 2; or
2) X is a bond; and
Y is selected from hydrogen, halogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocyclyl, substituted or unsubstituted aryl, substituted or unsubstituted heteroaryl, substituted or unsubstituted aralkyl, or substituted or unsubstituted heteroaralkyl.

In another aspect provided herein a pharmaceutical composition comprising a compound disclosed herein of Formula I, and/or a pharmaceutically acceptable salt, solvate, solvate of salt, stereoisomer, tautomer, isotope, prodrug, complex or biologically active metabolite thereof; and one or more pharmaceutically acceptable excipients.

The pharmaceutical composition of the present invention comprising a compound of Formula I, and/or a pharmaceutically acceptable salt, solvate, solvate of salt, stereoisomer, tautomer, isotope, prodrug, complex or biologically active metabolite thereof suitable for use in therapy, wherein a subject is suffering of a disease, disorder or condition in which one or more TEC kinase family member activity is implicated and can be treated by kinase inhibition.

In another aspect, the present invention relates to the use of a compound of Formula I as defined herein, or a pharmaceutically acceptable salt or solvate thereof, in the manufacture of a medicament for use in subjects for the treatment or prevention of protein kinase mediated diseases or conditions, for the treatment of cancer, autoimmune diseases, allergic diseases, inflammatory diseases, graft-versus-host disease, thromboembolic diseases, neurological disorders, viral infections, bone-related diseases or combinations thereof.

Another aspect of the present invention provides the synthetic methods used to prepare compounds of Formula I of the present invention and are not intended to be limiting.

In yet another aspect, provided herein a method of preventing or treating a disease treatable by inhibition of ITK in a patient which comprises administering to the patient a pharmaceutical composition comprising a compound of Formula I and/or a pharmaceutically acceptable salt, solvate, solvate of salt, stereoisomer, tautomer, isotope, prodrug, complex or biologically active metabolite thereof disclosed herein in a therapeutically effective amount and one or more pharmaceutically acceptable excipients. In a particular embodiment, the disease or conditions include allergic diseases, autoimmune diseases, inflammatory diseases, thromboembolic diseases, bone-related diseases, cancer, graft-versus-host disease, and thereof.

In one embodiment of this aspect the patient suffers from a disease or disorder that can be treated by kinase inhibition. The compound disclosed herein and/or pharmaceutically acceptable salt thereof can inhibit one or more kinases including but not limited to ITK, RLK (also known as TXK), BLK, BMX, BTK, JAK3, and/or TEC.

In another aspect the present invention provides a pharmaceutical combination comprising a compound of Formula I, Formula IIa, Formula IIb, Formula IIc of the present invention or a pharmaceutically acceptable salt, solvate, solvate of salt, stereoisomer, tautomer, isotope, prodrug, complex or biologically active metabolite thereof and at least one additional active pharmaceutical ingredient for the treatment or prevention of cancer, autoimmune diseases, allergic diseases, inflammatory diseases or viral infection in combination therapy.

In one embodiment the present invention provides a method of treatment wherein further comprising administering of a therapeutically effective amount of at least one additional active pharmaceutical ingredient for the treatment of cancer, autoimmune diseases, allergic diseases, inflammatory diseases, neurological disorders or viral infection in combination therapy. The additional active pharmaceutical ingredient is administered together with the compounds of Formula I, Formula IIa, Formula IIb, Formula IIc, or a pharmaceutically acceptable salt, solvate, solvate of salt, stereoisomer, tautomer, isotope, prodrug, complex or biologically active metabolite thereof as a single dosage form or separately as part of a multiple dosage form. The additional active pharmaceutical ingredient is selected from the group comprising: steroids, leukotriene antagonists, anti-histamines, anti-cancer, anti-viral, anti-biotic agents, protein kinase inhibitors or combinations thereof.

The administration of a compound of the present invention may be by any appropriate means known in the field, including systemic and localized administration. Prior to administration, the compounds may be formulated as compositions suitable for pharmaceutical or clinical use. Such compositions may comprise appropriate carriers or excipients, such as those for topical, inhalation, or systemic administration. The compound of the present invention may be administered alone or in combination with one or more pharmaceutically acceptable active for the treatment or prevention of a protein kinase mediated condition.

All publications, patent applications, patents and other references mentioned herein are incorporated by reference in their entirety.

Other features, objects, and advantages of the invention(s) disclosed herein will be apparent from the description and drawings, and from the claims.

DETAILED DESCRIPTION OF THE INVENTION

The present invention is directed to a compound of Formula I:

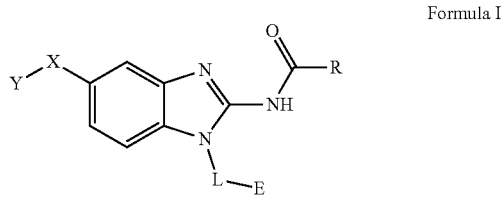

Formula I or pharmaceutically acceptable salt, solvate, solvate of salt, stereoisomer, tautomer, isotope, prodrug, complex or biologically active metabolite thereof, wherein
R is selected from substituted or unsubstituted aryl, or substituted or unsubstituted heteroaryl;
L is independently selected from

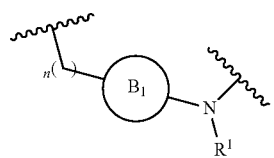

where the ring $B_1$ is selected from substituted or unsubstituted cycloalkyl, substituted or unsubstituted heterocyclyl, substituted or unsubstituted aryl, or substituted or unsubstituted heteroaryl;

or

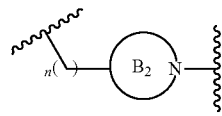

where the ring $B_2$ is selected from substituted or unsubstituted polycyclic ring system;

$R^1$ is selected from hydrogen, lower alkyl or lower cycloalkyl;

n is an integer from 0 to 1;

E is:

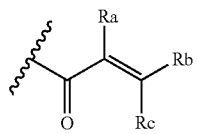

wherein:

Ra, Rb and Rc are independently selected from hydrogen, halogen, —CN, substituted or unsubstituted alkyl, substituted or unsubstituted heteroalkyl, substituted or unsubstituted cycloalkyl, and substituted or unsubstituted heterocyclyl; or Ra and Rb taken together with the carbon atoms to which they are attached form a 3- to 8-membered substituted or unsubstituted cycloalkyl ring, or form a 3- to 8-membered substituted or unsubstituted heterocyclyl ring, and Rc is selected as above; or Rb and Rc taken together with the carbon atom to which they are attached form a 3- to 8-membered substituted or unsubstituted cycloalkyl ring, or form a 3- to 8-membered substituted or unsubstituted heterocyclyl ring, and Ra is selected as above; or Ra and Rb taken together with the carbon atoms to which they are attached form a triple bond and Rc is selected as above;

wherein L-E is selected from

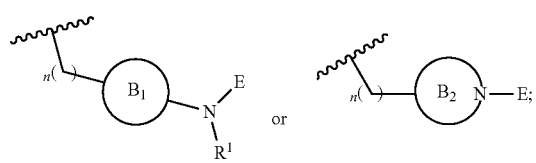

X is either:

1) selected from alkylene, -(alkylene)-NR$^2$—, -(alkylene)-NR$^3$—, -(alkylene)-O—, —O—, —S—, —S(O)$_m$—, —NR$^2$—, —NR$^3$—, —C(O)—, —C(O)O—, —C(O)NR$^2$—, —C(O)ONR$^2$—, or —S(O)$_m$NR$^2$—;

$R^2$ is selected from hydrogen, lower alkyl or lower cycloalkyl;

$R^3$ is selected from —C(O)R$^4$, —C(O)OR$^4$ or —S(O)$_m$R$^4$;

$R^4$ is selected from lower alkyl or lower cycloalkyl; and m is an integer selected from 1 to 2; or 2) X is a bond, and Y is selected from hydrogen, halogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocyclyl, substituted or unsubstituted aryl, substituted or unsubstituted heteroaryl, substituted or unsubstituted aralkyl, or substituted or unsubstituted heteroaralkyl.

An embodiment of the present invention relates to a novel covalent kinase inhibitors of Formula I Formula I

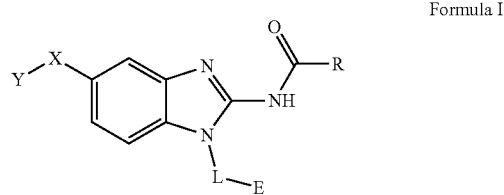

Wherein R is selected from substituted or unsubstituted 5- and 6-membered aryl ring or substituted or unsubstituted 5- and 6-membered heteroaryl ring;

L is independently selected from

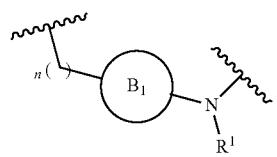

Wherein ring $B_1$ is selected from substituted or unsubstituted 3- to 8-membered cycloalkyl ring, substituted or unsubstituted 3- to 8-membered heterocyclyl ring, substituted or unsubstituted 5- and 6-membered aryl ring, substituted or unsubstituted 5- and 6-membered heteroaryl ring;

or

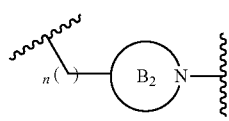

wherein ring $B_2$ is selected from substituted or unsubstituted 9- to 12-membered polycyclic ring system;

$R^1$ is selected from hydrogen, $C_{1-6}$ alkyl or 3- to 8-membered cycloalkyl ring;

n is an integer selected from 0 or 1;

E is selected from the group:

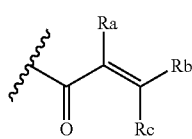

wherein Ra, Rb and Rc are independently selected from hydrogen, halogen, —CN, substituted or unsubstituted $C_{1-4}$ alkyl chain, substituted or unsubstituted heteroalkyl chain of 2 to 6 atoms, substituted or unsubstituted 3- to 8-membered cycloalkyl ring, or substituted or unsubstituted 3- to 8-membered heterocyclyl ring; or Ra and Rb taken together with the carbon atoms to which they are attached form a 3- to 8-membered substituted or unsubstituted cycloalkyl ring or form a 3- to 8-membered substituted or unsubstituted heterocyclyl ring and Rc is selected as above; or Rb and Rc taken together with the carbon atom to which they are attached form a 3- to 8-membered substituted or unsubstituted cycloalkyl ring, or form a 3- to 8-membered substituted or unsubstituted heterocyclyl ring, and Ra is selected as above; or Ra and Rb taken together with the carbon atoms to which they are attached form a triple bond and Rc is selected as above;

wherein L-E is selected from

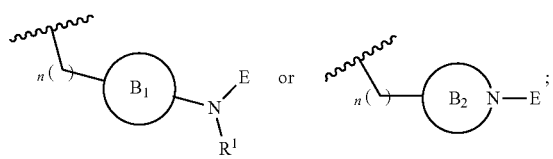

X is selected from $C_{1-6}$ alkylene, —($C_{1-6}$alkylene)-$NR^2$—, —($C_{1-6}$ alkylene)-$NR^3$—, —($C_{1-6}$ alkylene)-O—, —O—, —S—, —S(O)$_m$—, —$NR^2$—, —$NR^3$—, —C(O)—, —C(O)O—, —C(O)$NR^2$—, —C(O)O$NR^2$—, and —S(O)$_m NR^2$—;

wherein
$R^2$ is selected from hydrogen, $C_{1-6}$alkyl or 3- to 8-membered cycloalkyl ring;
$R^3$ is selected from —C(O)$R^4$, —C(O)O$R^4$ and —S(O)$_m R^4$;
$R^4$ is selected from $C_{1-6}$alkyl or 3- to 8-membered cycloalkyl ring;
m is an integer selected from 1 to 2; or
X is a bond, and;

Y is selected from the group consisting of hydrogen, halogen, substituted or unsubstituted $C_{1-6}$ alkyl chain, substituted or unsubstituted $C_{2-6}$ alkenyl chain, substituted or unsubstituted $C_{2-6}$ alkynyl chain, substituted or unsubstituted heteroalkyl chain of 2 to 6 atoms, substituted or unsubstituted 3- to 8-membered cycloalkyl ring, substituted or unsubstituted 3- to 8-membered heterocyclyl ring, substituted or unsubstituted 5-, and 6-membered aryl ring, substituted or unsubstituted 5-, and 6-membered heteroaryl ring, substituted or unsubstituted aralkyl, or substituted or unsubstituted heteroaralkyl.

An embodiment includes compounds of Formula I, wherein Ra, Rb and Rc are independently selected from the group consisting of hydrogen, —CN, halogen, $C_{1-3}$ substituted or unsubstituted alkyl chain, or substituted or unsubstituted heteroalkyl chain of 2 to 3 atoms.

An embodiment includes compounds of Formula I, wherein n is =0.

An embodiment includes compounds of Formula I, wherein n is =1.

An embodiment includes compounds of Formula I, wherein ring $B_1$ is a 3- to 8-membered substituted or unsubstituted cycloalkyl ring, or a 3- to 8-membered substituted or unsubstituted heterocyclic ring.

An embodiment includes compounds of Formula I, wherein ring $B_1$ is a substituted or unsubstituted aryl ring, or a substituted or unsubstituted heteroaryl ring, for example a substituted or unsubstituted phenyl ring or a substituted or unsubstituted 5 to 6 membered heteroaryl ring.

An embodiment includes compounds of Formula I, wherein ring $B_1$ is a substituted or unsubstituted 5-, and 6-membered aryl ring, or a substituted or unsubstituted 5-, and 6-membered heteroaryl ring.

An embodiment includes compounds of Formula I, wherein ring $B_1$ is a substituted or unsubstituted 6-membered aryl ring, for example a substituted or unsubstituted phenyl ring.

An embodiment includes compounds of Formula I, wherein ring $B_1$ is a substituted or unsubstituted cycloalkyl ring.

In an embodiment of the present invention $B_1$ is selected from substituted or unsubstituted: cyclobutyl, cyclopentyl or cyclohexyl and n is 0.

In an alternate embodiment, $B_1$ is selected from substituted or unsubstituted phenyl, and n is 0.

An embodiment includes compounds of Formula I where $R^1$ is hydrogen or methyl.

An embodiment includes compounds of Formula I, wherein $R^1$ is hydrogen.

An embodiment includes compounds of Formula I, wherein $R^1$ is methyl.

An embodiment includes compounds of Formula I, wherein $B_2$ is a substituted or unsubstituted polycyclic ring system, for example a 9- or 10-membered polycyclic ring system.

In an embodiment of the present invention $B_2$ is:

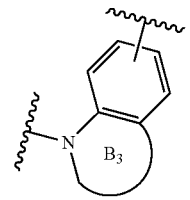

wherein $B_3$ is a 3- to 8-membered substituted or unsubstituted heterocyclyl ring.

$B_3$ may also be a 5- or 6-membered substituted or unsubstituted heterocyclyl ring. Optionally, $B_3$ is pyrolidine, morpholine, piperidine, or piperazine.

Preferably $B_3$ is pyrolidine or morpholine. Accordingly, $B_2$ may be:

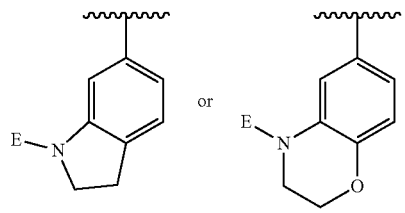

An embodiment includes compounds of Formula I, wherein n is =0.

An embodiment includes compounds of Formula I, wherein n is =1.

An embodiment includes compounds of Formula I, wherein R is a substituted or unsubstituted 6-membered aryl ring, for example a substituted or unsubstituted phenyl ring.

An embodiment includes compounds of Formula I, wherein R is a substituted or unsubstituted 5- or 6-heteroaryl ring.

An embodiment includes compounds of Formula I, wherein R is a substituted or unsubstituted 5-membered heteroaryl ring.

An embodiment includes compounds of Formula I, wherein R is a substituted or unsubstituted 6-membered heteroaryl ring.

An embodiment includes compounds of formula I where X—Y is selected from —CH$_2$—NH—Y, —CH$_2$—NR$^2$—Y, —C(O)—NR$^2$—Y, —NR$^2$C(O)—Y, —NR$^2$SO$_2$—Y, —O—CH$_2$—Y, —CH—NR$^3$—Y, —CH$_2$—Y wherein Y is as defined herein.

An embodiment includes compounds of Formula I, where X—Y is selected from —CH$_2$—NH—Y, and wherein Y is as defined herein.

An embodiment includes compounds of Formula I, where X—Y is selected from —CH$_2$—NR$^2$—Y, and wherein R$^2$ and Y are as defined herein.

An embodiment includes compounds of Formula I, where X—Y is selected from —C(O)—NR$^2$—Y, and wherein R$^2$ and Y are as defined herein.

An embodiment includes compounds of Formula I, where X—Y is selected from —NR$^2$C(O)—Y, and wherein R$^2$ and Y are as defined herein.

An embodiment includes compounds of Formula I, where X—Y is selected from —NR$^2$SO$_2$—Y, and wherein R$^2$ and Y are as defined herein.

An embodiment includes compounds of Formula I, where X—Y is selected from —O—CH$_2$—Y, and wherein Y is as defined herein.

An embodiment includes compounds of Formula I, where X—Y is selected from —CH$_2$—NR$^3$—Y, and wherein R$^3$ and Y are as defined herein.

An embodiment includes compounds of Formula I, where X—Y is selected from —CH$_2$—Y, and wherein Y is as defined herein.

In an embodiment of the present invention B$_1$ is selected from substituted or unsubstituted: cyclobutyl, cyclopentyl, cyclohexyl or phenyl.

In an alterate embodiment, B$_1$ is selected from substituted or unsubstituted: cyclobutyl, cyclopentyl, cyclohexyl or phenyl, and n is 0.

More preferred embodiment includes compounds of Formula I where, wherein L-E is selected from the group consisting of:

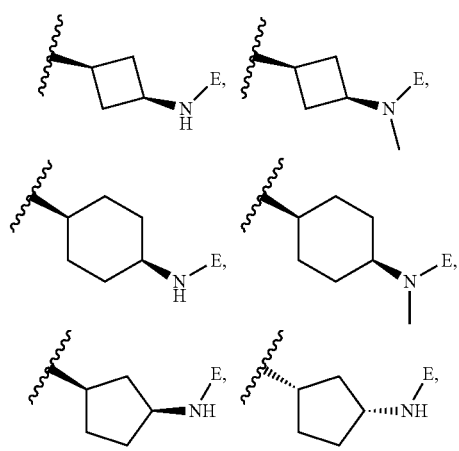

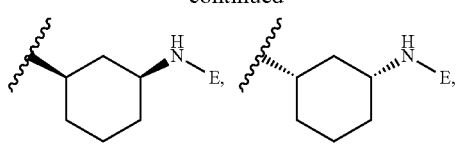

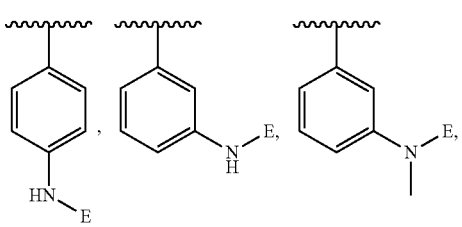

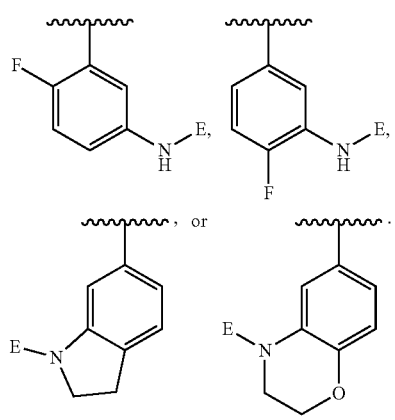

An embodiment includes compounds of Formula I where L-E is selected from the group consisting of:

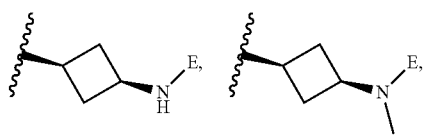

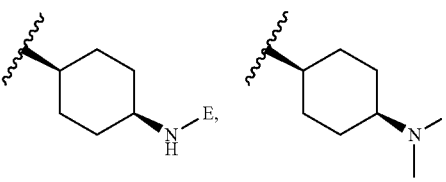

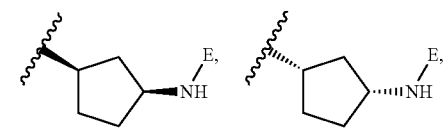

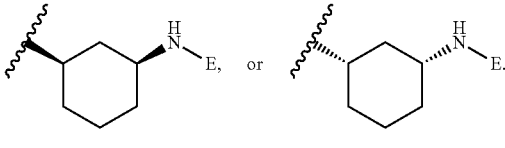

An alternate embodiment includes compounds of Formula I, wherein L-E is selected from:

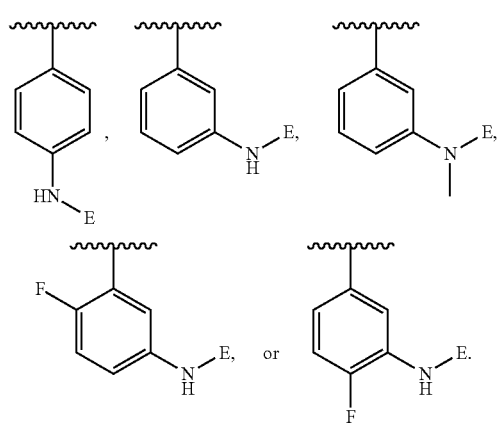

An embodiment of the present invention includes compounds of Formula I where L-E is selected from:

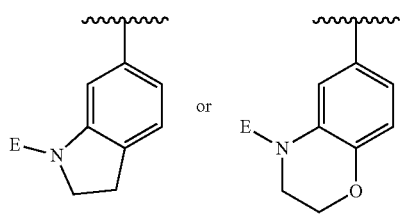

An embodiment of the present invention also includes compounds of Formula I wherein E is selected from:

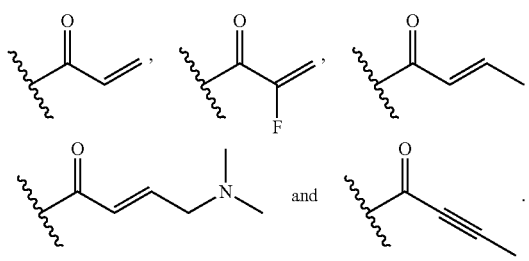

An embodiment of the present invention includes compounds of Formula I, where E is

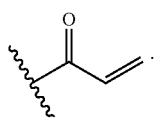 [SMILES: *C(=O)C=C]

An alternate embodiment includes compounds of Formula I, where X—Y is selected from:

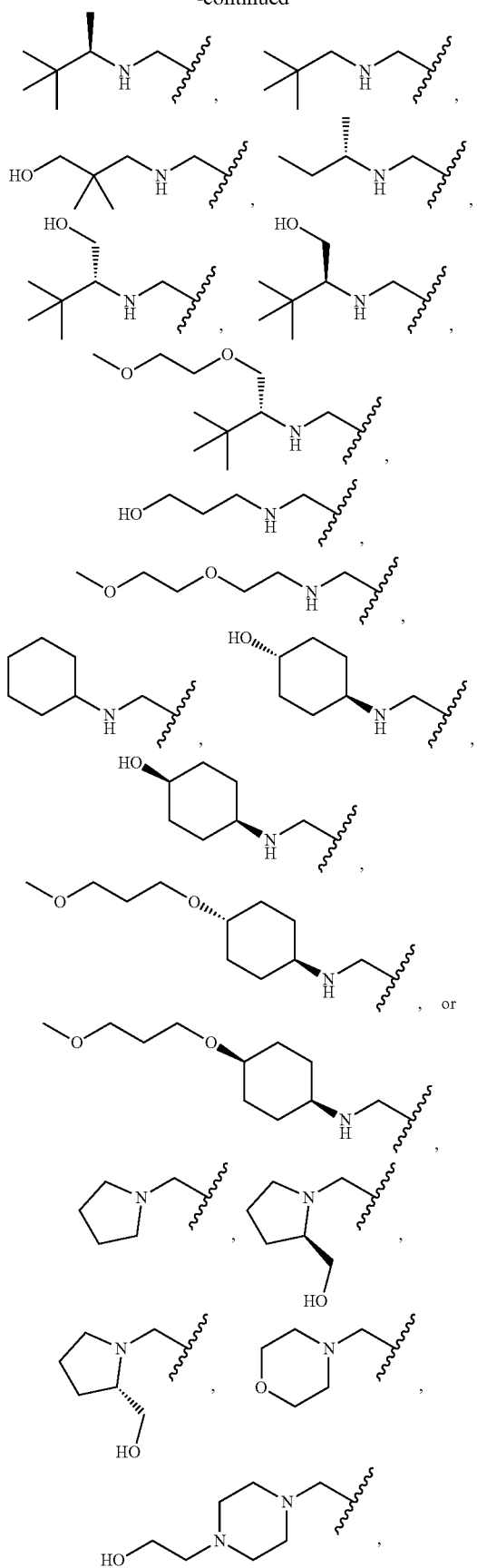

-continued

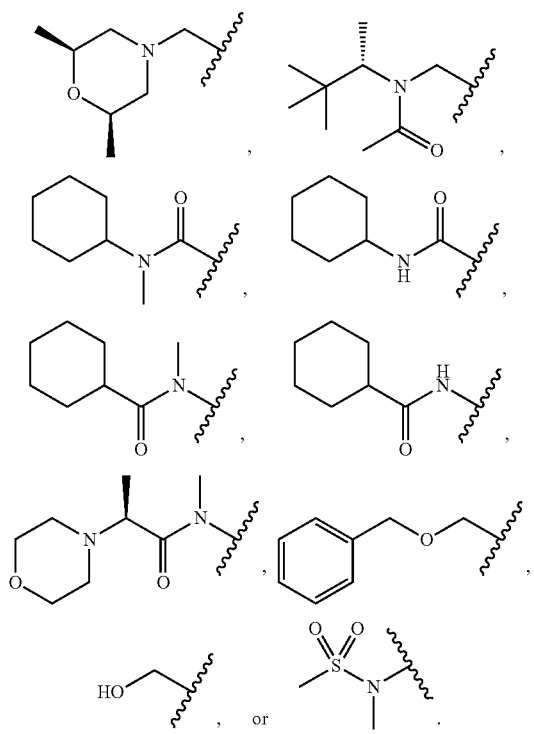

An embodiment of the present invention includes compounds of Formula I, where X—Y is selected from:

-continued

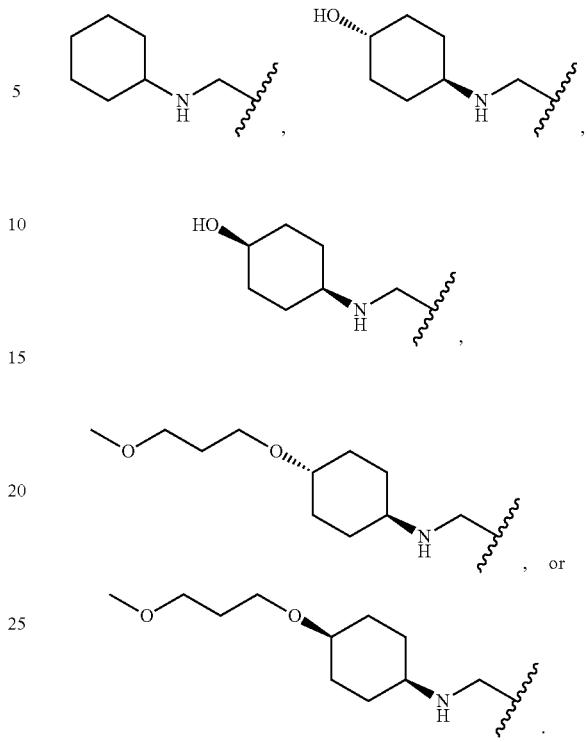

An embodiment of the present invention includes compounds of Formula I, where X—Y is selected from:

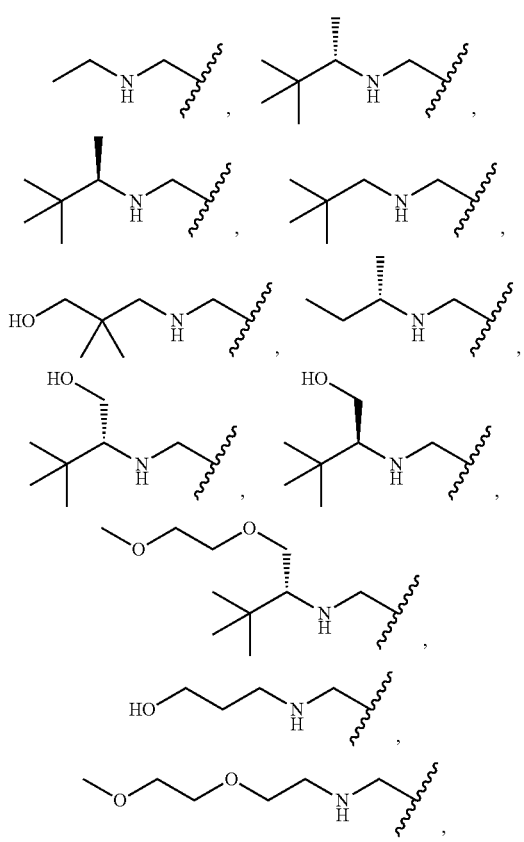

An embodiment of the present invention includes compounds of Formula I, wherein X—Y is

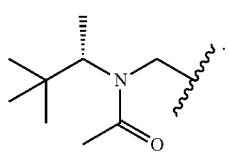 [SMILES: *CN(C(C)=O)[C@@H](C)C(C)(C)C]

An embodiment of the present invention includes compounds of Formula I, wherein X—Y is selected from:

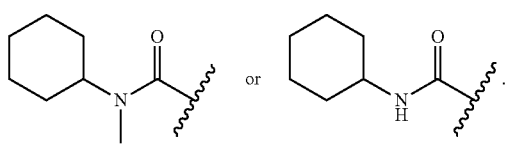 [SMILES: *C(=O)N(C)C1CCCCC1 ; *C(=O)NC1CCCCC1] or

An embodiment of the present invention compounds of Formula I, wherein X—Y is selected from:

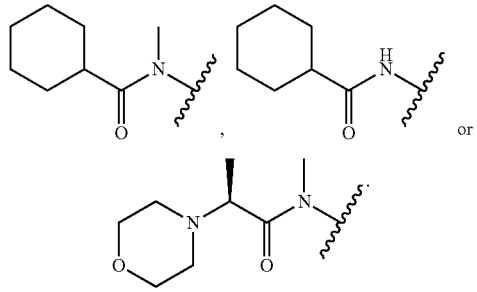

An embodiment of the present invention includes compounds of Formula I, wherein X—Y is selected from:

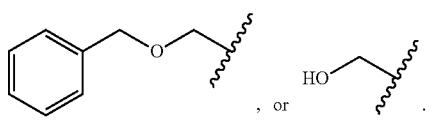

An embodiment of the present invention includes compounds of Formula I, wherein X—Y is

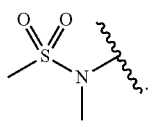 [SMILES: *N(C)S(C)(=O)=O]

An embodiment of the present invention includes compounds of Formula I where, wherein R is selected from the group consisting of:

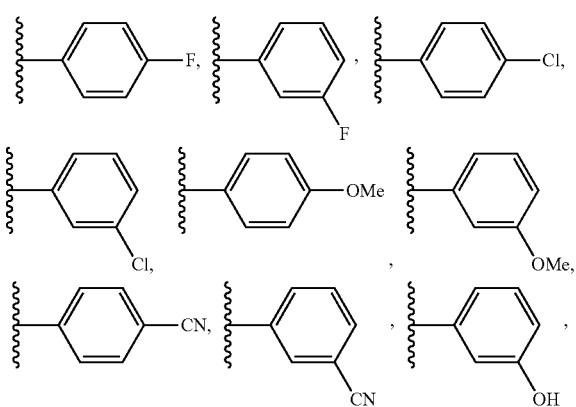

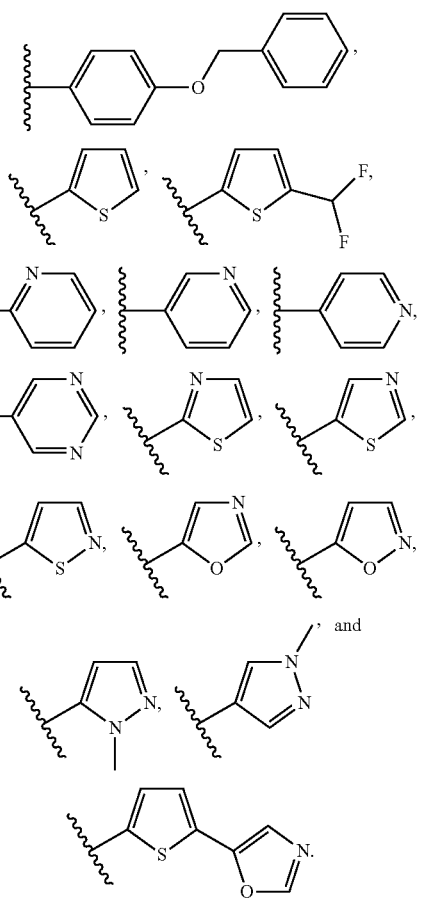

An embodiment of the present invention includes compounds of Formula I where R is selected from:

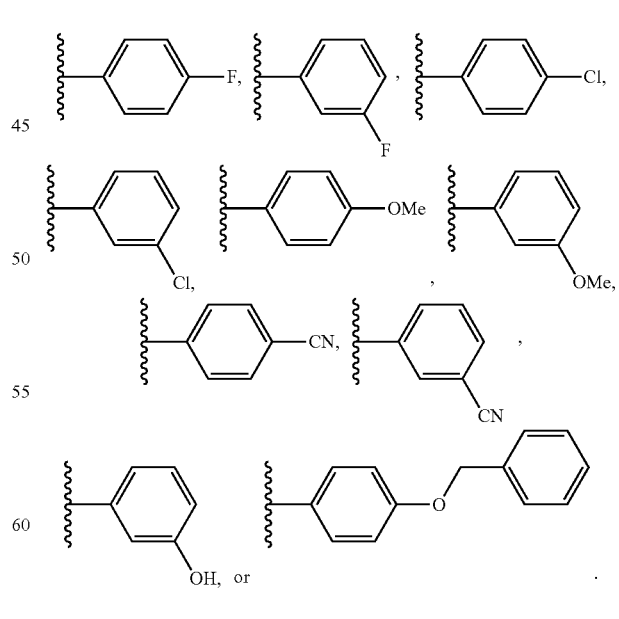

An embodiment of the present invention includes compounds of Formula I, wherein R is selected from the group consisting of:

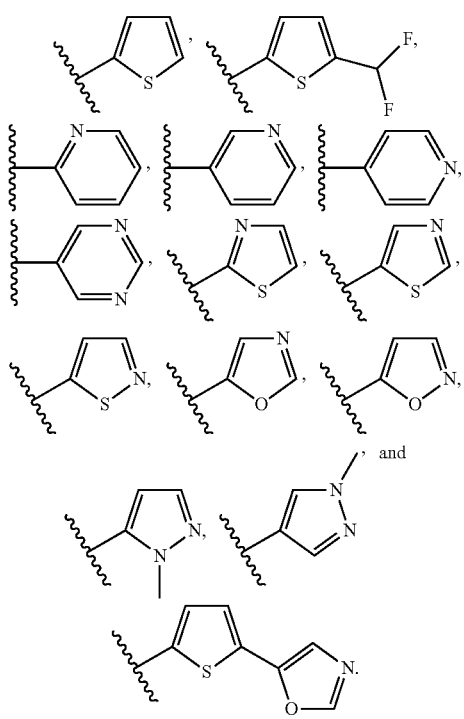

An embodiment of the present invention includes a compound having the chemical structure of Formula IIa

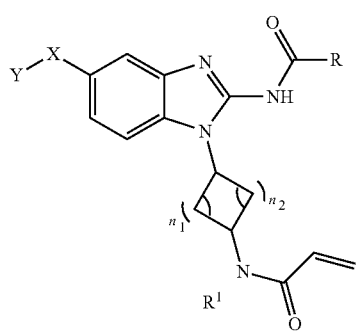

Formula IIa wherein
R is selected from substituted or unsubstituted 5- and 6-membered aryl ring or substituted or unsubstituted 5- and 6-membered heteroaryl ring;
X—Y is selected from the group consisting of:
—$CH_2$—NH—Y, —$CH_2$—$NR^2$—Y, —$CH_2$—$NR^3$—Y, —$NR^2C(O)$—Y, —$C(O)NR^2$—Y, or —$CH_2$—Y;
wherein
  $R^2$ is selected from hydrogen, $C_{1-6}$ alkyl chain or 3- to 8-membered cycloalkyl ring;
  $R^3$ is selected from —$C(O)R^4$, —$C(O)OR^4$ or —$S(O)_m$ $R^4$; wherein m is an integer from 1 to 2;
  $R^4$ is selected from $C_{1-6}$ alkyl chain or 3- to 8-membered cycloalkyl ring;
  Y is selected from the group consisting of hydrogen, halogen, substituted or unsubstituted $C_{1-6}$ alkyl chain, substituted or unsubstituted $C_{2-6}$ alkenyl chain, substituted or unsubstituted $C_{2-6}$ alkynyl chain, substituted or unsubstituted heteroalkyl chain of 2 to 6 atoms, substituted or unsubstituted 3- to 8-membered cycloalkyl ring, substituted or unsubstituted 3- to 8-membered heterocyclyl ring, substituted or unsubstituted 5-, and 6-membered aryl ring, substituted or unsubstituted 5-, and 6-membered heteroaryl ring, substituted or unsubstituted aralkyl, or substituted or unsubstituted heteroaralkyl;
$n_1$ is an integer from 0 to 3;
$n_2$ is an integer from 1 to 3; and
$R^1$ is selected from hydrogen, $C_{1-6}$ alkyl chain or 3- to 8-membered cycloalkyl ring.

The compound of Formula IIa is preferably the compound represented by Formula IIa or a pharmaceutically acceptable salt or solvate thereof. It may just be the simple compound of Formula IIa in one embodiment.

An embodiment of the present invention includes a compound having the chemical structure of Formula IIb

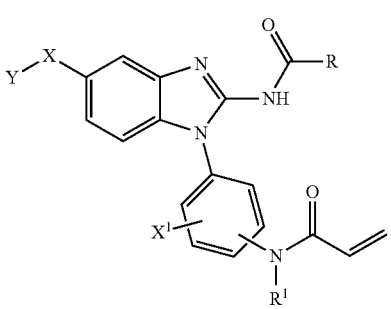

Formula IIb wherein
R is selected from substituted or unsubstituted 5- and 6-membered aryl ring or substituted or unsubstituted 5- and 6-membered heteroaryl ring;
X—Y is selected from the group consisting of:
—$CH_2$—NH—Y, —CH—$NR^2$—Y, —$CH_2$—$NR^3$—Y, —$NR^2C(O)$—Y, —$C(O)NR^2$—Y, or —$CH_2$—Y;
wherein
  $R^2$ is selected from hydrogen, $C_{1-6}$ alkyl chain or 3- to 8-membered cycloalkyl ring;
  $R^3$ is selected from —$C(O)R^4$, —$C(O)OR^4$ or —$S(O)_m R^4$; wherein m is an integer from 1 to 2;
  $R^4$ is selected from $C_{1-6}$ alkyl chain or 3- to 8-membered cycloalkyl ring;
  Y is selected from the group consisting of hydrogen, halogen, substituted or unsubstituted $C_{1-6}$ alkyl chain, substituted or unsubstituted $C_{2-6}$ alkenyl chain, substituted or unsubstituted $C_{2-6}$ alkynyl chain, substituted or unsubstituted heteroalkyl chain of 2 to 6 atoms, substituted or unsubstituted 3- to 8-membered cycloalkyl ring, substituted or unsubstituted 3- to 8-membered heterocyclyl ring, substituted or unsubstituted 5-, and 6-membered aryl ring, substituted or unsubstituted 5-, and 6-membered heteroaryl ring, substituted or unsubstituted aralkyl, or substituted or unsubstituted heteroaralkyl;
$X^1$ is selected from hydrogen or halogen; and
$R^1$ is selected from hydrogen, $C_{1-6}$ alkyl chain or 3- to 8-membered cycloalkyl ring.

The compound of Formula IIb is preferably the compound represented by Formula IIb or a pharmaceutically acceptable salt or solvate thereof. It may just be the simple compound of Formula IIb in one embodiment.

An embodiment of the present invention includes a compound having the chemical structure of Formula IIc

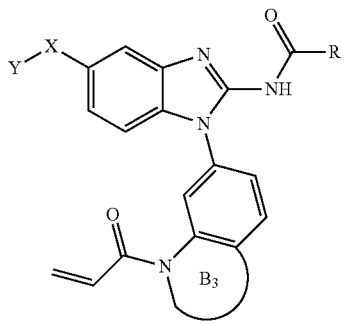

Formula IIc wherein
R is selected from substituted or unsubstituted 5- and 6-membered aryl ring or substituted or unsubstituted 5- and 6-membered heteroaryl ring;
X—Y is selected from the group consisting of:
—CH$_2$—NH—Y, —CH—NR$^2$—Y, —CH$_2$—NR$^3$—Y, —NR$^2$C(O)—Y, —C(O)NR$^2$—Y, or —CH$_2$—Y;
wherein
  R$^2$ is selected from hydrogen, C$_{1-6}$ alkyl chain or 3- to 8-membered cycloalkyl ring;
  R$^3$ is selected from —C(O)R$^4$, —C(O)OR$^4$ or —S(O)$_m$R$^4$; wherein m is an integer from 1 to 2;
  R$^4$ is selected from C$_{1-6}$ alkyl chain or 3- to 8-membered cycloalkyl ring;
  Y is selected from the group consisting of hydrogen, halogen, substituted or unsubstituted C$_{1-6}$ alkyl chain, substituted or unsubstituted C$_{2-6}$ alkenyl chain, substituted or unsubstituted C$_{2-6}$ alkynyl chain, substituted or unsubstituted heteroalkyl chain of 2 to 6 atoms, substituted or unsubstituted 3- to 8-membered cycloalkyl ring, substituted or unsubstituted 3- to 8-membered heterocyclyl ring, substituted or unsubstituted 5-, and 6-membered aryl ring, substituted or unsubstituted 5-, and 6-membered heteroaryl ring, substituted or unsubstituted aralkyl, or substituted or unsubstituted heteroaralkyl; and
ring B$_3$ is a 3- to 8-membered substituted or unsubstituted heterocyclic ring.

The compound of Formula IIc is preferably the compound represented by Formula IIc or a pharmaceutically acceptable salt or solvate thereof. It may just be the simple compound of Formula IIc in one embodiment.

Compounds of Formula I can exist as tautomers. For example, compounds of Formula I can exist in the following tautomeric forms and both tautomeric forms comprise part of the present invention:

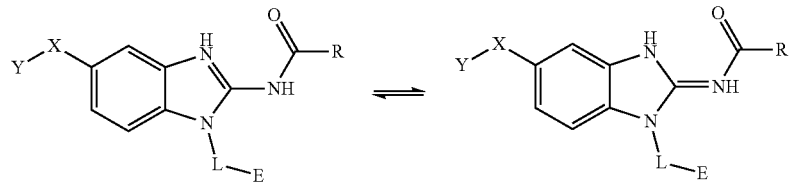

wherein R, X, Y, L and E are as defined above.

In an embodiment of the present invention compounds are selected from the group consisting of

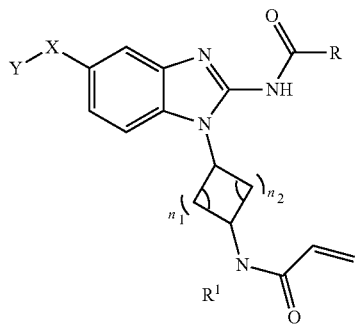

Formula IIa

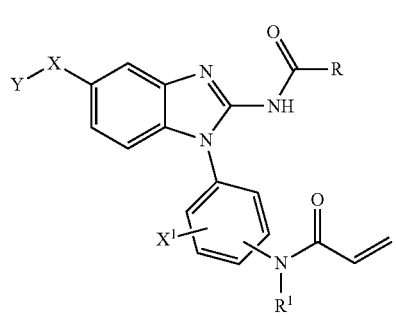

Formula IIb

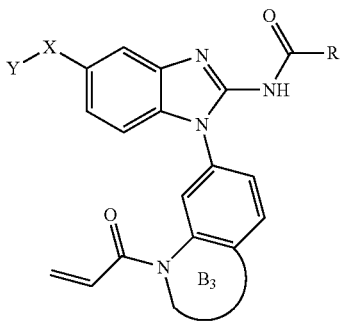

Formula IIc and pharmaceutically acceptable salts, solvates, solvate of salts, stereoisomers, tautomers, isotopes, prodrugs, and complex or biologically active metabolites thereof.

The compounds of the present invention may have activity as inhibitors of protein kinases including tyrosine protein kinases. Most particularly, compounds of the present invention may inhibit ITK enzyme and ITK-dependent cellular functions.

In an embodiment of the present invention compounds of Formula I may be formulated into a pharmaceutical composition which comprises an effective amount of a compound of the present invention with a pharmaceutically acceptable diluent or carrier.

According to the present invention there is provided a pharmaceutical composition which comprises a compound of Formula I, or a pharmaceutically acceptable salt or solvate thereof, in association with at least one pharmaceutically acceptable excipient, diluent or carrier.

The pharmaceutical compositions may be in a conventional pharmaceutical form suitable for oral administration (e.g., tablets, capsules, granules, powders and syrups), parenteral administration (e.g., injections (intravenous, intramuscular, or subcutaneous)), drop infusion preparations, inhalation, eye lotion, topical administration (e.g., ointment), or suppositories. Regardless of the route of administration selected, the compounds may be formulated into pharmaceutically acceptable dosage forms by conventional methods known to those skilled in the art.

The term "compound" refers also to its pharmaceutically acceptable salt, solvate, solvate of salt, stereoisomer, tautomer, isotope, prodrug, complex or biologically active metabolite thereof.

The term "pharmaceutically effective amount" refers to any amount of the composition for the prevention and treatment of humans that is effective in preventing or treating a disease or condition associated with protein kinase activity.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be acceptable in the sense of being compatible with the other ingredients of the formulation, including the active ingredient, and not injurious or harmful to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. For oral formulations, "pharmaceutically acceptable carrier" such as cellulose, calcium silicate, corn starch, lactose, sucrose, dextrose, calcium phosphate, stearic acid, magnesium stearate, calcium stearate, gelatin, talc, surfactants, suspending agents, emulsifiers, diluents, and others may be used. For injectable formulations, "pharmaceutically acceptable carrier" such as water, saline, glucose solution, glucose solution analogs, alcohols, glycols, ethers (e.g., polyethylene glycol 400), oils, fatty acids, fatty acid esters, glycerides, surfactants, suspending agents, emulsifiers, and others may be used.

The term "pharmaceutically acceptable salt" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like (See, for example, Berge et al. (1977) "Pharmaceutical Salts", J. Pharm. Sci. 66: 1-19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

As used herein, the term "affinity tag" means a ligand or group, linked either to a compound of the present invention or to a protein kinase domain, that allows the conjugate to be extracted from a solution.

The term "spirocycle", as used herein, refers to bicyclic rings system connected through just one atom. The rings can be different or identical. The connecting atom, also called spiroatom, is preferably a quaternary carbon. Spirocycle may be optionally substituted with one or more substituents as defined herein.

The term "alkyl", as used herein, refers to a saturated hydrocarbon chain. Alkyl chains may be straight or branched. Alkyl chains may be optionally substituted with one or more substituents as defined herein. Representative alkyl groups include methyl, ethyl, propyl, (n-propyl and isopropyl) butyl (n-butyl, t-butyl and isobutyl), pentyl (n-pentyl and isopentyl), hexyl and the like. In certain preferred embodiments, alkyl substituents are lower alkyl groups, e.g., having from 1 to 6 carbon atoms, and in certain embodiments having $C_1$ to $C_3$ carbon atoms.

The term "alkenyl", as used herein, refers to an unsaturated hydrocarbon chain analogous in length and possible substitution to the "alkyl" described above, but that contain at least one double bond. Representative alkenyl groups include vinyl, propen-2-yl, crotyl, isopenten-2-yl, 1,3-butadien-2-yl, 2,4-pentadienyl, and 1,4-pentadien-3-yl. In certain preferred embodiments, alkenyl substituents are lower alkenyl groups, e.g., having from 2 to 6 carbon atoms.

The term "alkynyl", as used herein, refers to an unsaturated hydrocarbon chain analogous in length and possible substitution to the "alkyl" described above, but that contain at least one triple bond. Representative alkynyl groups include ethynyl, 1- and 3-propynyl, and 3-butynyl. In certain preferred embodiments, alkynyl substituents are lower alkyl groups, e.g., having from 2 to 6 carbon atoms.

The term, "alkylene", as used herein, refers to an alkyl group with two open valencies.

The term "heteroalkyl", as used herein, refers to a saturated or partially saturated chain containing one to four heteroatoms selected from the group consisting of O, N and S, and wherein the nitrogen and sulfur atoms may optionally be oxidized and the nitrogen atom may optionally be quaternized. Heteroalkyl chains may be straight or branched. Heteroalkyl chains may be optionally substituted with one or more substituents as defined herein. The heteroatom(s) O, N and S may be placed at any interior position of the heteroalkyl group. Up to two heteroatoms may be consecutive.

The term "cycloalkyl", as used herein, alternatively "carbocycle" and "carbocyclyl" refers to a saturated or partially saturated non-aromatic ring, more preferably 3- to 8-membered ring, in which each atom of the ring is carbon or; refers to a spirocycle where each ring is a saturated or partially saturated hydrocarbon ring and the spiro atom is carbon. Cycloalkyl rings may be optionally substituted with one or more substituents as defined herein. The term "cycloalkyl", "carbocycle" or "carbocyclyl" also include polycyclic ring systems having two or more cyclic rings in which two or more carbons are common to two adjoining rings wherein at least one of the rings is cycloalkyl, e.g., the other cyclic rings can be aryls, heteroaryls, and/or heterocyclyls. Representative cycloalkyl rings include cyclopropyl, cyclobutyl, cyclopentyl, cyclohexyl, 1-cyclohexenyl, 3-cyclohexen-1-yl, cycloheptyl, tetrahydronaphthyl, indanyl, adamantly and combinations thereof.

The term "heterocyclyl" alternatively "heterocyclic", as used herein, refers to non-aromatic ring structures, more preferably 3- to 8-membered rings, whose ring structures include one to four heteroatoms or; refers to a spirocycle where the bicyclic rings system contains 1 to 4 heteroatoms. Heterocyclyl rings may be optionally substituted with one or more substituents as defined herein. The term "heterocyclyl" or "heterocyclic" also include polycyclic ring systems having two or more cyclic rings in which two or more carbons are common to two adjoining rings wherein at least one of the rings is heterocyclic, e.g., the other cyclic rings can be cycloalkyls, aryls and/or heteroaryls. Heterocyclyl groups include, for example, tetrahydrofuran, piperidine, piperazine, pyrrolidine, morpholine, lactones, lactams and combinations thereof.

The term "aryl", as used herein, refers to 5-, 6-, and 7-membered aromatic rings in which each atom of the ring is carbon. Aryl rings may be optionally substituted with one or more substituents as defined herein. The term "aryl" also includes polycyclic ring systems having two or more cyclic rings in which two or more carbons are common to two adjoining rings wherein at least one of the rings is aryl, e.g., the other cyclic rings can be cycloalkyls, heteroaryls, and/or heterocyclyls. Aryl groups include, for example, benzene, naphthalene, phenanthrene, anthracene and combinations thereof.

The term "heteroaryl" as used herein, refers to 5-, 6-, and 7-membered aromatic rings whose ring structures include one to four heteroatoms. Heteroaryl rings may be optionally substituted with one or more substituents as defined herein. The term "heteroaryl" also includes polycyclic ring systems having two or more cyclic rings in which two or more carbons are common to two adjoining rings wherein at least one of the rings is heteroaryl, e.g., the other cyclic rings can be cycloalkyls, aryls and/or heterocyclyls. Heteroaryl groups include, for example, pyrrole, furan, thiophene, imidazole, isoxazole, oxazole, thiazole, triazole, pyrazole, pyridine, pyrazine, pyridazine and pyrimidine, and combinations thereof.

The terms "polycyclyl" alternatively "polycyclic", as used herein, refer to two or more rings (e.g., cycloalkyls, aryls, heteroaryls, and/or heterocyclyls) in which two or more carbons are common to two adjoining rings, e.g., the rings are "fused rings". Polycyclyl rings may be optionally substituted with one or more substituents as defined herein.

The term "aralkyl", as used herein, refers to an alkyl group substituted with an aryl group, for example —$(CH_2)_p$—Ar and p is an integer from 1 to 8 and Ar may be selected from any suitable aryl ring system, for example phenyl or napthyl. For example "aralkyl" may be benzyl.

The term "heteroaralkyl", as used herein, refers to an alkyl group substituted with a heteroaryl group, for example —$(CH_2)_p$-Het and p is an integer from 1 to 8 and Het is any suitable heteroaryl ring system, such as those discussed in the above paragraphs.

The term "alkoxy", as used herein, refers to an alkyl ether substituent, wherein the term alkyl is as defined above. Representative alkoxy groups include methoxy, ethoxy, propoxy, tert-butoxy and combinations thereof.

The term "ether", as used herein, refers to an oxy group bridging two moieties linked at carbon atoms.

The term "alkoxyalkyl", as used herein, refers to an alkyl group substituted with an alkoxy group, thereby forming ether.

The term "halo" or "halogen", as used herein, refers to fluorine, chlorine, bromine and iodine.

The term "heteroatom", as used herein, refers to an atom of any element other than carbon or hydrogen. Preferred heteroatoms are nitrogen, oxygen, and sulfur.

The term "hydrocarbon", as used herein, refers to a group consisting entirely of carbon and hydrogen.

The term "haloalkyl", as used herein, refers to an alkyl substituent wherein one or more hydrogens are replaced by a halogen.

The term "carbonyl", as used herein, when alone includes formyl —CH(O) and in combination is a —C(O) group.

The term "carboxyl", alternatively "carboxy", as used herein, refers to —C(O)OH or the corresponding "carboxylate" anion, such as in a carboxylic acid salt.

The term "acyl", as used herein, refers to —C(O)R wherein R is alkyl, heteroalkyl, haloalkyl, cycloalkyl, heterocyclyl, aryl or heteroaryl as defined above. Representative acyl groups include acetyl, trifluoroacethyl, benzoyl, and the combinations thereof.

The term "alkoxycarbonyl", as used herein, refers to —C(O)OR wherein R is alkyl as defined above. Representative alkoxycarbonyl groups include methoxycarbonyl, ethoxycarbonyl, and the combinations thereof.

The term "alkylthio", as used herein, refers to a thioether —SR wherein R is alkyl as defined above. Representative alkylthio groups include methylthio, ethytthio and combinations thereof.

The term "sulfonate", as used herein, refers to a salt or ester of a sulfonic acid —$OSO_2R$ wherein R is alkyl, heteroalkyl, haloalkyl, cycloalkyl, heterocyclyl, aryl or heteroaryl as defined above. Representative sulfonate groups include mesylate, besylate, tosylate, and combinations thereof.

The term "sulfonyl", as used herein, refers to —$SO_2R$ wherein R is alkyl, heteroalkyl, haloalkyl, cycloalkyl, heterocyclyl, aryl or heteroaryl as defined above. Representative sulfonate groups include methylsufonyl, ethylsulfonyl, and combinations thereof.

The term "sulfamoyl", as used herein, refers to —SO$_2$NH$_2$.

The term "sulfonamido", as used herein, refers to —S(O)$_2$NRR' wherein R and R' are independently selected from alkyl, heteroalkyl, haloalkyl, cycloalkyl, heterocyclyl, aryl and heteroaryl as defined above. R and R' may combine to form a heterocyclyl ring.

The term "amino", as used herein, refers to —NRR' wherein R and R' are independently selected from hydrogen, alkyl, heteroalkyl, haloalkyl, cycloalkyl, heterocyclyl, aryl and heteroaryl as defined above. R and R' may combine to form a heterocyclyl ring.

The term "amido" alternatively "amide", as used herein, refers to —C(O)NRR' wherein R and R' are independently selected from hydrogen, alkyl, heteroalkyl, haloalkyl, cycloalkyl, heterocyclyl, aryl or heteroaryl as defined above. R and R' may combine to form an heterocyclyl ring.

The term "substituted" refers to moieties having substituents replacing hydrogen on one or more atoms of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms.

Substituents can include, for example, an alkyl, an alkenyl, an alkynyl, a haloalkyl, a heteroalkyl, a cycloalkyl, a heterocyclyl, an aryl, a heteroaryl, a halogen, a hydroxyl, a carbonyl, carboxyl, an alkoxycarbonyl, a formyl, or an acyl, a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl. It will be understood by those skilled in the art that the substituents can themselves be substituted, if appropriate.

As used herein, the term "probe" means a compound of the invention which is labeled with either a detectable label or an affinity tag, and which is capable of binding, either covalently or non-covalently, to a protein kinase domain. When, for example, the probe is non-covalently bound, it may be displaced by a test compound. When, for example, the probe is bound covalently, it may be used to form cross-linked adducts, which may be quantified and inhibited by a test compound.

The term "prodrug" denotes a compound that is a drug precursor which, upon administration to a subject, is converted within the body into a compound of Formula I, Formula IIa, Formula IIb or Formula IIc. Prodrugs of compounds of Formula I, Formula IIa, Formula IIb, Formula IIc or pharmaceutically acceptable salts or solvates thereof are within the scope of this disclosure.

The term "biologically active metabolite" means a pharmacologically active product produced through metabolism in the body of a specified compound or salt thereof.

The term "subject" or "patient" means a human or an animal subject for prevention or treatment.

In an embodiment the use is ex vivo, for example in vitro, such as an in vitro assay.

The term "combination" within the meaning of this invention includes the simultaneous, sequential or separate use of the components or ingredients.

Compounds of the invention also include all isotopes of atoms present in the Intermediates and/or final Compounds. Isotopes include those atoms having the same atomic number but different mass numbers. For example, isotopes of hydrogen include deuterium and tritium.

Therapeutic Uses and Applications

The compounds of the present invention are inhibitors of protein kinase activity and are suitable for use in therapy.

An aspect of the present invention provides a method of inhibiting protein kinase activity in a cell, the method comprising administering to said cell compound of Formula I as defined herein, or a pharmaceutically acceptable salt or solvate thereof.

In a further aspect, the present invention provides a method of inhibiting protein kinase in vitro or in vivo, said method comprising contacting a cell with an effective amount of a compound of Formula I, Formula IIa, Formula IIb, Formula IIc or a pharmaceutically acceptable salt, solvate, solvate of salt, stereoisomer, tautomer, isotope, prodrug, complex or biologically active metabolite thereof.

A further aspect of the present invention provides a method of inhibiting protein kinase activity in a human or animal subject for treatment or prevention of protein kinase mediated disease, the method comprising administering to said subject an effective amount of a compound of Formula I, Formula IIa, Formula IIb or Formula IIc as defined herein, or a pharmaceutically acceptable salt or solvate of salt, stereoisomer, tautomer, isotope, prodrug, complex or biologically active metabolite thereof.

The term "protein kinase mediated disease" is used herein associated with abnormal or undesirable cellular responses triggered or maintained by protein kinase-mediated events. Furthermore, aberrant activation, mutation or excessive expressions of various protein kinases are implicated in the mechanism of multiple diseases and disorders. These diseases include, but are not limited to cancer, autoimmune disease, inflammation, viral infection and neurological disease.

In one embodiment of this invention the disclosed compounds are used in the treatment of a patient that suffers from a disease or disorder that can be treated by kinase inhibition. The compound disclosed herein and/or pharmaceutically acceptable salt thereof can inhibit one or more kinases including but not limited to ITK, RLK (also known as TXK), BLK, BMX, BTK, JAK3, and/or TEC.

In one embodiment, the protein kinase inhibited by compounds of the present invention is ITK, BTK, BMX, RLK, or TEC singly or in combination.

The compounds of the present invention may be suitable for use in the treatment of or prevention of diseases that involve ITK, BTK, BMX, RLK or TEC, i.e. diseases that involve T cells and/or NK cells, for example, cancer, autoimmune diseases, allergic diseases, inflammatory diseases, viral infection and combinations thereof.

In one embodiment, a compound disclosed herein and/or pharmaceutically acceptable salt thereof is administered to a patient in need or recognized need thereof to prevent or treat an inflammatory disorder. In another embodiment, a compound disclosed herein and/or pharmaceutically acceptable salt thereof is administered to a patient in need or recognized need thereof to prevent or treat an inflammatory disorder characterized by excessive or undesired cytokine activity or production. In yet another embodiment, a compound and/or pharmaceutically acceptable salt thereof is administered to a patient in need or recognized need thereof to prevent or treat lung inflammation, allergic asthma, pneumonia, psoriasis, atopic dermatitis or a combination thereof. In yet another embodiment a compound and/or pharmaceutically acceptable salt thereof is administered to a patient in need of or recognized need thereof to prevent or treat uveitis or dry eye disease.

Examples of an autoimmune disease in the present invention include arthritis, systemic lupus erythematosus, rheumatoid arthritis, psoriasis, psoriatic arthritis, Still's disease, juvenile arthritis, type I diabetes, inflammatory bowel disease, myasthenia gravis, Hashimoto's thyroiditis, Ord's thyroiditis, Basedow's disease, Sjogren's syndrome, multiple sclerosis, Guillain-Barre syndrome, acute disseminated encephalomyelitis, Addison disease, opsocionus-myoclonus syndrome, ankylosing spondylitis, antiphospholipid antibody syndrome, aplastic anemia, autoimmune hepatitis, celiac disease, Goodpasture's syndrome, idiopathic thrombocytopenic purpura, optic neuritis, scleroderma, primary biliary cirrhosis, Reiter's disease, Takayasu arteritis, temporal arteritis, warm autoimmune hemolytic anemia, Wegener granuloma, alopecia universalis, Burchett disease, chronic fatigue syndrome, dysautonomia, endometriosis, interstitial cystitis, myotonia, vulvodynia, pemphigus, and combinations thereof.

Examples of an allergic disease in the present invention include allergy, anaphylaxis, allergic conjunctivitis, allergic rhinitis, atopic dermatitis and the combinations thereof.

Examples of an inflammatory disease in the present invention include asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, epicondylitis, epididymitis, fasciitis, fibrositis, gastritis, gastroenteritis, hepatitis, hidradenitis suppurativa, inflammatory bowel disease, laryngitis, mastitis, meningitis, myelitis, myocarditis, myositis nephritis, oophoritis, orchitis, osteitis, osteoarthritis, pancreatitis, parotitis, pericarditis, peritonitis, pharyngitis, pleuritis, phlebitis, pneumonia, proctitis, prostatitis, pyelonephritis, rhinitis, salpingitis, sinusitis, stomatitis, synovitis, tendinitis, tonsillitis, uveitis, vaginitis, vasculitis, vulvitis, and combinations thereof.

Examples of a viral infection include HIV/AIDS, influenza and combinations thereof.

Examples of cancer in the present invention include T-cell lymphomas and T-cell leukemias including peripheral T-cell lymphoma, Seazry syndrome/cutaneous T-cell lymphoma, acute lymphoblastic leukemia, and adult T-cell leukemia/lymphoma. Additional examples include NK/T-cell lymphoma, nasal type and aggressive NK-cell leukemia, as well as melanoma and hepatocellular carcinoma.

In one embodiment, the compound of Formula I, Formula IIa, Formula IIb, Formula IIc or pharmaceutically acceptable salts, solvates, solvates of salts, stereoisomers, tautomers, isotopes, prodrugs, complexes, or biologically active metabolites thereof, is acting by inhibiting one or more of the host cell kinases involved in cell proliferation, cell survival, viral replication, autoimmunity, an inflammatory disease or an infectious disease.

In further aspect of the present invention, is disclosed a method for treating a subject suffering from a protein kinase mediated disease or condition, comprising administering to the subject a therapeutically effective amount of the compound of Formula I, Formula IIa, Formula IIb, Formula IIc, or pharmaceutically acceptable salt, solvate, solvate of salt, stereoisomer, tautomer, isotope, prodrug, complex or biologically active metabolite thereof, in combination with at least one pharmaceutically acceptable carrier.

In further aspect of the present invention, the compound of Formula I, Formula IIa, Formula IIb, Formula IIc or pharmaceutically acceptable salts, solvates, solvates of salts, stereoisomers, tautomers, isotopes, prodrugs, complexes, or biologically active metabolites thereof, is acting as inhibitor of cell kinases as anti-inflammatory, autoimmune modulators or anti-cancer agents.

In a further aspect of the present invention, the compound of Formula I, Formula IIa, Formula IIb, Formula IIc or pharmaceutically acceptable salts, solvates, solvates of salts, stereoisomers, tautomers, isotopes, prodrugs, complexes, or biologically active metabolites thereof, is acting by inhibiting one or more of the host cell kinases involved in T-cell function proliferation or polarization.

The compounds of Formula I, Formula IIa, Formula IIb, Formula IIc or pharmaceutically acceptable salts, solvates, solvates of salts, stereoisomers, tautomers, isotopes, prodrugs, complexes, or biologically active metabolites thereof are suitable for use in the preparation of a medicament for inhibiting a protein kinase activity selected from ITK, BTK, BMX, RLK and combinations thereof in a subject.

The compounds of Formula I, Formula IIa, Formula IIb, Formula IIc or pharmaceutically acceptable salts, solvates, solvates of salts, stereoisomers, tautomers, isotopes, prodrugs, complexes, or biologically active metabolites thereof and pharmaceutically acceptable compositions of the present invention can be employed in combination therapies, the compounds and pharmaceutically acceptable compositions may have potential utility in combination with other therapies for the treatment of cancer, viral infections, immune, inflammatory, neurological diseases, proliferative and allergic disorders. Example includes but not limited to co-administration with steroids, leukotriene antagonists, antihistamines, anti-cancer, anti-viral, anti-biotic agents or other protein kinase inhibitors. The anti-cancer agent may be selected from the group consisting of: cell signal transduction inhibitors, mitosis inhibitors, alkylating agents, antimetabolites, intercalating anticancer agents, topoisomerase inhibitors, immunotherapic agents, anti-hormonal agents, and a mixture thereof. The additional active pharmaceutical ingredient used in the combination is appropriate for the disease being treated and said additional active pharmaceutical ingredient is administered together with the compounds of Formula I, Formula IIa, Formula IIb, Formula IIc as a single dosage form or separately as part of a multiple dosage form.

The compounds of the present invention are indicated both in the therapeutic and/or prophylactic treatment of the above-mentioned conditions. For the above-mentioned therapeutic and/or prophylactic uses the dosage administered will vary with the compound employed, the subject, the mode of administration, the treatment desired and the disorder indicated. The daily dosage may be between about 0.01 mg/kg to about 100 mg/kg and preferably from about 1 mg/kg to about 25 mg/kg, of the subject body weight per day, one or more times a day, to obtain the desired therapeutic effect.

A pharmaceutical acceptable composition of the present invention may be obtained by conventional procedures using conventional pharmaceutical excipients, well known in the art. It may typically comprise pharmaceutically acceptable additives, carriers or excipients. The pharmaceutical composition of the present invention may be formulated in accordance with conventional methods, and may be prepared in the form of oral formulations such as tablets, pills, powders, capsules, syrups, emulsions, microemulsions and others, or parenteral formulations such as intramuscular, intravenous or subcutaneous administrations.

For oral formulations, carriers or additives such as cellulose, calcium silicate, corn starch, lactose, sucrose, dextrose, calcium phosphate, stearic acid, magnesium stearate, calcium stearate, gelatin, talc, surfactants, suspending agents, emulsifiers, diluents, and others may be used. Solid dosage forms for oral administration include capsules, tablets, pills, powders, and granules. Liquid dosage forms for oral administration include, but are not limited to, pharmaceutically acceptable emulsions, microemulsions, solutions, suspensions, syrups and elixirs. The liquid dosage forms may contain inert diluents and can also include adjuvants such as wetting agents, emulsifying and suspending agents, sweetening, flavoring, and perfuming agents.

The present invention contemplates compounds of Formula I, Formula IIa, Formula IIb, Formula IIc or pharmaceutical salts thereof. The invention also contemplates solvates, solvates of salts, stereoisomers, tautomers, isotopes, prodrugs, complexes or biologically active metabolites of the compounds of Formula I, Formula IIa, Formula IIb and Formula IIc.

For Injectable formulations, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The compounds of Formula I, Formula IIa, Formula IIb, Formula IIc, or pharmaceutically acceptable salt, solvate, solvate of salt, stereoisomer, tautomer, isotope, prodrug, complex, or biologically active metabolites thereof and pharmaceutically acceptable compositions of the present invention can be employed in combination therapies, wherein the additional active pharmaceutical ingredient is selected from the group comprising steroids, leukotriene antagonists, anti-histamines, anti-cancer, anti-viral, anti-biotic agents, protein kinase inhibitors and combinations thereof.

A probe comprising the compound of Formula I, Formula IIa, Formula IIb, Formula IIc covalently conjugated to a detectable label or affinity tag for said compound. The probe, wherein the detectable label is selected from the group consisting of a fluorescent moiety, a chemiluminescent moiety, a paramagnetic contrast agent, a metal chelate, a radioactive isotope containing moiety and biotin.

Specific Abbreviations Used

AIDS Acquired Immune Deficiency Syndrome
ATP Adenosine Triphosphate
BLK B lymphocyte kinase
BMX Bone marrow-expressed kinase
BTK Bruton's Tyrosine Kinase
DMSO Dimethyl sulfoxide
EDTA Ethylenediaminetetraacetic acid
FCS Fetal Calf serum
HIV Human immunodeficiency virus
JAK3 Janus Kinase
ITK Interleukin-2 inducible T-cell kinase
NK/T-cell Natural killer T-cell
PBMC Peripheral blood mononuclear cells
PBS Phosphate buffered saline
RPMI Roswell Park Memorial Institute medium
RLK/TXK Resting lymphocyte kinase
TEC Tyrosine kinase expressed in carcinoma
Tec Family of protein-tyrosine kinases
MS mass spectrometry
ml milliliter
μl microliter
mmol millimole
THF tetrahydrofuran
DMF dimethylformamide
MeOH methanol
EtOH ethanol
THF tetrahydrofuran
DCM dichloromethane
EtOAc Ethyl acetate
AcOH acetic acid
$K_2CO_3$ Potassium carbonate
NaH Sodium hydride
Pd/C Palladium on carbon
TEA triethylamine
DIPEA diisopropylethylamine
DEA diethylamine
$NaHCO_3$ sodium bicarbonate
$Cs_2CO_3$ cesium carbonate
$NaBH(OAc)_3$ sodium triacetoxyborohydride
CbzCl benzyl chloroformate
MsCl methanesulfonyl chloride
$Boc_2O$ di-tert-butyl dicarbonate
MeI Iodomethane
$MgSO_4$ magnesium sulfate
Zn Zinc dust
$SO_3$ Sulfur trioxide
BrCN cyanogen bromide
HBr hydrogen bromide
HCl Hydrogen chloride
TFA trifluoroacetic acid
HATU (1-[Bis(dimethylamino)methylene]-1H-1,2,3-triazolo[4,5-b]pyridinium 3-oxid hexafluorophosphate)
H BTU (2-(1H-benzotriazol-1-yl)-1,1,3,3-tetramethyluronium hexafluorophosphate)
$Pd_2dba_3$ Tris(dibenzylideneacetone)dipalladium(0)
XPhos 2-Dicyclohexylphosphino-2',4',6'-triisopropylbiphenyl
$NaN_3$ sodium azide General Synthetic Methods In the description of the synthetic methods described below and in the referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

The following section describes general synthetic method(s) which may be useful in the preparation of compounds of the instant invention.

Compounds of Formula I where L-E is selected from

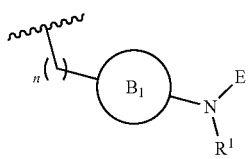

and X—Y is selected from —CH—NH—Y
are prepared as described below:

Intermediate A3 is obtained by reacting commercially available Intermediate A1 with an amine of formula A2 where ring $B_1$, n and $R^1$ are as defined above and $PG^1$ is a suitable protecting group. Reductive amination of Intermediate A3 with an amine of formula $YNH_2$ where Y is as defined above provides Intermediate A4. Protection of the alkyl amino group with a suitable protective group $PG^2$ provides Intermediate A5. Reduction of the nitro group provides Intermediate A6 which is then cyclized to the corresponding aminobenzimidazole Intermediate A7. Coupling of Intermediate A7 with an acid of formula $RCO_2H$ under standard coupling conditions or with an activated acid of formula RC(O)LG, where R is as defined above and LG is a leaving group, provides Intermediate A8. Removal of $PG^1$ protecting group provides Intermediate A9.

Compounds of Formula I are then obtained from Intermediate A9 by first coupling Intermediate 9 with an acid of formula

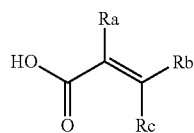

under standard coupling conditions or with an activated acid of formula

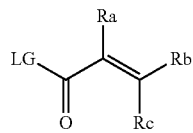

where $R^a$, $R^b$ and $R^c$ are as defined above and LG is a leaving group followed by removal of $PG^2$ protective group.

Scheme A

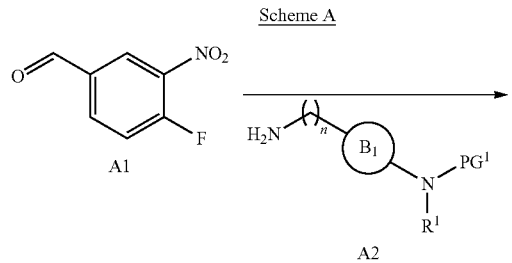

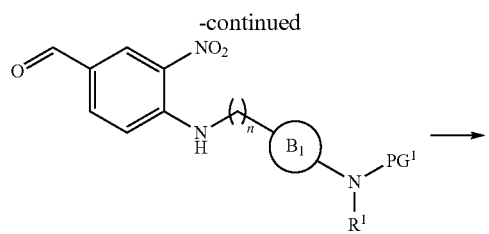

A3

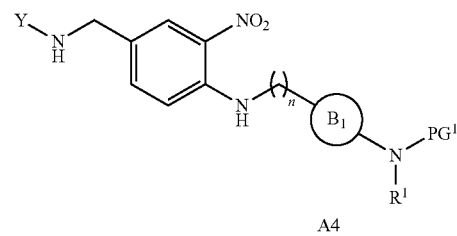

A4

A4 ⟶

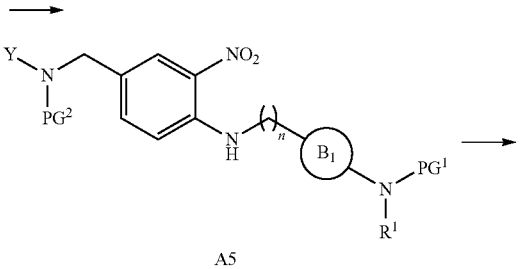

A5

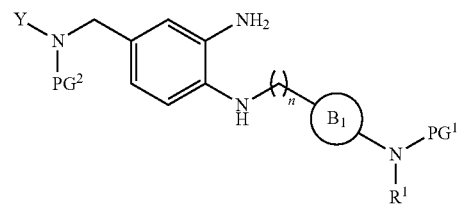

A6

A6 ⟶

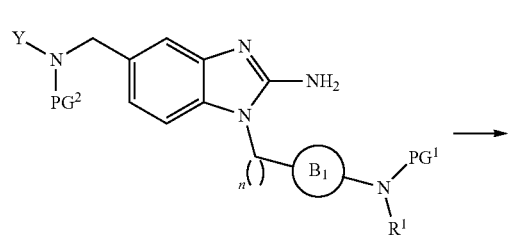

A7

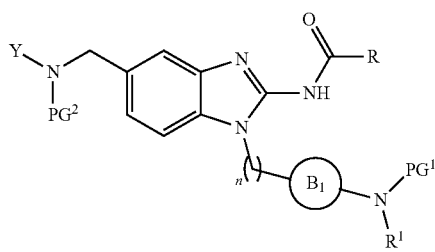

A8

-continued

A8 →

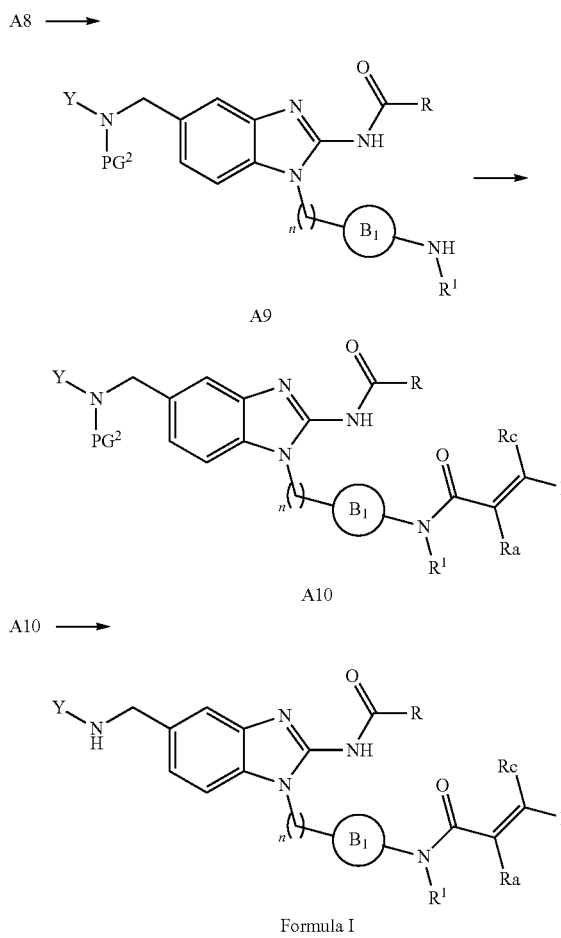

A10 →

Formula I

Compounds of Formula I where L-E is selected from

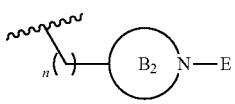

and X—Y is selected from —CH$_2$—NH—Y are prepared in a similar manner by substituting

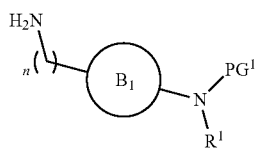

with

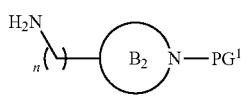

where ring B$_2$, n and PG$^1$ are as defined above.

Compounds of Formula I where L-E is selected from

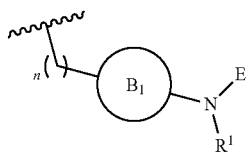

and X—Y is selected from —CH$_2$—NR$^2$—Y are prepared as described below:

Reduction of Intermediate A3 provides Intermediate B1. Protection of the alcohol group with a suitable protective group PG$^3$ provides Intermediate B2. Reduction of the nitro group provides Intermediate B3 which is then cyclized to the corresponding aminobenzimidazole Intermediate B4. Coupling of Intermediate B4 with an acid of formula RCO$_2$H under standard coupling conditions or with an activated acid of formula RC(O)LG where R is as defined above and LG is a leaving group provides intermediate Intermediate B5. Removal of PG$^1$ and PG$^3$ protecting groups provides intermediate Intermediate B6. Coupling of Intermediate B6 with an acid of formula

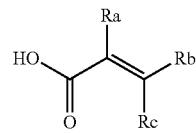

under standard coupling conditions or with an activated acid of formula

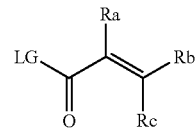

where R$^a$, R$^b$ and R$^c$ are as defined above and LG is a leaving group provides Intermediate B7 which is oxidized to provide Intermediate B8. Reductive amination of Intermediate B8 with an amine of formula Y—NHR$^2$ where Y and R$^2$ are as described above provides compounds of Formula I.

Scheme B

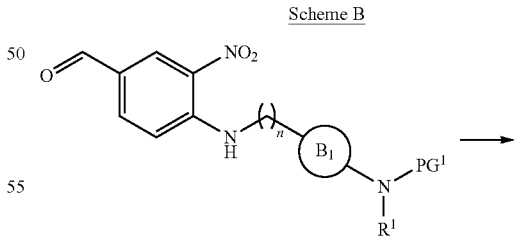

B1

-continued

B1 ⟶

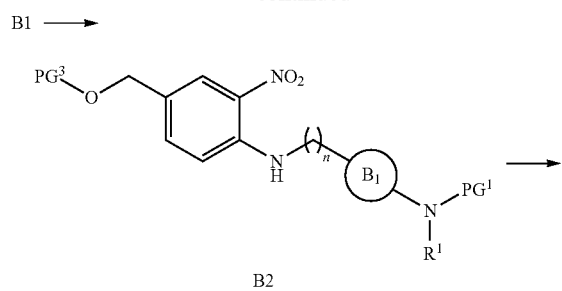
B2

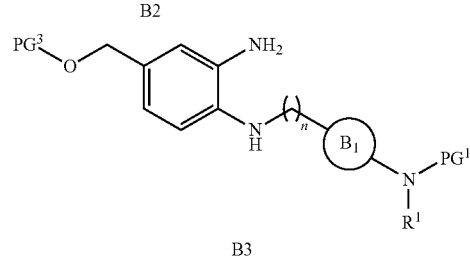
B3

B3 ⟶

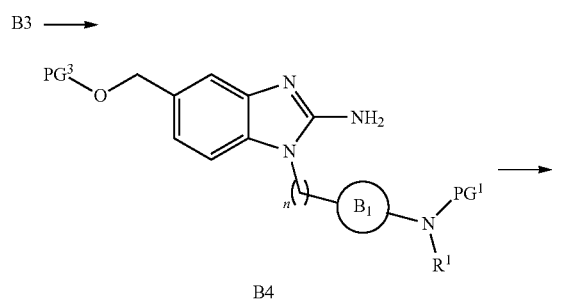
B4

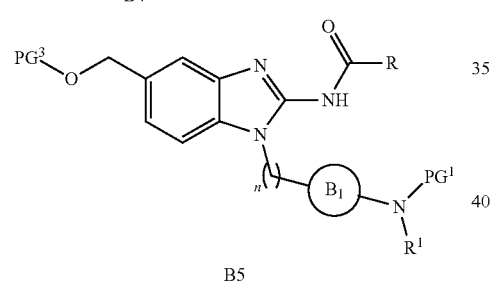
B5

B5 ⟶

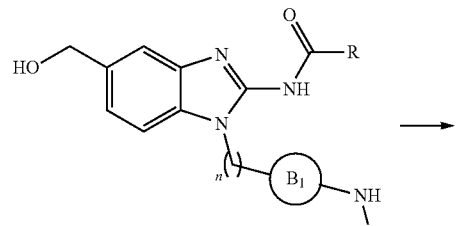
B6

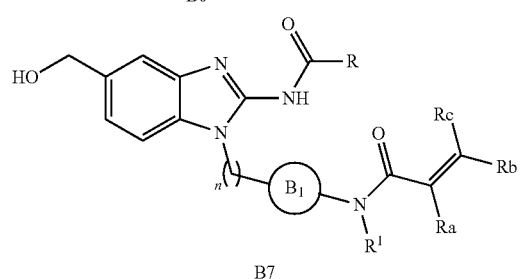
B7

-continued

B7 ⟶

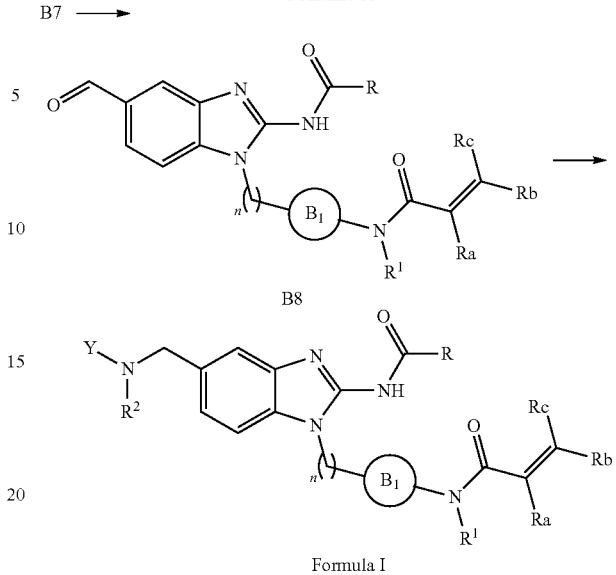
B8

Formula I

Compounds of Formula I where L-E is selected from

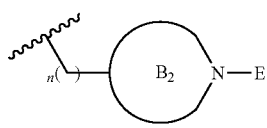

and X—Y is —CH$_2$—NR$^2$—Y are prepared in a similar manner by substituting

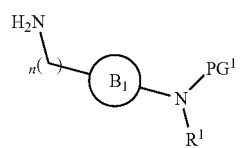

with

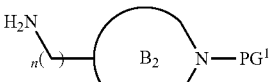

where ring B$_2$, n and PG$^1$ are as defined above.

Compounds of Formula I wherein L-E is selected from

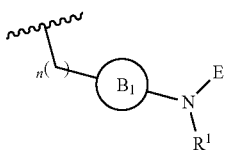

and X—Y is selected from —C(O)NR$^2$—Y are prepared as described below:

Intermediate C3 is obtained by coupling commercially available Intermediate C1 with an amine of formula YNHR$^2$ where Y and R² are as defined above under standard coupling conditions. Alternatively, Intermediate C3 is obtained in a 2 steps sequence by coupling Intermediate C1 with an amine of formula YNH₂ where Y is as defined above under standard coupling conditions followed by reacting Intermediate C2 with an Intermediate of formula R²LG, where R² is as defined above and LG is a leaving group, in a presence of a base. Intermediate C4 is obtained by reacting Intermediate C2 or C3 with an amine of formula A2 where ring $B_1$, n and R¹ are as defined above and PG¹ is a suitable protecting group. Reduction of the nitro group provides Intermediate C5 which is then cyclized to the corresponding aminobenzimidazole Intermediate C6. Coupling of Intermediate C6 with an acid of formula RCO₂H under standard coupling conditions or with an activated acid of formula RC(O)LG, where R is as defined above and LG is a leaving group, provides Intermediate C7. Removal of PG¹ protecting group provides Intermediate C8. Compounds of Formula I are then obtained by coupling Intermediate C8 with an acid of formula

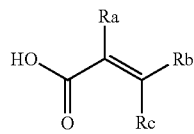

under standard coupling conditions or with an activated acid of formula

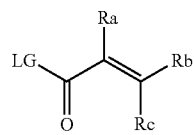

where $R^a$, $R^b$ and $R^c$ are as defined above and LG is a leaving group.

Scheme C

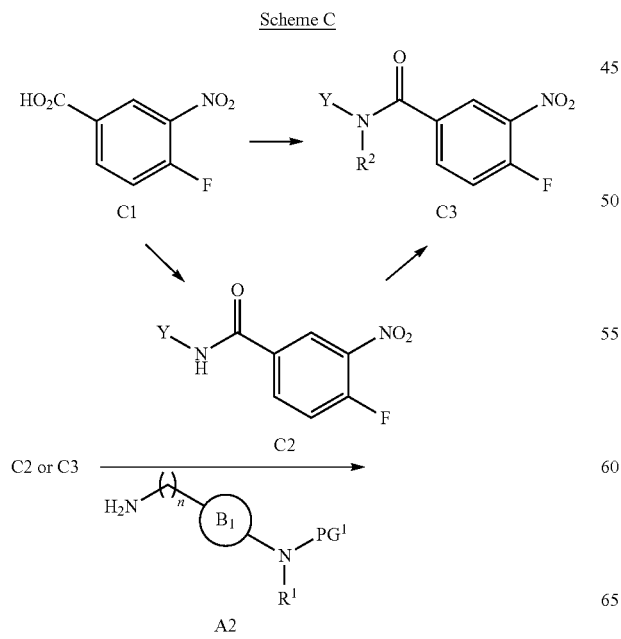

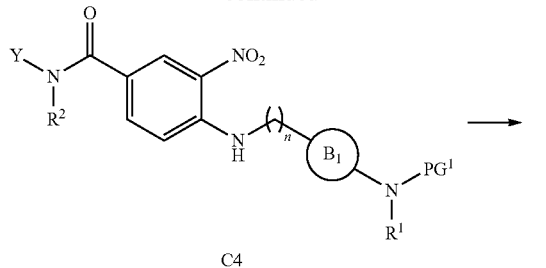

C4

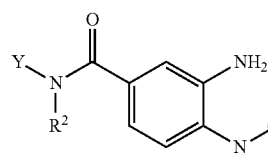

C5

C5 →

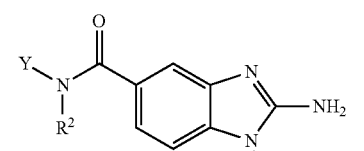

C6

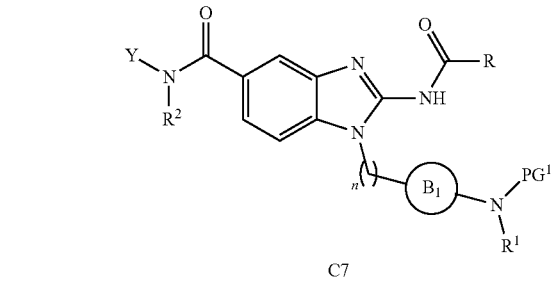

C7

C7 →

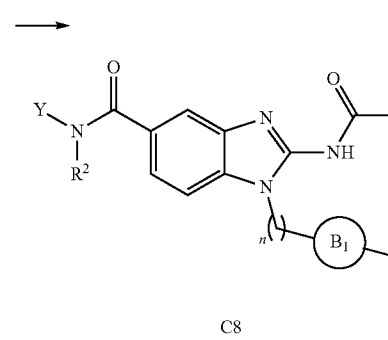

C8

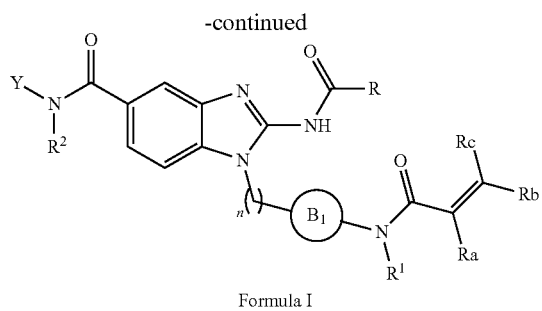

Formula I

Compounds of Formula I where L-E is selected from

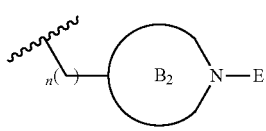

and X—Y is selected from —C(O)NR²—Y are prepared in a similar manner by substituting

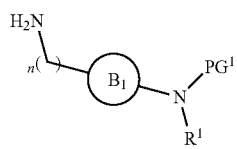

with

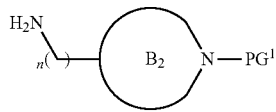

where ring $B_2$, n and $PG^1$ are as defined above.

Compounds of Formula I where L-E is selected from

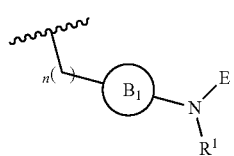

and X—Y is selected from —NR²C(O)—Y are prepared as described below:

Intermediate D3 is obtained in a 2 steps sequence by first reacting commercially available Intermediate D1 with an acid of formula $YCO_2H$ under standard coupling conditions or with an activated acid of formula YC(O)LG, where Y is as defined above and LG is a leaving group, to provide Intermediate D2; Intermediate D2 is then treated with R²LG, where R² is as defined above and LG is a leaving group, in a presence of a base to provide Intermediate D3. Intermediate D4 is obtained by reacting Intermediate D2 or D3 with an amine of formula A2 where ring $B_1$, n and $R^1$ are as defined above and $PG^1$ is a suitable protecting group. Reduction of the nitro group provides Intermediate C5 which is then cyclized to the corresponding aminobenzimidazole Intermediate D6. Coupling of Intermediate D6 with an acid of formula $RCO_2H$ under standard coupling conditions or with an activated acid of formula RC(O)LG where R is as defined above and LG is a leaving group provides Intermediate D7. Removal of $PG^1$ protecting group provides Intermediate D8. Compounds of Formula I are then obtained from Intermediate D8 by coupling Intermediate D8 with an acid of formula

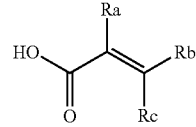

under standard coupling conditions or with an activated acid of formula

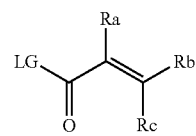

where $R^a$, $R^b$ and $R^c$ are as defined above and LG is a leaving group.

Scheme D

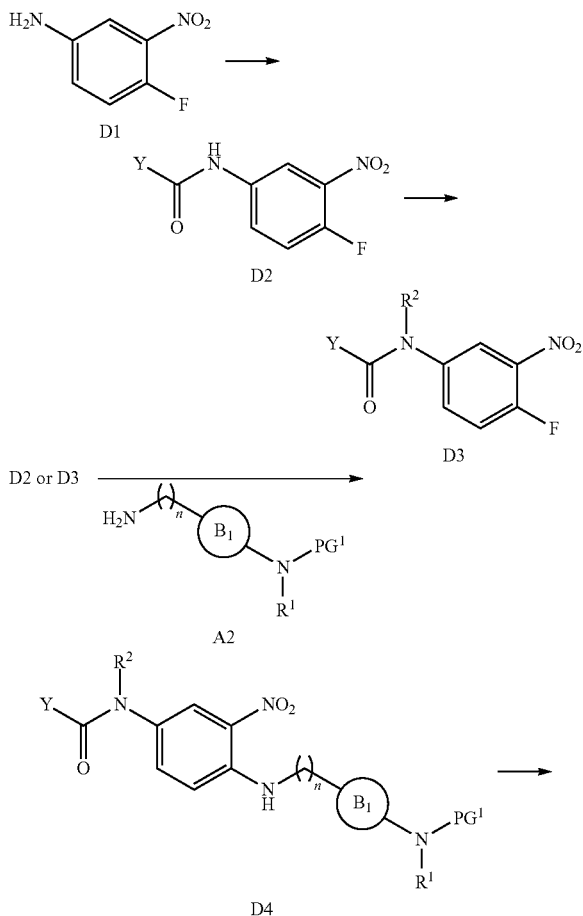

-continued

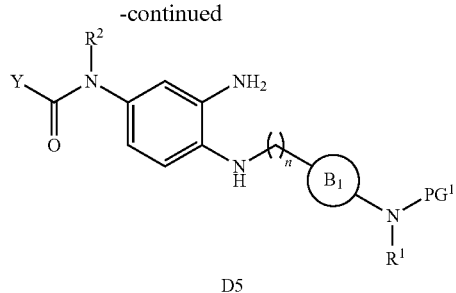

D5

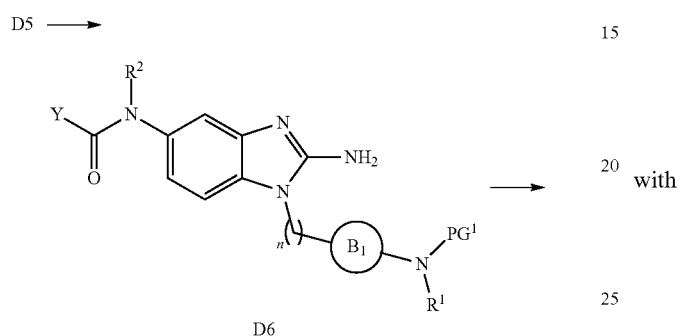

D6

D7

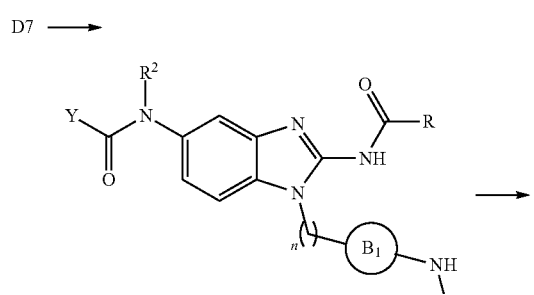

D8

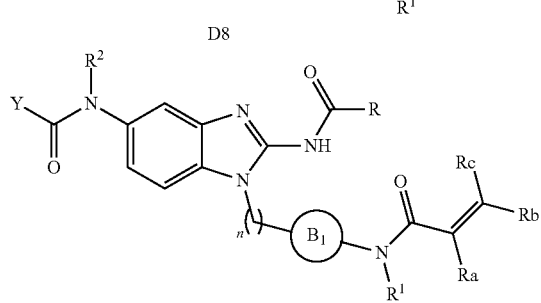

Formula I

Compounds of Formula I where L is selected from

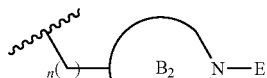

and X—Y is selected from —NR²C(O)—Y are prepared in a similar manner by substituting

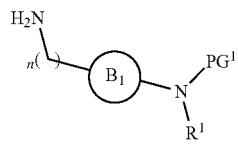

with

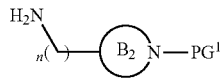

where ring $B_2$, n and P are as defined above.

In an alternative method compounds of Formula I wherein L-E is selected from

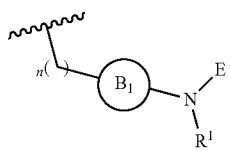

and X—Y is selected from —NR²C(O)—Y are prepared as described below:

Protection of commercially available Intermediate E1 provides Intermediate E2 where $R^2$ is as defined above and $PG^4$ is a suitable protecting group. Intermediate E3 is obtained by reacting Intermediates E2 with an amine of formula A2 where ring $B_1$, n and $R^1$ are as defined above and $PG^1$ is a suitable protecting group. Reduction of the nitro group provides Intermediate E4 which is then cyclized to the corresponding aminobenzimidazole Intermediate E5. Coupling of Intermediate E5 with an acid of formula $RCO_2H$ under standard coupling conditions or with an activated acid of formula RC(O)LG where R is as defined above and LG is a leaving group provides Intermediate E6. Removal of $PG^1$ protecting group provides Intermediate E7. Intermediates E8 is obtained by coupling Intermediate E7 with an acid of formula

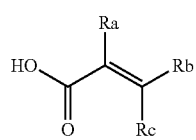

under standard coupling conditions or with an activated acid of formula

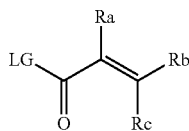

where $R^a$, $R^b$ and $R^c$ are as defined above and LG is a leaving group. Removal of $PG^4$ protecting group provides Intermediate E9. Coupling of Intermediate D9 with an acid of formula $YCO_2H$ under standard coupling conditions or with an activated acid of formula $YC(O)LG$ where Y is as defined above and LG is a leaving group provides compounds of Formula I.

Scheme E

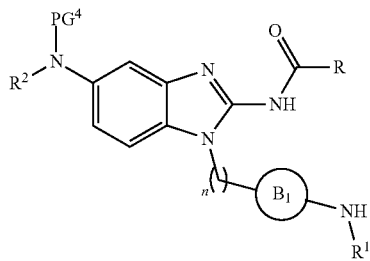

E1 → E2

A2

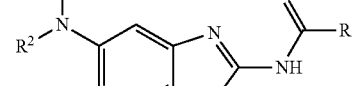

E3

E4

E5

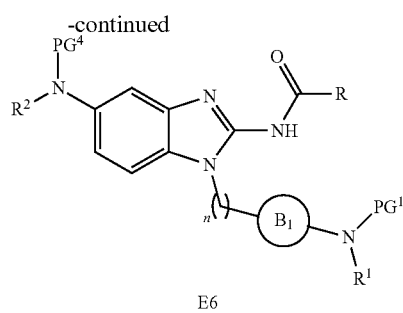

E6

E6 →

E7

E8

E8 →

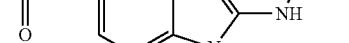

E9

Formula I

Compounds of Formula I where L is selected from

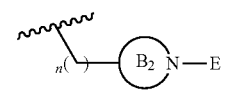

and X—Y is selected from —NR²C(O)—Y are prepared in a similar manner by substituting

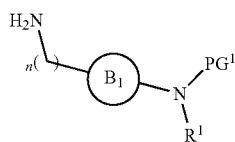

with

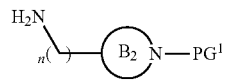

where ring $B_2$, n and $PG^1$ are as defined above.

Compounds of Formula I where L-E is selected from

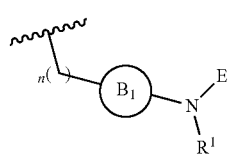

and X—Y is selected from —NR²SO₂—Y are prepared as described below:

Intermediate F3 is obtained in a 2 steps sequence by first reacting commercially available Intermediate F1 with an Intermediate of formula Y—SO₂-LG where Y is as defined and LG is a leaving group, followed by reacting Intermediate F2 with an Intermediate of formula R²LG, where R² is as defined above and LG is a leaving group, in a presence of a base. A Buchwald cross coupling reaction of Intermediates F2 or F3 with an amine of formula A2 provides Intermediate F4 where ring $B_1$, n and $R^1$ are as defined above and $PG^1$ is a suitable protecting group. Reduction of the nitro group provides Intermediate F5 which is then cyclized to the corresponding aminobenzimidazole Intermediate F6. Coupling of Intermediate F6 with an acid of formula RCO₂H under standard coupling conditions or with an activated acid of formula RC(O)LG where R is as defined above and LG is a leaving group provides Intermediate F7. Removal of $PG^1$ protecting group provides Intermediate F8. Compounds of Formula I are then obtained by coupling Intermediate F8 with an acid of formula

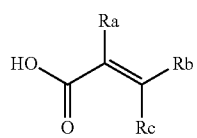

under standard coupling conditions or with an activated acid of formula

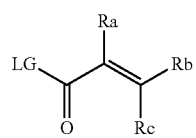

where $R^a$, $R^b$ and $R^c$ are as defined above and LG is a leaving group.

Scheme F

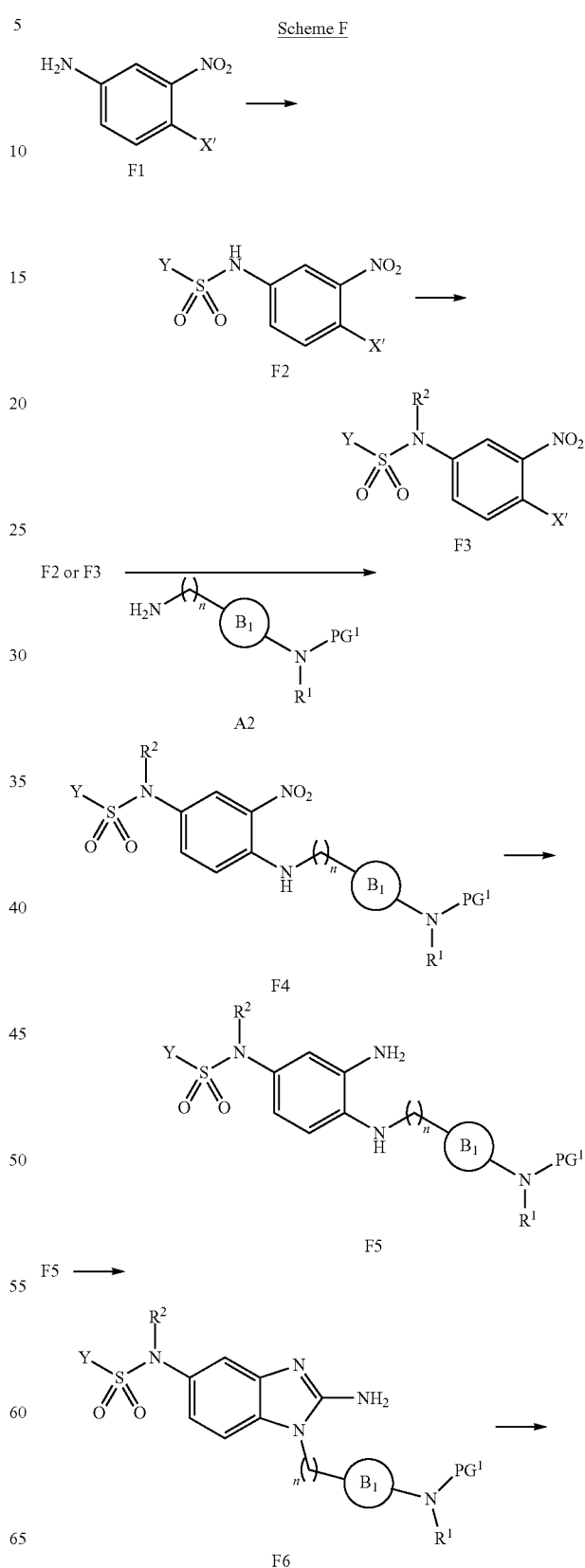

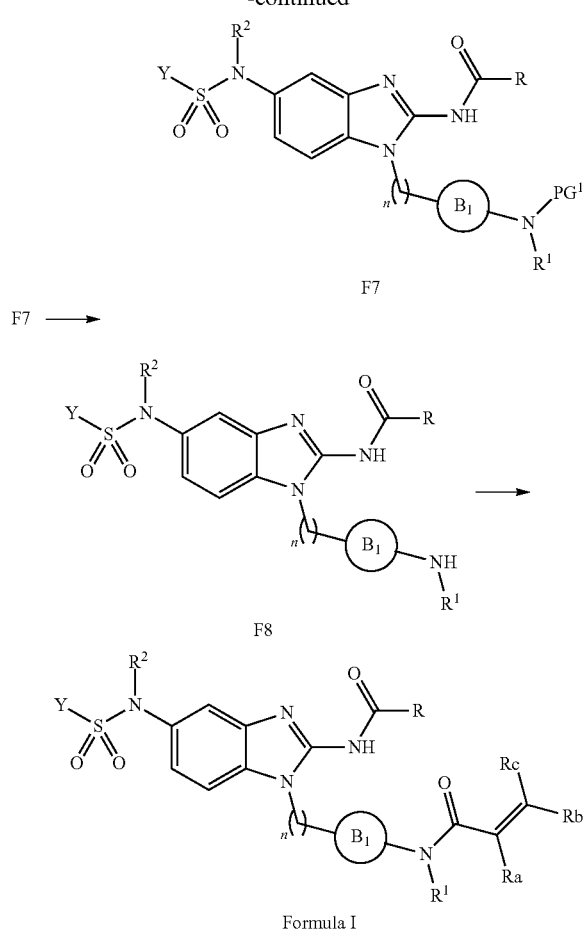

F7

F7 →

F8

Formula I

X' = Br, I

Compounds of Formula I where L-E is selected from

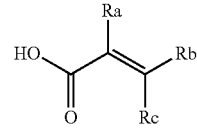

and X—Y is selected from —NR²C(O)—Y are prepared in a similar manner by substituting

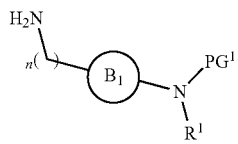

with

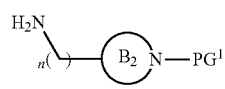

where ring $B_2$, n and $PG^1$ are as defined above.

Compounds of Formula I where L-E is selected from

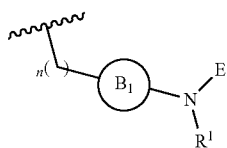

and X—Y is selected from —O—CH₂—Y are prepared as described below:

Intermediate G2 is obtained by reacting commercially available Intermediate G1 with an Intermediate of formula Y—CH₂-LG, where Y is as described above and LG is a leaving group, in a presence of a base. Alternatively, Intermediate G2 is obtained by reacting Intermediate F1 with an Intermediate of formula Y—CH₂—OH under Mitsunobu conditions. A Buchwald cross coupling reaction of Intermediate G2 with an amine of formula A2 provides Intermediate G3 where ring $B_1$, n and $R^1$ are as defined above and $PG^1$ is a suitable protecting group. Reduction of the nitro group provides Intermediate G4 which is then cyclized to the corresponding aminobenzimidazole Intermediate G5. Coupling of Intermediate G5 with an acid of formula RCO₂H under standard coupling conditions or with an activated acid of formula RC(O)LG where R is as defined above and LG is a leaving group provides Intermediate G6. Removal of $PG^1$ protecting group provides Intermediate G7. Compounds of Formula I are obtained by coupling Intermediate G7 with an acid of formula

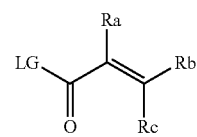

under standard coupling conditions or with an activated acid of formula

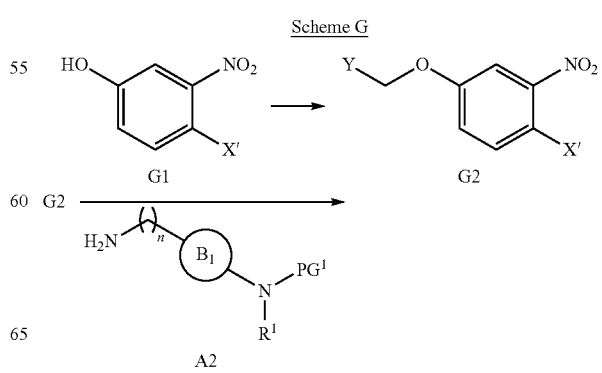

where $R^a$, $R^b$ and $R^c$ are as defined above and LG is a leaving group.

Scheme G

G1 → G2

G2 →

A2

-continued

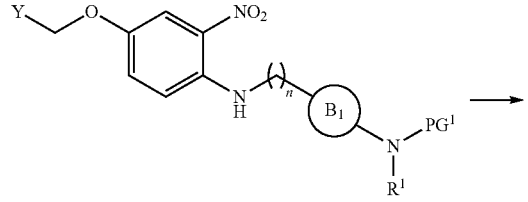

G3

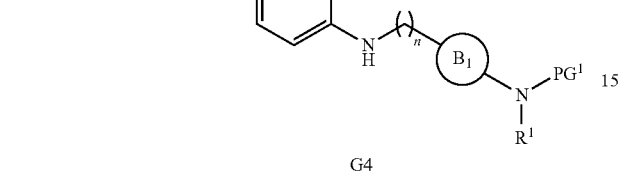

G4

G4 →

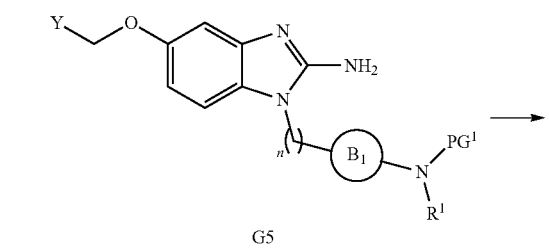

G5

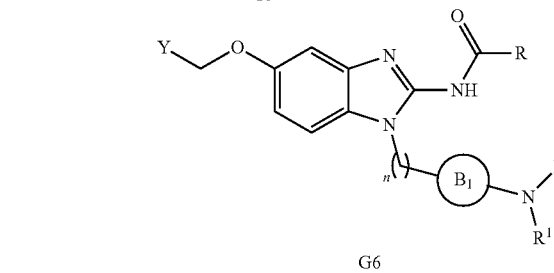

G6

G6 →

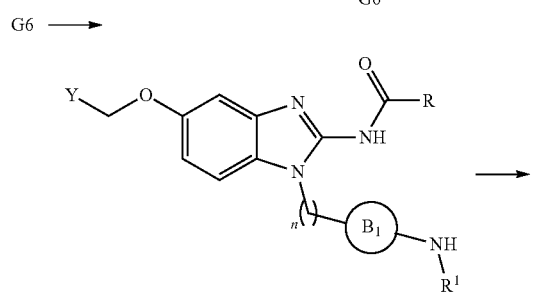

G7

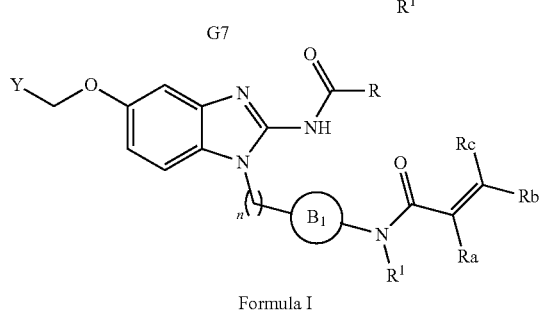

Formula I

X' = Br, I

Compounds of Formula I where L-E is selected from

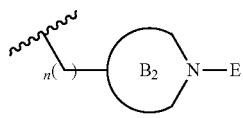

and X—Y is selected from —O—CH$_2$—Y are prepared in a similar manner by substituting

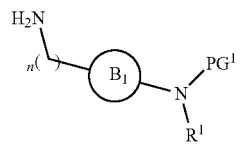

with

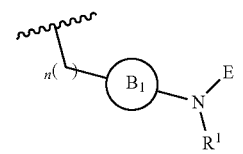

where ring B$_2$, n and PG$^1$ are as defined above.

Compounds of Formula I wherein L-E is selected from and X—Y is selected from —CH$_2$—NR$^3$—Y are prepared as described below:

Compounds of Formula I where R$^3$ is selected from —C(O)R$^4$ as described above are obtained by reacting a compound of Formula I where X—Y is selected from —CH$_2$NH—Y with an acid of formula R$^4$CO$_2$H under standard coupling conditions or with an activated acid of formula R$^4$C(O)LG where R$^4$ is as defined above and LG is a leaving group. Compounds of Formula I where R$^3$ is selected from —SO$_2$R$^4$ as described above are obtained by reacting a compound of Formula I where X—Y is selected from —CH$_2$NH—Y with an Intermediate of formula R$^4$SO$_2$LG where R$^4$ is as defined above and LG is a leaving group. Compounds of Formula I where R$^3$ is selected from —C(O)OR$^4$ as described above are obtained by reacting a compound of Formula I where X—Y is selected from —CH$_2$NH—Y with an Intermediate of formula R$^4$C(O)OLG where R$^4$ is as defined above and LG is a leaving group.

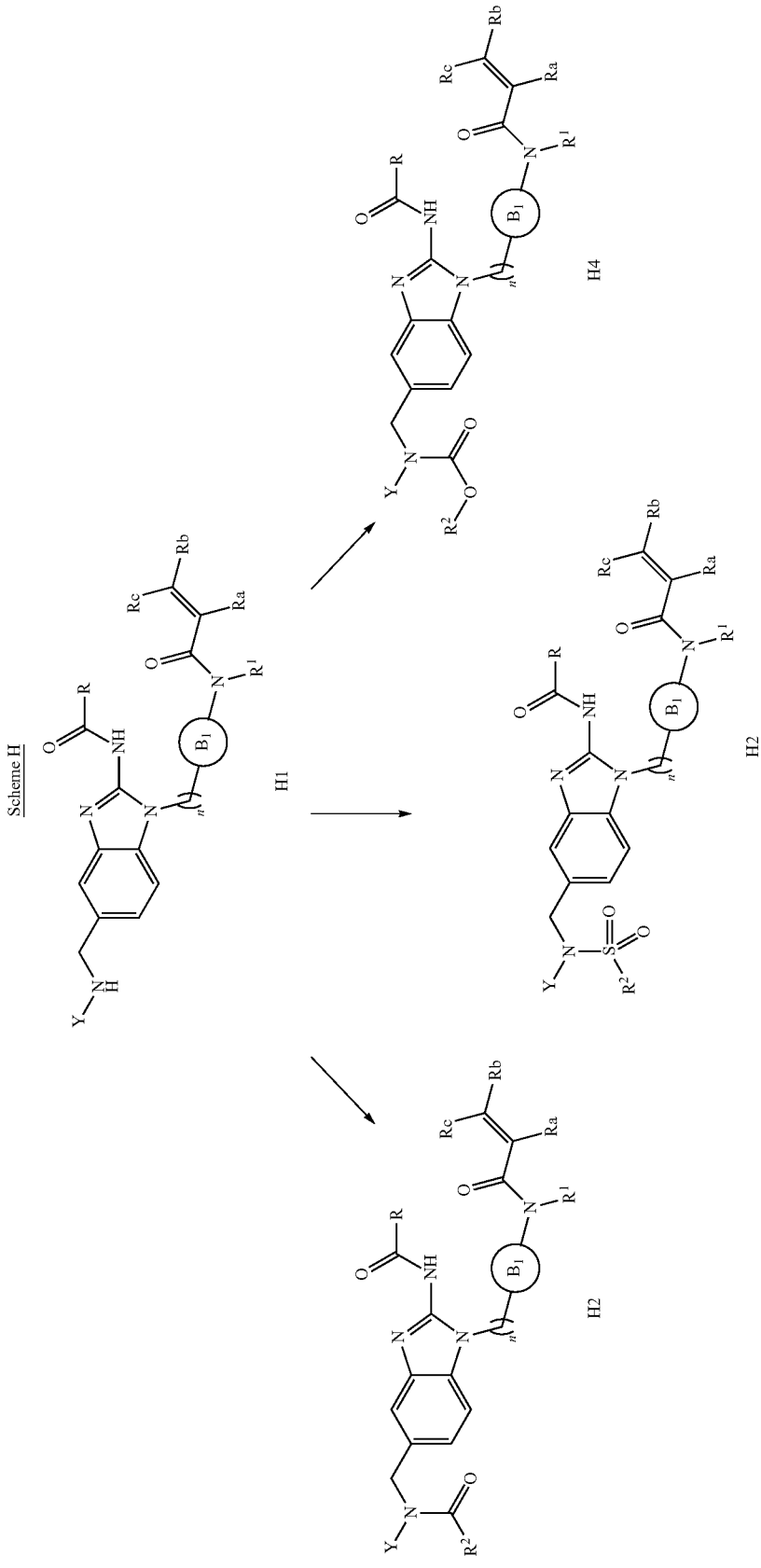

Compounds of Formula I where L is selected from

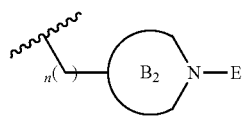

and X—Y is selected from —CH$_2$—NR$^3$—Y are prepared in a similar manner by substituting

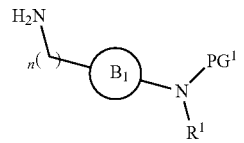

with

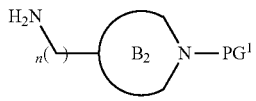

where ring B$_2$, n and PG$^1$ are as defined above.

The following synthetic methods are intended to be representative of the chemistry used to prepare compound of Formula I of the present invention and are not intended to be limiting.

Synthesis of Intermediate 1-h:

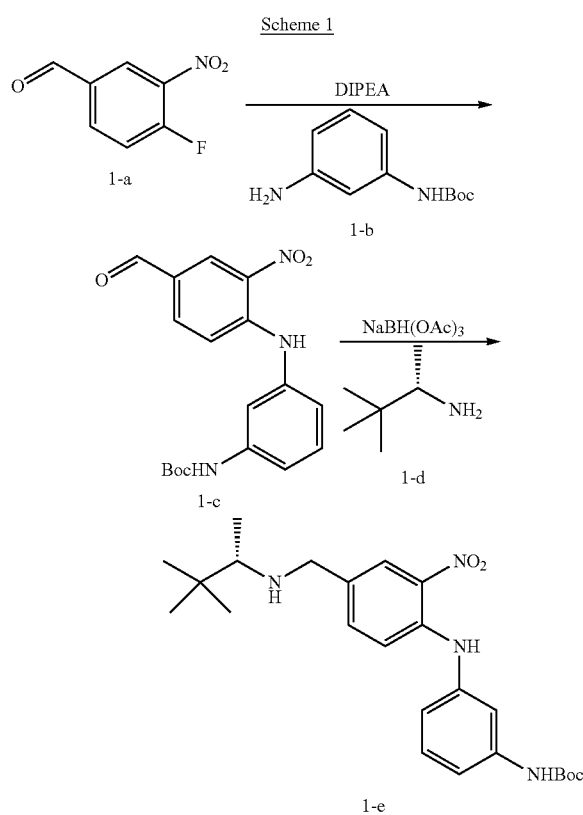

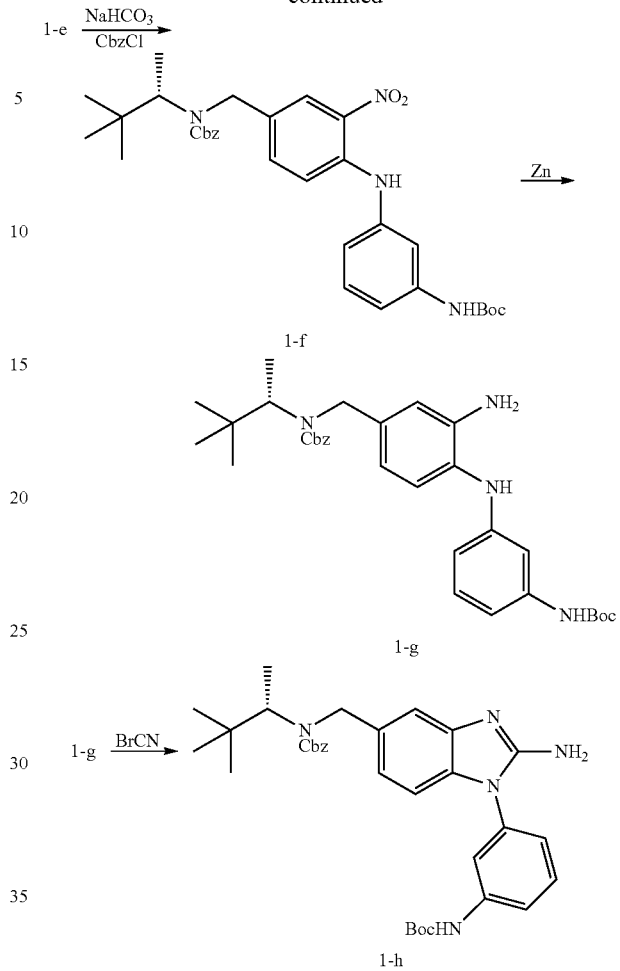

Step 1: Intermediate 1-c

To a solution of 4-fluoro-3-nitrobenzaldehyde 1-a (812 mg, 4.8 mmol) and DIPEA (2.5 ml, 14.4 mmol) in acetonitrile was added dropwise a solution of tert-butyl 3-aminophenylcarbamate 1-b (1.0 g, 4.8 mmol) in acetonitrile. After the addition was completed, the reaction was stirred overnight at room temperature. Volatiles were removed under reduced pressure. A saturated aqueous solution of ammonium chloride and dichloromethane were added to the residue, the organic layer was separated, and the aqueous phase was extracted twice with dichloromethane. The combined organic extracts were washed with brine, dried over MgSO$_4$, filtered and concentrated under reduced pressure. Purification by silica gel chromatography provided Intermediate 1-c as a yellow solid.

Step 2: Intermediate 1-e

To a solution of Intermediate 1-c (1.7 g, 4.7 mmol) and (S)-3,3-dimethylbutan-2-amine 1-e (481 mg, 4.7 mmol) in 1,2-dichloroethane were sequentially added acetic acid (136 μl, 2.4 mmol) and sodium triacetoxyborohydride (1.5 g, 7.1 mmol) and the reaction was stirred at room temperature overnight. A saturated aqueous solution of NaHCO$_3$ and dichloromethane were then added, the organic layer was separated, and the aqueous phase was extracted twice with dichloromethane. The combined organic extracts were washed with brine, dried over MgSO$_4$, filtered and concentrated under reduced pressure to provide Intermediate 1-e as a yellow solid.

Step 3: Intermediate 1-f

To a solution of Intermediate 1-e (2.0 g, 4.5 mmol) in dichloromethane were sequentially added sodium bicarbonate (380 mg) in water (9 ml) and benzyl chloroformate (968 µl, 6.8 mmol) and the reaction was then stirred for 2 hours at room temperature. A saturated aqueous solution of ammonium chloride and diethyl ether were added to the residue, the organic layer was separated, and the aqueous phase was extracted twice with diethyl ether. The combined organic extracts were washed with brine, dried over $MgSO_4$, filtered and concentrated under reduced pressure. Purification by silica gel chromatography provided Intermediate 1-f as a beige oil.

Step 4: Intermediate 1-g

To a solution of Intermediate 1-f (1.5 g, 2.6 mmol) in MeOH (9.7 ml) was added a saturated aqueous solution of ammonium chloride (3.2 ml) and zinc dust (850 mg, 13.0 mmol) portionwise. The reaction was then stirred at 50° C. until completion, then cooled to room temperature and filtered over celite. The filtrate was concentrated under reduced pressure. A saturated aqueous solution of $NaHCO_3$ and ethyl acetate were added to the residue, the organic layer was separated, washed with brine, dried over $MgSO_4$, filtered and concentrated under reduced pressure to provide Intermediate 1-g as a purple solid.

Step 5: Intermediate 1-h

To a solution of Intermediate 1-g (1.3 g, 2.4 mmol) in EtOH (24.0 ml) was added cyanogen bromide (302 mg, 2.8 mmol) and the reaction was stirred for 4 hours at room temperature. A saturated aqueous solution of ammonium chloride and ethyl acetate were then added, the organic layer was separated, and the aqueous phase was extracted twice with ethyl acetate. The combined organic extracts were washed with brine, dried over $MgSO_4$, filtered and concentrated under reduced pressure. Purification by silica gel chromatography provided Intermediate 1-h as a purple solid.

Synthesis of Intermediates 2-c:

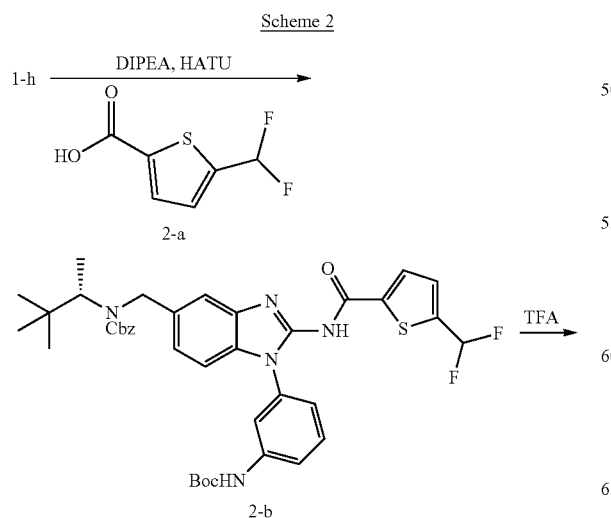

Scheme 2

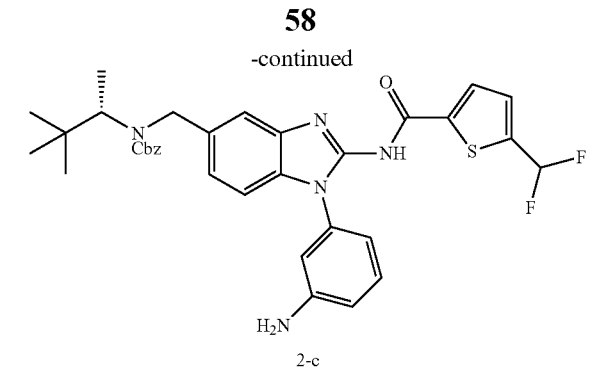

2-c

Step 1: Intermediate 2-b

To a solution of Intermediate 5-(difluoromethyl)thiophene-2-carboxylic acid 2-a (150 mg, 0.8 mmol) in DMF (3.5 ml) was added HATU (346 mg, 0.9 mmol) and after stirring for 30 minutes a solution of Intermediate 1-h (400 mg, 0.7 mmol) and DIPEA (367 µl, 2.1 mmol) in DMF was added dropwise. The reaction was then stirred at room temperature for 4 hours. A saturated aqueous solution of ammonium chloride and ethyl acetate were then added, the organic layer was separated, washed with a saturated aqueous solution of $NaHCO_3$ and brine, dried over $MgSO_4$, filtered and concentrated under reduced pressure. Purification by silica gel chromatography provided Intermediate 2-b as a purple solid.

Step 2: Intermediate 2-c

To a solution of Intermediate 2-b (300 mg, 0.4 mmol) in dichloromethane (5 ml) was added TFA (2.5 ml, 32.7 mmol) at 0° C. and the solution was stirred at room temperature until completion. Volatiles were removed under reduced pressure to provide Intermediate 2-c.TFA as a white solid.

Synthesis of Compound 2:

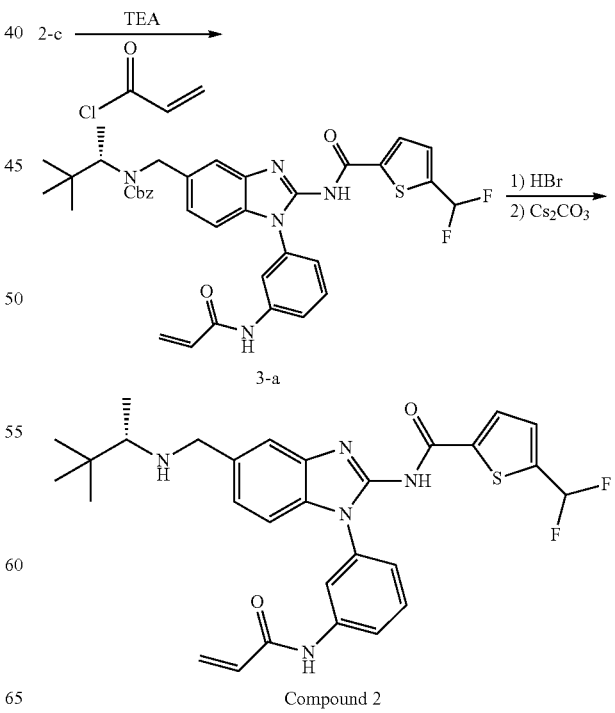

Step 1: Intermediate 3-a

To a solution of Intermediate 2-c.TFA (300 mg, 0.4 mmol) in THF (2 mL) cooled to −78° C. were sequentially added DIPEA (348 μl, 2.0 mmol) and acryloyl chloride (49 μL, 0.6 mmol) and the solution was stirred at −78° C. until completion. A saturated aqueous solution of ammonium chloride and ethyl acetate were then added, the organic layer was separated, and the aqueous phase was extracted twice with ethyl acetate. The combined organic extracts were washed with brine, dried over MgSO₄, filtered and concentrated under reduced pressure to provide Intermediate 3-a as a white foam.

Step 2: Compound 2

To a solution of Intermediate 3-a (250 mg, 0.3 mmol) in DCM (1 ml) was added a solution of 33% HBr in AcOH (990 μl, 5.4 mmol) at 0° C. and the solution was then stirred at room temperature until completion. Diethyl ether was added and the precipitate was filtered off and washed twice with diethyl ether. The solid was dissolved in THF and Cs₂CO₃ (500 mg) was added. The mixture was refluxed for 1 hour, then cooled to room temperature, filtered and concentrated under reduced pressure. Purification by silica gel chromatography provided Compound 2 as a white solid.

Compounds 7, 8, 9, 10, 11, 12, 13, 15, 16, 17, 19, 20, 24, 25, 26 and 82 were prepared in a similar manner to Compound 2 by replacing 5-(difluoromethyl)thiophene-2-carboxylic acid with 3-fluorobenzoic acid, 3-methoxybenzoic acid, 3-cyanobenzoic acid, 4-chlorobenzoic acid, 4-cyanobenzoic acid, thiazole-2-carboxylic acid, thiophene-2-carboxylic acid, 3-chlorobenzoic acid, isonicotinic acid, thiazole-5-carboxyllic acid, nicotinic acid, 4-fluorobenzoic acid, 4-methoxy benzoic acid, 5-(oxazol-5-yl)thiophene-2-carboxylic acid, 3-(benzyloxy)benzoic acid and 2-isopropytthiazole-5-carboxilic acid respectively.

Compounds 4, 5, 33 and 34 were prepared in a similar manner to Compound 2 by replacing tert-butyl 3-aminophenylcarbamate 1-b with tert-butyl 4-aminophenylcarbamate, tert-butyl 3-aminophenyl(methyl)carbamate, tert-butyl 3-amino-4-fluorophenylcarbamate and tert-butyl 5-amino-2-fluorophenylcarbamate respectively, Synthesis of Intermediate 4-f:

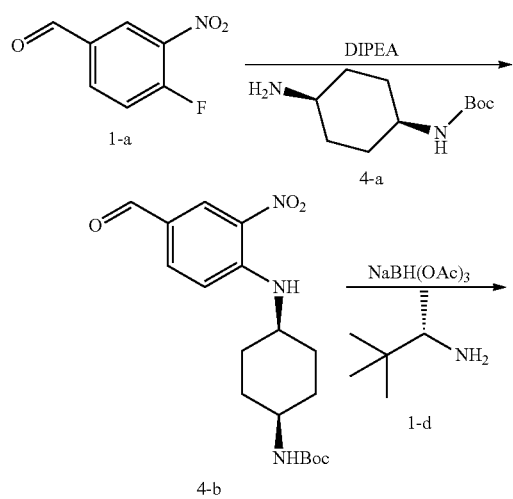

Scheme 4

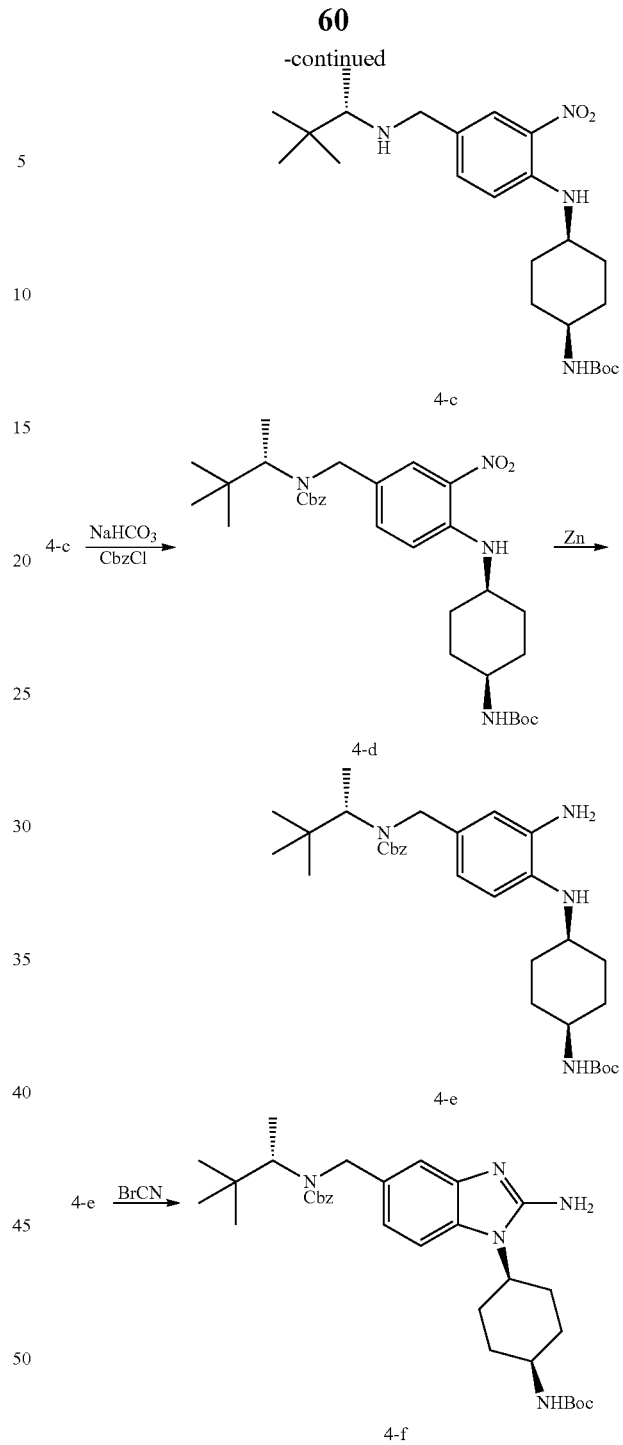

Step 1: Intermediate 4-b

To a solution of 4-fluoro-3-nitrobenzaldehyde 1-a (1.5 g, 9.3 mmol) and DIPEA (4.9 ml, 28.0 mmol) in acetonitrile was added dropwise a solution of Intermediate 4-a (2.0 g, 9.3 mmol) in acetonitrile. After the addition was completed, the reaction was stirred overnight at room temperature. Volatiles were removed under reduced pressure. A saturated aqueous solution of ammonium chloride and dichloromethane were added to the residue, the organic layer was separated, and the aqueous phase was extracted twice with dichloromethane. The combined organic extracts were washed with brine, dried over MgSO₄, filtered and concentrated under reduced pressure. Purification by silica gel chromatography provided Intermediate 4-b as a yellow solid.

Step 2: Intermediate 4-c

To a solution of Intermediate 4-b (2.3 g, 6.3 mmol) and (S)-3,3-dimethylbutan-2-amine 1-d (640 mg, 6.3 mmol) in 1,2-dichloroethane were sequentially added acetic acid (181 µl, 2.4 mmol) and sodium triacetoxyborohydride (2.0 g, 9.5 mmol) and the reaction was stirred at room temperature overnight A saturated aqueous solution of NaHCO$_3$ and dichloromethane were then added, the organic layer was separated, and the aqueous phase was extracted twice with dichloromethane. The combined organic extracts were washed with brine, dried over MgSO$_4$, filtered and concentrated under reduced pressure to provide Intermediate 4-c as an orange solid.

Step 3: Intermediate 4-d

To a solution of Intermediate 4-c (2.2 g, 5.0 mmol) in dichloromethane were sequentially added sodium bicarbonate (420 mg) in water (10 ml) and benzyl chloroformate (1.0 ml, 7.5 mmol) and the reaction was then stirred overnight at room temperature. Volatiles were removed under reduced pressure. A saturated aqueous solution of ammonium chloride and ethyl acetate were added to the residue, the organic layer was separated, and the aqueous phase was extracted twice with ethyl acetate. The combined organic extracts were washed with brine, dried over MgSO$_4$, filtered and concentrated under reduced pressure. Purification by silica gel chromatography provided Intermediate 4-d as a beige oil.

Step 4: Intermediate 4-e

To a solution of Intermediate 4-d (1.7 g, 2.9 mmol) in MeOH (9.7 ml) was added a saturated aqueous solution of ammonium chloride (4.8 ml) and zinc dust (954 mg, 13.0 mmol) portion wise. The reaction was then stirred at 50° C. until completion, then cooled to room temperature and filtered over celite. The filtrate was concentrated under reduced pressure. A saturated aqueous solution of NaHCO$_3$ and ethyl acetate were added to the residue, the organic layer was separated, washed with brine, dried over MgSO$_4$, filtered and concentrated under reduced pressure. Diethyl ether was added to the residue; a precipitate formed and was collected by filtration to provide Intermediate 4-e as a purple solid.

Step 5: Intermediate 4-f

To a solution of Intermediate 4-e (1.5 g, 2.7 mmol) in EtOH (24 ml) was added cyanogen bromide (345 mg, 3.2 mmol) and the reaction was stirred for 4 hours at room temperature. A saturated aqueous solution of ammonium chloride and ethyl acetate were then added, the organic layer was separated, and the aqueous phase was extracted twice with ethyl acetate. The combined organic extracts were washed with brine, dried over MgSO$_4$, filtered and concentrated under reduced pressure. Diethyl ether was added to the residue; a precipitate formed and was collected by filtration to provide Intermediate 4-f as a purple solid.

Synthesis of Intermediate 5-b:

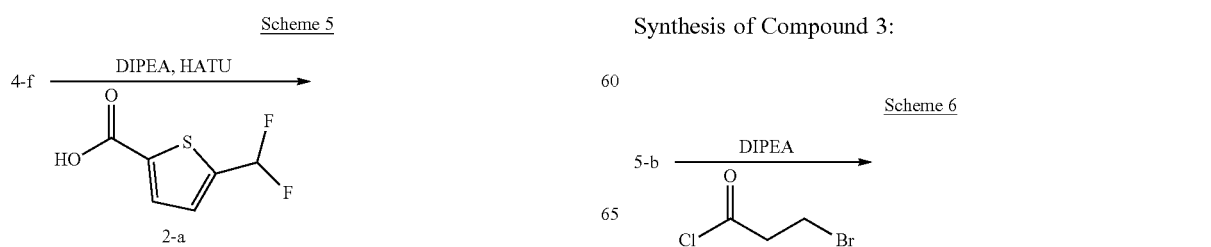

Scheme 5

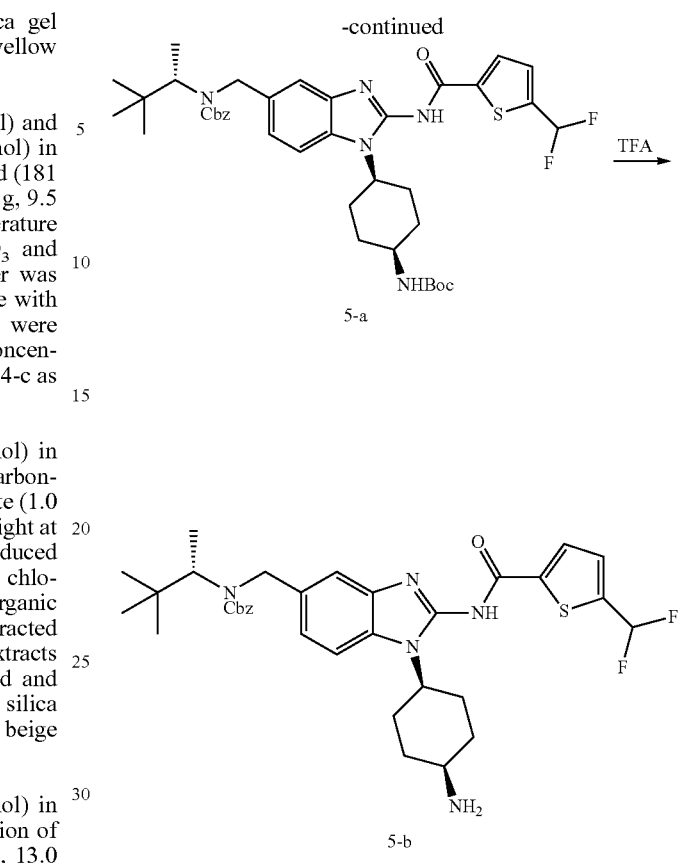

Step 1: Intermediate 5-a

To a solution of 5-(difluoromethyl)thiophene-2-carboxylic acid 2-a (351 mg, 0.6 mmol) in DMF (3.0 ml) cooled to 0° C. was added HATU (301 mg, 0.8 mmol) and after stirring for 30 minutes a solution of Intermediate 4-f (130 mg, 0.7 mmol) and DIPEA (319 µl, 2.1 mmol) in DMF was added dropwise. The reaction was then stirred at room temperature for 4 hours. A saturated aqueous solution of ammonium chloride and ethyl acetate were then added, the organic layer was separated, washed with a saturated aqueous solution of NaHCO$_3$ and brine, dried over MgSO$_4$, filtered and concentrated under reduced pressure. Purification by silica gel chromatography provided Intermediate 5-a as a purple solid.

Step 2: Intermediate 5-b

To a solution of Intermediate 5-a (300 mg, 0.4 mmol) in dichloromethane (5 ml) was added TFA (2.5 ml, 32.7 mmol) at 0° C. and the solution was stirred at room temperature until completion. Volatiles were removed under reduced pressure to provide Intermediate 5-b-TFA as an off-white solid.

Synthesis of Compound 3:

Scheme 6

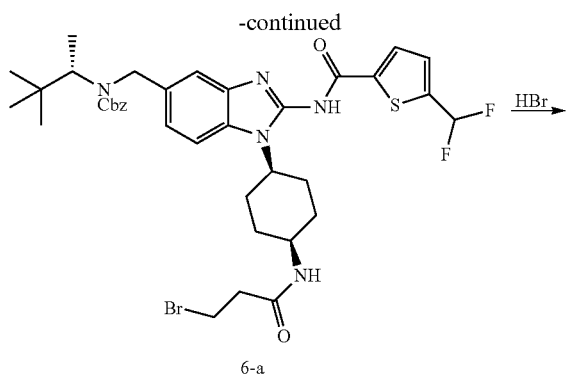

Step 3: Compound 3

To a solution of Intermediate 6-b (260 mg, 0.4 mmol) in THF was added DIPEA (1.0 ml, 5.7 mmol) and the reaction was stirred at room temperature overnight. Volatiles were removed under reduced pressure. Purification by silica gel chromatography provided Compound 3 as a white solid.

Compounds 54, 55, 67 and 71 were prepared in a similar manner to Compound 3 by replacing 5-(difluoromethyl) thiophene-2-carboxylic acid with 4-cyanobenzoic acid, nicotinic acid, isothiazole-5-carboxylic acid and 5-(oxazol-5-yl)thiophene-2-carboxylic acid respectively.

Compounds 1, 6, 18, 58, 62, 68 and 81 were prepared in a similar manner to Compound 3 by replacing

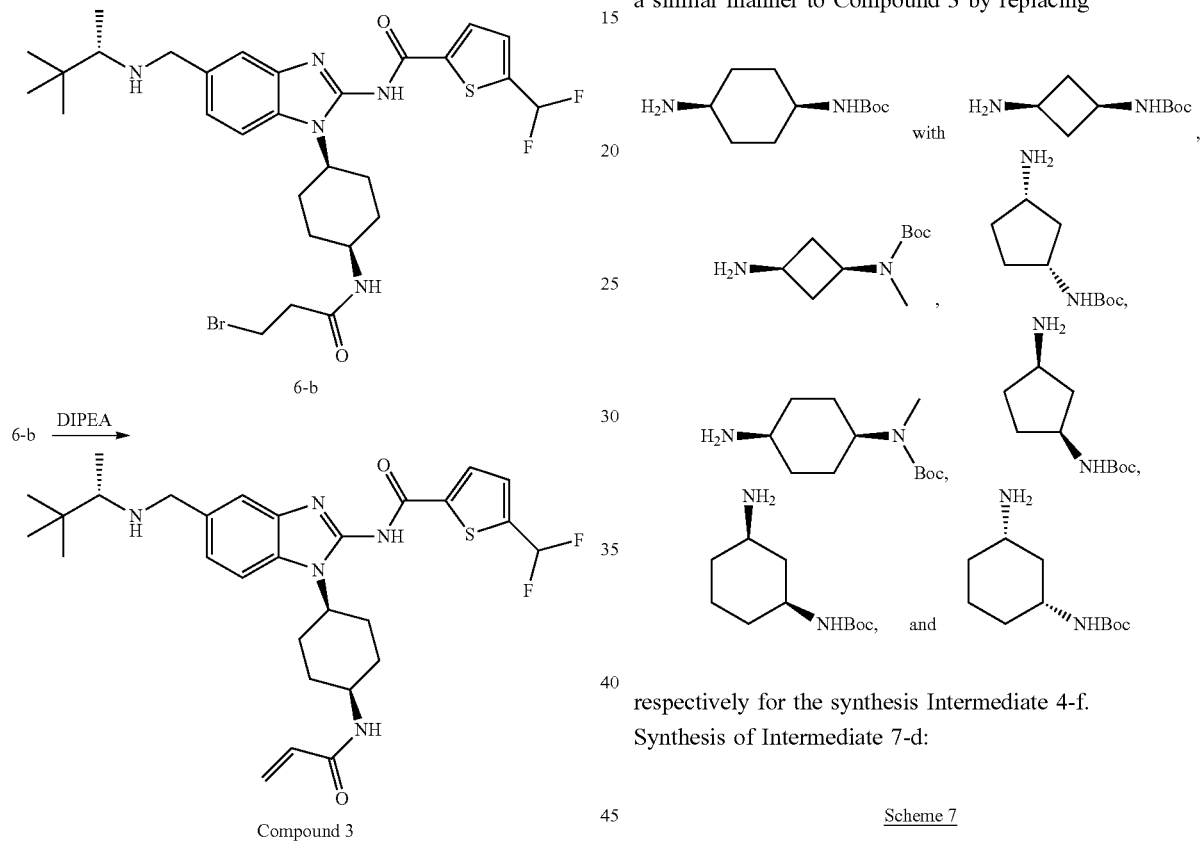

respectively for the synthesis Intermediate 4-f.

Synthesis of Intermediate 7-d:

Step 1: Intermediate 6-a

To a solution of Intermediate 5-b.TFA (310 mg, 0.4 mmol) in THF (2 mL) cooled to −78° C. were sequentially added DIPEA (700 µl, 4.1 mmol) and 3-bromopropanoyl chloride (62 µL, 0.6 mmol) and the solution was stirred at −78° C. until completion. A saturated aqueous solution of ammonium chloride and ethyl acetate were then added, the organic layer was separated, and the aqueous phase was extracted twice with ethyl acetate. The combined organic extracts were washed with brine, dried over MgSO$_4$, filtered and concentrated under reduced pressure to provide Intermediate 6-a as a white foam.

Step 2: Intermediate 6-b

To a solution of Intermediate 6-a (320 mg, 0.4 mmol) in dichloromethane (1.5 ml) was added a solution of 33% HBr in AcOH (1.1 ml, 6.2 mmol) at 0° C. and the solution was then stirred at room temperature until completion. Diethyl ether was added; a precipitate formed and was collected by filtration, washed twice with diethyl ether and dried under vacuum to provide Intermediate 6-b as a white solid.

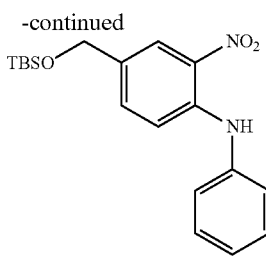

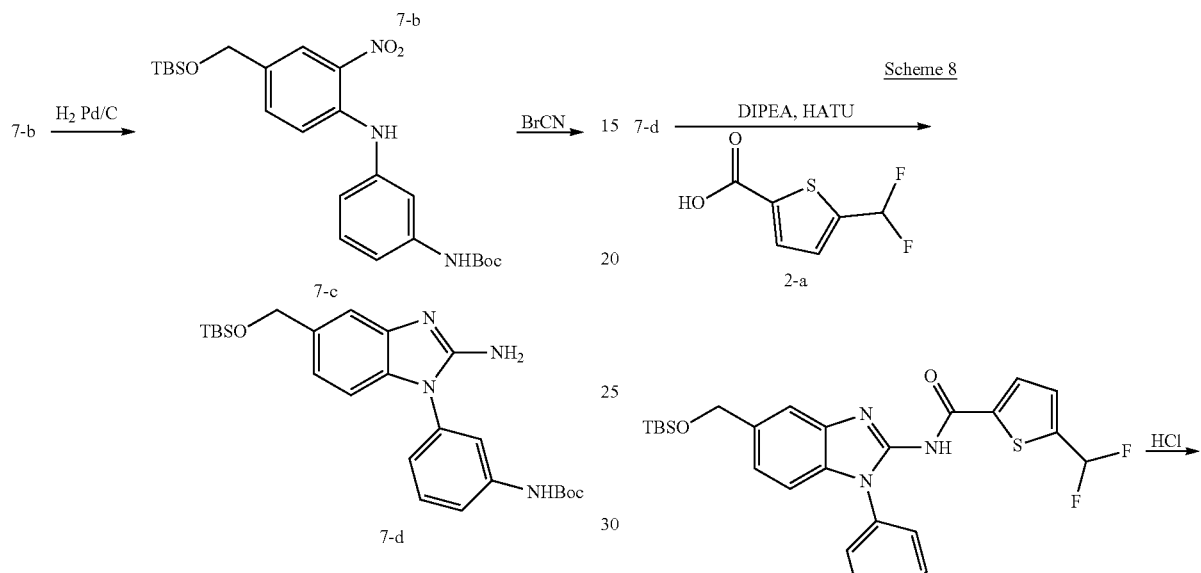

Step 1: Intermediate 7-a

To a solution of Intermediate 1-c (5.0 g, 14.0 mmol) in ethanol (200 ml) was added portion wise sodium borohydride (794 mg, 21.0 mmol) and the reaction was stirred at room temperature for 1 hour. A saturated aqueous solution of NaHCO₃ was slowly added and after stirring for 15 minutes volatiles were removed under reduced pressure. Ethyl acetate was added, the organic layer was separated, washed with a saturated aqueous solution of NaHCO₃ and brine, dried over MgSO₄, filtered and concentrated under reduced pressure to provide Intermediate 7-a as a beige foam.

Step 2: Intermediate 7-b

To a solution of Intermediate 7-a (5.0 g, 13.9 mmol) in dichloromethane (143 ml) cooled to 0° C. were sequentially added imidazole (1.9 g, 29.2 mmol) and tert-butylchlorodimethylsilane (2.2 g, 14.6 mmol) portion wise. The reaction was then warmed to room temperature and stirred overnight. A saturated aqueous solution of ammonium chloride and ethyl acetate were added, the organic layer was separated, washed with a saturated aqueous solution of ammonium chloride and brine, dried over MgSO₄, filtered and concentrated under reduced pressure to provide Intermediate 7-b as a beige oil.

Step 3: Intermediate 7-c

To a solution of Intermediate 7-b (5.0 g, 10.6 mmol) in methanol and stirred under nitrogen was added 10% Pd/C (225 mg, 1.1 mmol). The reaction mixture was purged with H₂ and stirred for 24 hours under H₂. The reaction was then filtered through celite and the filtrate was concentrated under reduced pressure to provide Intermediate 7-c as a beige solid.

Step 4: Intermediate 7-d

To a solution of Intermediate 7-c (4.5 g, 10.1 mmol) in EtOH (51 ml) was added cyanogen bromide (1.3 g, 12.2 mmol) and the reaction was stirred for 2 hours at room temperature. Volatiles were removed under reduced pressure. A saturated aqueous solution of ammonium chloride and ethyl acetate were then added to the residue, the organic layer was separated, washed with a saturated aqueous solution of NaHCO₃ and brine, dried over MgSO₄, filtered and concentrated under reduced pressure to provide Intermediate 7-d as a beige foam.

Synthesis of Compound 85:

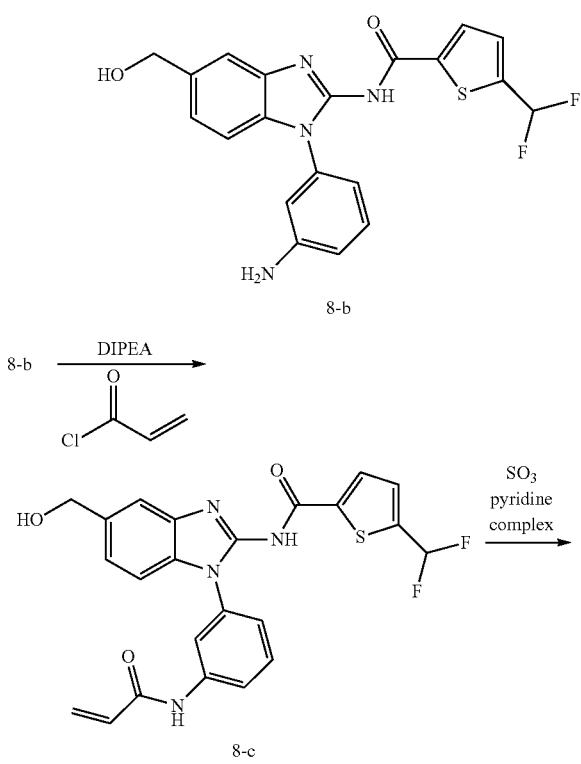

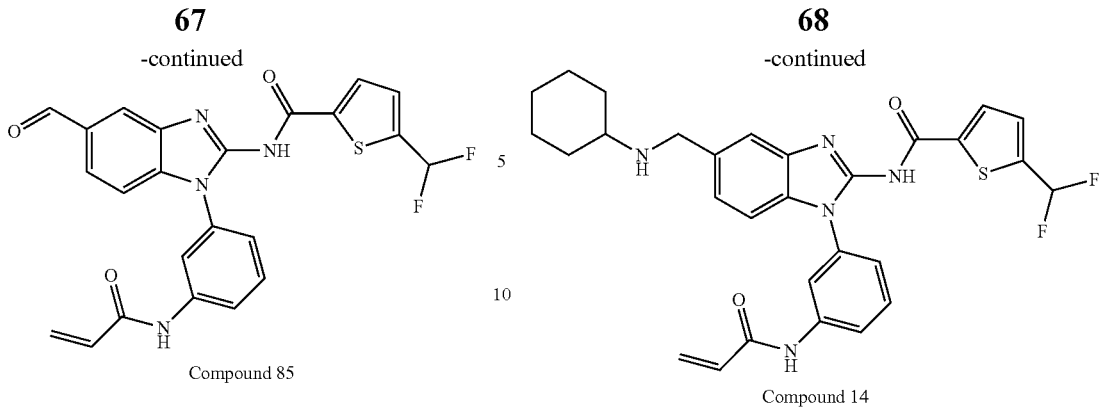

Compound 85

Compound 14

Step 1: Intermediate 8-a

To a solution of 5-(difluoromethyl)thiophene-2-carboxylic acid 2-a (1.2 g, 7.1 mmol) in DMF (32.0 ml) cooled to 0° C. was added HATU (3.2 g, 8.3 mmol) and after stirring for 30 minutes a solution of Intermediate 7-d (3.0 mg, 6.4 mmol) and DIPEA (3.3 ml, 19.2 mmol) in DMF was added dropwise. The reaction was then stirred at room temperature overnight A saturated aqueous solution of ammonium chloride and ethyl acetate were then added, the organic layer was separated, washed with a saturated aqueous solution of $NaHCO_3$ and brine, dried over $MgSO_4$, filtered and concentrated under reduced pressure. Purification by silica gel chromatography provided Intermediate 8-a as a purple solid.

Step 2: Intermediate 8-b

To a solution of Intermediate 8-a (2.5 g, 3.9 mmol) in MeOH (5 ml) was added 4N HCl in 1,4-dioxane (50.0 ml, 1646.0 mmol) and the solution was stirred at room temperature overnight. Volatiles were removed under reduced pressure and diethyl ether was added to the residue. A precipitate formed and was collected by filtration, dried under vacuum to provide Intermediate 8-b.HCl as a purple solid.

Step 3: Intermediate 8-c

To a solution of Intermediate 8-b.HCl (77 mg, 0.2 mmol) in tetrahydrofuran (1.8 ml) cooled to −78° C. were sequentially added DIPEA (323 μl, 1.8 mmol) and acryloyl chloride (15 μl, 0.2 mmol) and the reaction was stirred at −78° C. for 2 hours. Water (20 mL) and ethyl acetate (20 mL) were added, the organic layer was separated, washed with a saturated aqueous solution of $NaHCO_3$ and brine, dried over anhydrous $MgSO_4$, filtered and concentrated under reduced pressure to provide Intermediate 8-c as a beige solid.

Step 4: Compound 85

To a solution of Intermediate 8-c (1.8 g, 3.8 mmol) in THF (15 ml) and DMSO (10.0 ml) cooled to 0° C. were sequentially added DIPEA (2.7 ml, 15.4 mmol) and a solution of $SO_3$ pyridine complex (1.8 g, 11.5 mmol) in DMSO (5 mL). The mixture was stirred at 0° C. until completion. Volatiles were removed under reduced pressure, water was added, a precipitate formed and was collected by filtration, washed with water and dried under vacuum to provide Intermediate 8-d as a beige solid.

Synthesis of Compound 14:

Scheme 8

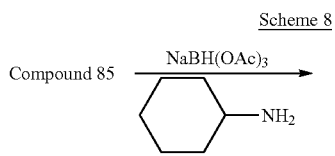

To a solution of Compound 85 (40 mg, 0.09 mmol) and cyclohexylamine (10.0 μl, 0.09 mmol) in dichloroethane (700 μl) and THF (70 μl) were sequentially added acetic acid (2 μl, 0.04 mmol) and sodium triacetoxyborohydride (27 mg, 0.13 mmol) and the reaction was stirred at room temperature overnight. Volatiles were removed under reduced pressure. Purification by silica gel chromatography provided Compound 14 as a white solid.

Compounds 21, 22, 23, 29, 30, 31, 35, 39, 40, 46, 47, 59 and 66 were prepared in a similar manner to Compound 14 by replacing cyclohexylamine with (S)-butan-2-amine, (R)-2-amino-3,3-dimethylbutan-1-ol, 2,2-dimethylpropan-1-amine, 3-amino-2,2-dimethylpropan-1-ol, (R)-3,3-dimethylbutan-2-amine, trans 4-aminocyclohexanol, cis 4-aminocyclohexanol, 3-aminopropan-1-ol, ethanamine, 2-(2-methoxyethoxy)ethanamine, (S)-2-amino-3,3-dimethylbutan-1-ol, 2-(piperazin-1-yl)ethanol and N-(3-(2-(3-aminopropoxy)ethoxy)propyl)acetamide respectively.

Synthesis of Compound 32:

Scheme 9

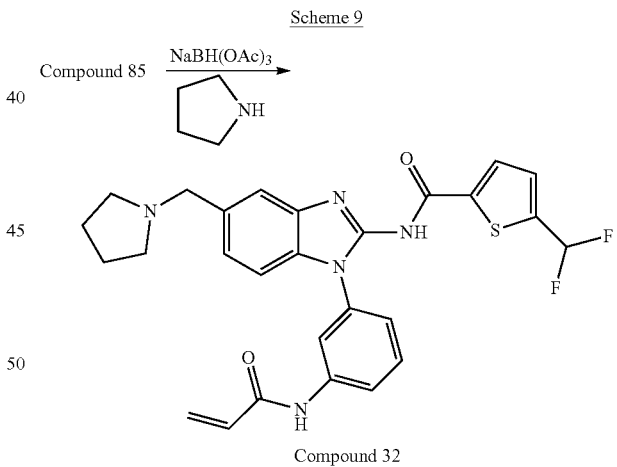

Compound 32

To a solution of Compound 85 (40 mg, 0.09 mmol) and pyrrolidine (6.1 mg, 0.09 mmol) in THF (2.0 ml) was added acetic acid (2 μl, 0.04 mmol) and sodium triacetoxyborohydride (27 mg, 0.13 mmol) and the reaction was stirred at room temperature overnight. Volatiles were removed under reduced pressure. Purification by silica gel chromatography provided Compound 32 as a white solid.

Compounds 44, 45, 50 and 61 were prepared in a similar manner to Compound 32 by replacing pyrrolidine with (R)-pyrrolidin-2-ylmethanol, (S)-pyrrolidin-2-ylmethanol, morpholine and (2S,6R)-2,6-dimethylmorpholine respectively.

69

Synthesis of Intermediate 10-d:

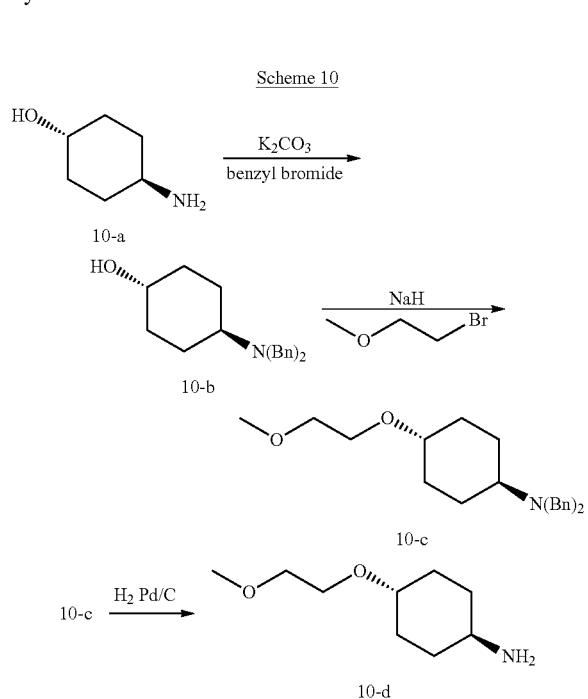

Step 1: Intermediate 10-b

To a solution of trans 4-aminocyclohexanol 10-a (1 g, 8.7 mmol) in acetonitrile (43.4 ml) were sequentially added potassium carbonate (6.0 g, 43.4 mmol) and benzyl bromide (2.06 ml, 17.4 mmol) dropwise. The reaction was stirred at room temperature overnight and then filtered. Volatiles were removed under reduced pressure to provide Intermediate 10-b as a beige oil.

Step 2: Intermediate 10-c

To a solution of Intermediate 10-b (2.5 g, 8.5 mmol) and 1-bromo-2-methoxyethane (3.5 g, 25.4 mmol) in DMPU (8.5 ml) was slowly added NaH (60% dispersion in mineral oil, 846 mg, 21.2 mmol), and the reaction was then stirred at room temperature for 18 hours. Water and ethyl acetate were added; the organic layer was separated, washed with a saturated aqueous solution of $NaHCO_3$ and brine, dried over anhydrous $MgSO_4$, filtered and concentrated under reduced pressure. Purification by silica gel chromatography provided Intermediate 10-c as beige oil.

Step 3: Intermediate 10-d

To a solution of Intermediate 10-c (2.5 g, 7.1 mmol) in methanol and stirred under nitrogen was added 10% Pd/C (200 mg, 0.9 mmol). The reaction mixture was purged with $H_2$ and stirred for 1 day under 60 psi of $H_2$. The reaction was then filtered through celite and the filtrate was concentrated under reduced pressure to provide Intermediate 10-d as a white foam.

Synthesis of Compound 51:

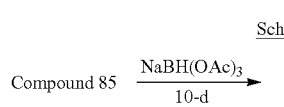

70

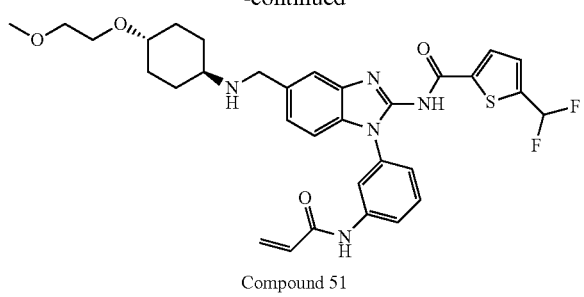

Compound 51

To a solution of Compound 85 (50 mg, 0.11 mmol) and Intermediate 10-d (28 mg, 0.16 mmol) in THF (1 ml) and acetonitrile (1 ml) was added sodium triacetoxyborohydride (34 mg, 0.16 mmol) and the reaction was stirred at room temperature overnight. Volatiles were removed under reduced pressure. Purification by silica gel chromatography provided Compound 51 as a white solid.

Compounds 52 and 60 were prepared in a similar manner to Compound 51 by replacing trans 4-aminocyclohexanol with (R)-2-amino-3,3-dimethylbutan-1-ol and cis 4-aminocyclohexanol respectively for the synthesis of Intermediate 10-d.

Synthesis of Compound 41:

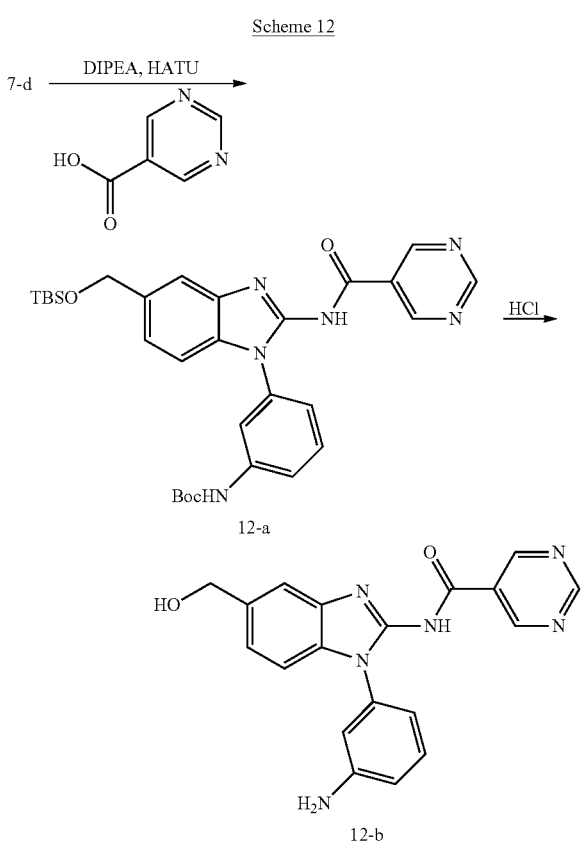

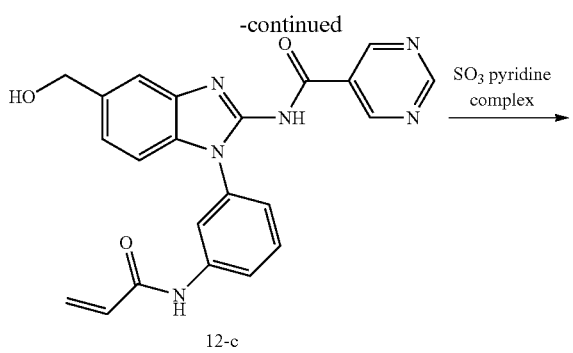

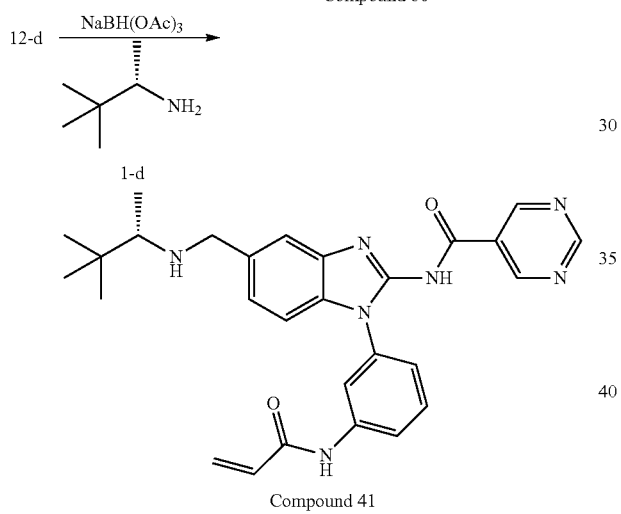

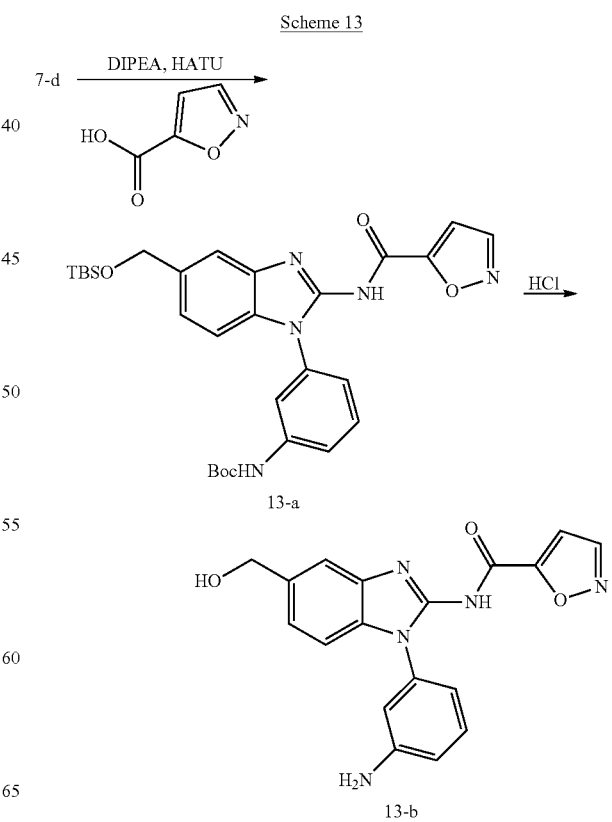

were sequentially added DIPEA (163 µl, 0.94 mmol) and acryloyl chloride (8 µL, 0.09 mmol) and the solution was stirred at −78° C. until completion. Volatiles were removed under reduced pressure, water was added to the residue, a precipitate formed and was collected by filtration, washed with water and dried under vacuum to provide Intermediate 12-c as a beige solid.

Step 4: Compound 86

To a solution of Intermediate 12-c (40 mg, 0.09 mmol) in THF (1.5 ml) and DMSO (1.5 ml) cooled to 0° C. were sequentially added DIPEA (67 µl, 0.38 mmol) and a solution of $SO_3$ pyridine complex (46 mg, 0.29 mmol) in DMSO (1 mL). The mixture was then stirred at room temperature overnight. Volatiles were removed under reduced pressure, water was added, a precipitate formed and was collected by filtration, washed with water and dried under vacuum to provide Compound 86 as a beige solid.

Step 5: Compound 41

To a solution of Compound 86 (40 mg, 0.09 mmol) and (S)-3,3-dimethylbutan-2-amine 1-d (18 µl, 0.14 mmol) in MeOH (2 ml) and dichloromethane (500 µl) were sequentially added acetic acid (2.8 µl, 0.048 mmol) and sodium triacetoxyborohydride (31 mg, 0.14 mmol) and the reaction was stirred at room temperature overnight. Volatiles were removed under reduced pressure. Purification by silica gel chromatography provided Compound 41 as a white solid.

Compounds 27, 28, 37, 38, 42, 43 and 49 were prepared in a similar manner to Compound 41 by replacing pyrimidine-5-carboxylic acid with picolinic acid, 1-methyl-1H-pyrazole-5-carboxylic acid, 4-(benzyloxy)benzoic acid, isoxazole-5-carboxylic acid, oxazole-5-carboxylic acid, isothiazole-5-carboxylic acid and 1-methyl-1H-pyrazole-4-carboxylic acid respectively.

Synthesis of Compound 87:

Step 1: Intermediate 12-a

To a solution of pyrimidine-5-carboxylic acid (53 mg, 0.4 mmol) in DMF cooled to 0° C. was added HATU (211 mg, 0.5 mmol) and after stirring for 30 minutes a solution of Intermediate 7-d (200 mg, 0.4 mmol) and DIPEA (224 µl, 1.3 mmol) in DMF was added dropwise. The reaction was then stirred at room temperature for 3 days. A saturated aqueous solution of ammonium chloride and ethyl acetate were then added, the organic layer was separated, washed with a saturated aqueous solution of $NaHCO_3$ and brine, dried over anhydrous $MgSO_4$, filtered and concentrated under reduced pressure. Purification by silica gel chromatography provided Intermediate 12-a as a purple solid.

Step 2: Intermediate 12-b

To a solution of Intermediate 12-a (54 mg, 0.09 mmol) in MeOH (2 ml) was added 4N HCl in dioxane (5 ml, 30 mmol) and the solution was stirred at room temperature overnight Volatiles were removed under reduced pressure to provide Intermediate 12-b as a beige solid.

Step 3: Intermediate 12-c

To a solution of Intermediate 12-b.HCl (34 mg, 0.09 mmol) in THF (2 mL) and NMP (1 ml) cooled to −78° C.

-continued

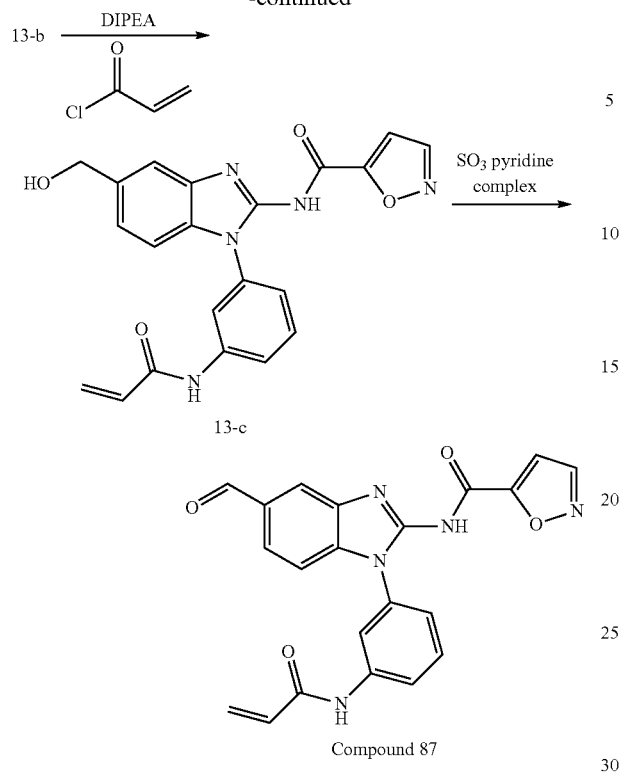

Step 1: Intermediate 13-a

To a solution of isoxazole-5-carboxylic acid (330 mg, 2.9 mmol) in DMF (24 ml) cooled to 0° C. was added HATU (1.2 g, 3.2 mmol) and after stirring for 30 minutes a solution of Intermediate 7-d (1.1 g, 2.4 mmol) and DIPEA (1.3 ml, 7.3 mmol) in DMF (3 ml) was added dropwise. The reaction was then stirred at room temperature for 1 day. A saturated aqueous solution of ammonium chloride and ethyl acetate were then added, the organic layer was separated, washed with a saturated aqueous solution of NaHCO$_3$ and brine, dried over anhydrous MgSO$_4$, filtered and concentrated under reduced pressure. Purification by silica gel chromatography provided Intermediate 13-a as a beige solid.

Step 2: Intermediate 13-b

To a solution of Intermediate 13-a (1.1 g, 2.0 mmol) in MeOH (1 ml) was added 4N HCl in dioxane (10.0 ml, 40.0 mmol) and the solution was stirred at room temperature overnight Volatiles were removed under reduced pressure to provide Intermediate 13-b.HCl as a beige solid.

Step 3: Intermediate 13-c

To a solution of Intermediate 13-b.HCl (700 mg, 2.0 mmol) in THF (20.0 mL) and NMP (1.5 ml) cooled to −78° C. were sequentially added DIPEA (3.5 ml, 20.0 mmol) and acryloyl chloride (163 μL, 2.0 mmol) and the solution was stirred at −78° C. for 30 minutes. Volatiles were removed under reduced pressure, water was added to the residue, a precipitate formed and was collected by filtration, washed with water and dried under vacuum to provide Intermediate 13-c as a beige solid.

Step 4: Compound 87

To a solution of Intermediate 13-c (620 mg, 1.5 mmol) in THF (3.1 ml) and DMSO (1.1 ml) cooled to 0° C. were sequentially added DIPEA (1.1 ml, 6.1 mmol) and a solution of SO$_3$ pyridine complex (734 mg, 4.6 mmol) in DMSO (10.0 mL). The mixture was then stirred at 0° C. for 2 hours. Volatiles were removed under reduced pressure, water was added, a precipitate formed and was collected by filtration, washed with water and dried under vacuum to provide Compound 87 as a beige solid.

Synthesis of Compound 76:

Scheme 14

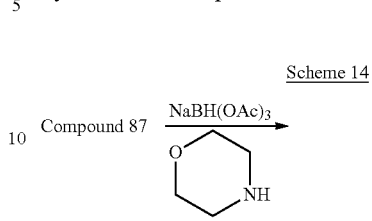

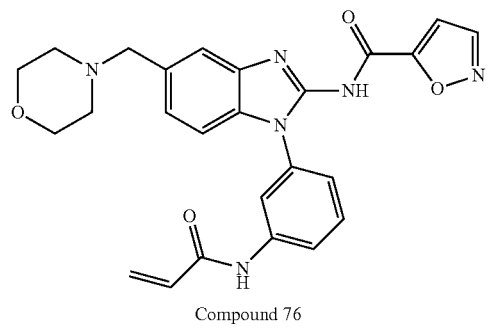

Compound 76

To a solution of Compound 87 (150 mg, 0.4 mmol) and morpholine (36 μl, 0.4 mmol) in dichloroethane (2.0 ml), were sequentially added acetic acid (11 μl, 0.2 mmol) and sodium triacetoxyborohydride (792 mg, 3.7 mmol) and the reaction was stirred overnight at room temperature. Volatiles were removed under reduced pressure. Purification by silica gel chromatography provided Compound 76 as a white solid.

Compounds 74 was prepared in a similar manner to Compound 76 by replacing morpholine with trans-4-amino-cyclohexanol Synthesis of Compound 88:

Scheme 15

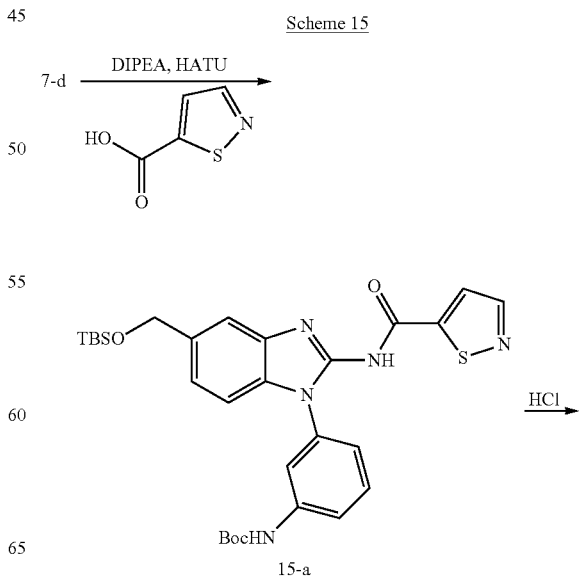

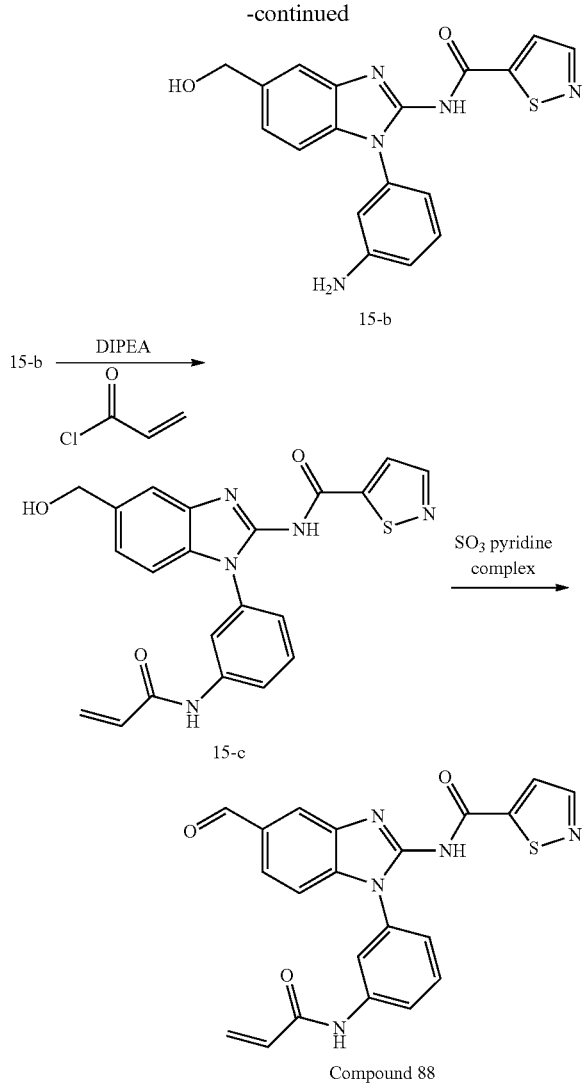

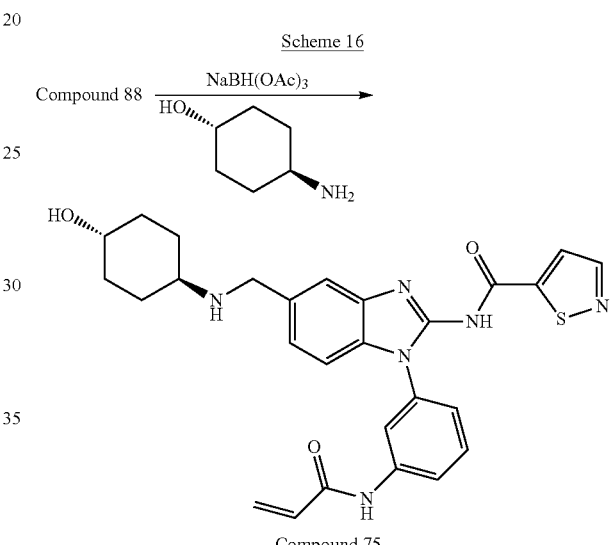

Scheme 16

C. were sequentially added DIPEA (2.9 ml, 16.4 mmol) and acryloyl chloride (133 µL, 1.6 mmol) and the solution was stirred at −78° C. for 30 minutes. Volatiles were removed under reduced pressure, water was added to the residue, a precipitate formed and was collected by filtration, washed with water and dried under vacuum to provide Intermediate 15-c as a beige solid.

Step 4: Compound 88

To a solution of Intermediate 15-c (500 mg, 1.2 mmol) in THF (5.6 ml) and DMSO (2.0 ml) cooled to 0° C. were sequentially added DIPEA (2.0 ml, 11.2 mmol) and a solution of $SO_3$ pyridine complex (1.4 g, 8.4 mmol) in DMSO (1.0 mL). The mixture was then stirred at 0'C for 1 hour. Volatiles were removed under reduced pressure, water was added, a precipitate formed and was collected by filtration, washed with water and dried under vacuum to provide Compound 88 as a beige solid.

Synthesis of Compound 75:

To a solution of isothiazole-5-carboxylic acid (331 mg, 2.6 mmol) in DMF (21 ml) cooled to 0° C. was added HATU (1.0 g, 2.8 mmol) and after stirring for 30 minutes a solution of Intermediate 7-d (1.0 g, 2.1 mmol) and DIPEA (1.1 ml, 6.4 mmol) in DMF (3 ml) was added dropwise. The reaction was then stirred at room temperature for 1 day. A saturated aqueous solution of ammonium chloride and ethyl acetate were then added, the organic layer was separated, washed with a saturated aqueous solution of $NaHCO_3$ and brine, dried over anhydrous $MgSO_4$, filtered and concentrated under reduced pressure. Purification by silica gel chromatography provided Intermediate 15-a as a beige solid.

Step 2: Intermediate 15-b

To a solution of Intermediate 15-a (950 mg, 1.6 mmol) in MeOH (1 ml) was added 4N HCl in dioxane (10.0 ml, 40.0 mmol) and the solution was stirred at room temperature overnight. Volatiles were removed under reduced pressure, diethyl ether and hexanes were added to the residue, a precipitate formed and was collected by filtration, dried under vacuum to provide Intermediate 15-b.HCl as a beige solid.

Step 3: Intermediate 15-c

To a solution of Intermediate 15-b.HCl (600 mg, 1.6 mmol) in THF (26.0 mL) and NMP (1.5 ml) cooled to −78°

To a solution of Compound 88 (150 mg, 0.4 mmol) and trans-4-aminocyclohexanol (43 mg, 0.4 mmol) in tetrahydrofuran (2.0 ml), were sequentially added acetic acid (10 µl, 0.2 mmol) and sodium triacetoxyborohydride (114 mg, 0.5 mmol) and the reaction was stirred overnight at room temperature. Volatiles were removed under reduced pressure. Purification by silica gel chromatography provided compound 75 as a white solid.

Compound 73 was prepared in a similar manner to Compound 75 by replacing trans-4-aminocyclohexanol with morpholine.

Synthesis of Intermediate 17-f:

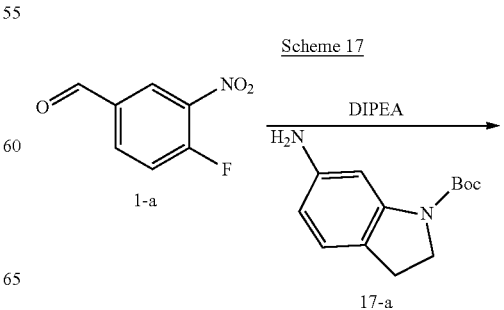

Scheme 17

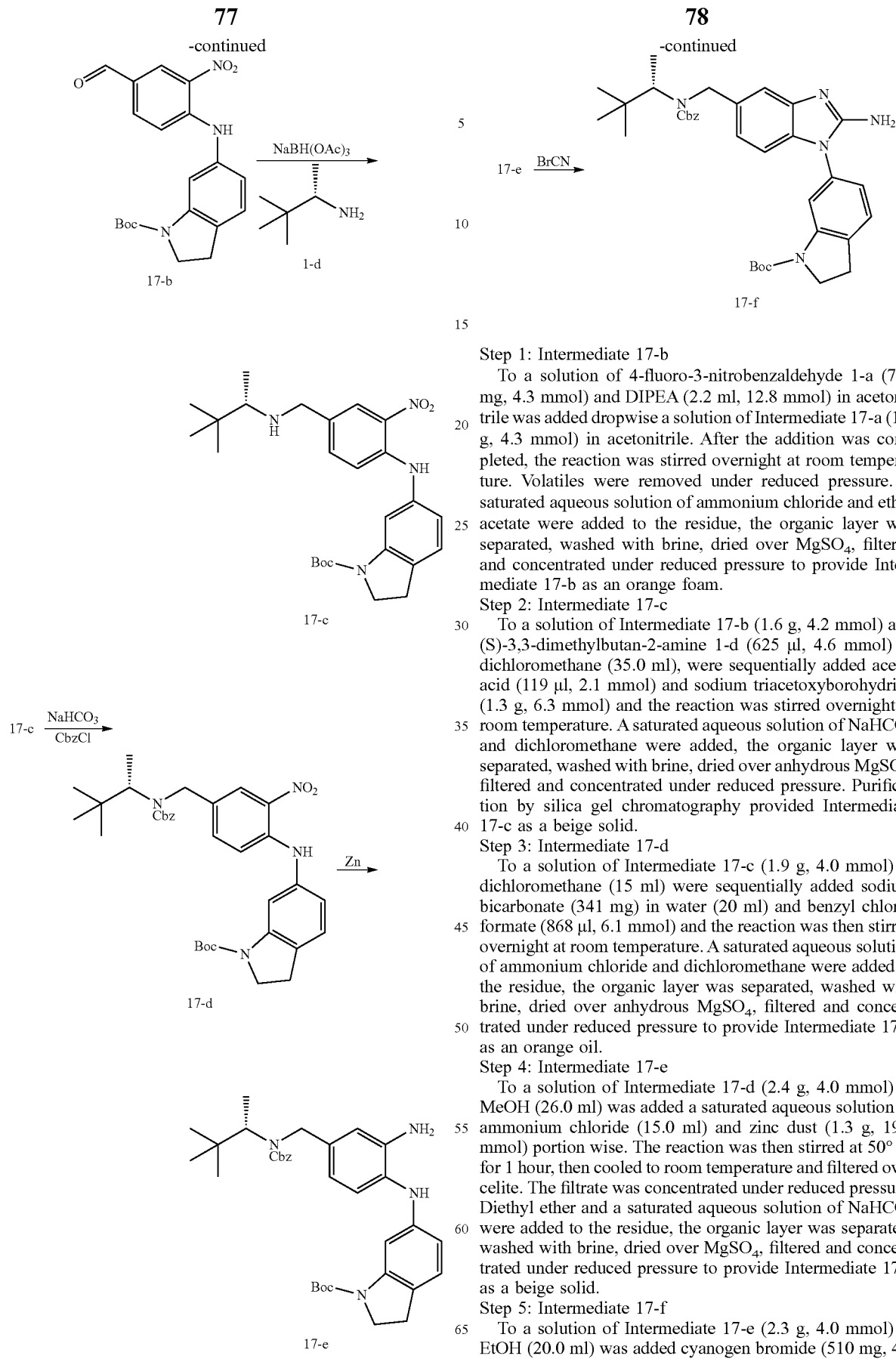

Step 1: Intermediate 17-b

To a solution of 4-fluoro-3-nitrobenzaldehyde 1-a (722 mg, 4.3 mmol) and DIPEA (2.2 ml, 12.8 mmol) in acetonitrile was added dropwise a solution of Intermediate 17-a (1.0 g, 4.3 mmol) in acetonitrile. After the addition was completed, the reaction was stirred overnight at room temperature. Volatiles were removed under reduced pressure. A saturated aqueous solution of ammonium chloride and ethyl acetate were added to the residue, the organic layer was separated, washed with brine, dried over MgSO$_4$, filtered and concentrated under reduced pressure to provide Intermediate 17-b as an orange foam.

Step 2: Intermediate 17-c

To a solution of Intermediate 17-b (1.6 g, 4.2 mmol) and (S)-3,3-dimethylbutan-2-amine 1-d (625 μl, 4.6 mmol) in dichloromethane (35.0 ml), were sequentially added acetic acid (119 μl, 2.1 mmol) and sodium triacetoxyborohydride (1.3 g, 6.3 mmol) and the reaction was stirred overnight at room temperature. A saturated aqueous solution of NaHCO$_3$ and dichloromethane were added, the organic layer was separated, washed with brine, dried over anhydrous MgSO$_4$, filtered and concentrated under reduced pressure. Purification by silica gel chromatography provided Intermediate 17-c as a beige solid.

Step 3: Intermediate 17-d

To a solution of Intermediate 17-c (1.9 g, 4.0 mmol) in dichloromethane (15 ml) were sequentially added sodium bicarbonate (341 mg) in water (20 ml) and benzyl chloroformate (868 μl, 6.1 mmol) and the reaction was then stirred overnight at room temperature. A saturated aqueous solution of ammonium chloride and dichloromethane were added to the residue, the organic layer was separated, washed with brine, dried over anhydrous MgSO$_4$, filtered and concentrated under reduced pressure to provide Intermediate 17-d as an orange oil.

Step 4: Intermediate 17-e

To a solution of Intermediate 17-d (2.4 g, 4.0 mmol) in MeOH (26.0 ml) was added a saturated aqueous solution of ammonium chloride (15.0 ml) and zinc dust (1.3 g, 19.9 mmol) portion wise. The reaction was then stirred at 50° C. for 1 hour, then cooled to room temperature and filtered over celite. The filtrate was concentrated under reduced pressure. Diethyl ether and a saturated aqueous solution of NaHCO$_3$ were added to the residue, the organic layer was separated, washed with brine, dried over MgSO$_4$, filtered and concentrated under reduced pressure to provide Intermediate 17-e as a beige solid.

Step 5: Intermediate 17-f

To a solution of Intermediate 17-e (2.3 g, 4.0 mmol) in EtOH (20.0 ml) was added cyanogen bromide (510 mg, 4.8 mmol) and the reaction was stirred for 4 hours at room temperature. Volatiles were removed under reduced pressure. A saturated aqueous solution of ammonium chloride and ethyl acetate were then added to the residue, the organic layer was separated, washed with a saturated aqueous solution of NaHCO₃ and brine, dried over MgSO₄, filtered and concentrated under reduced pressure to provide Intermediate 17-f as a beige solid.

Synthesis of Intermediate 18-a:

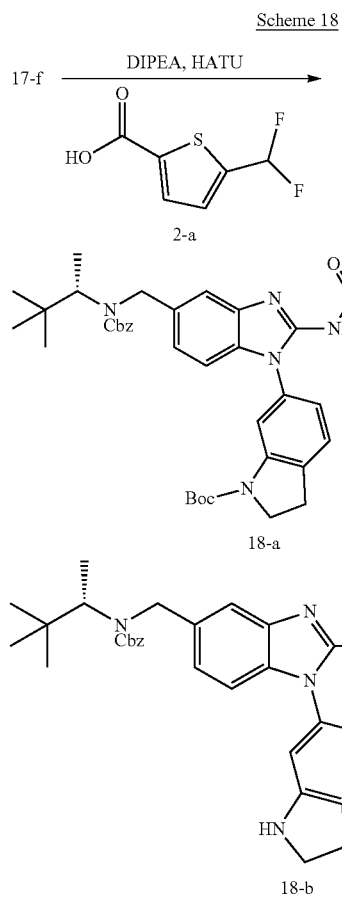

Synthesis of Compound 56:

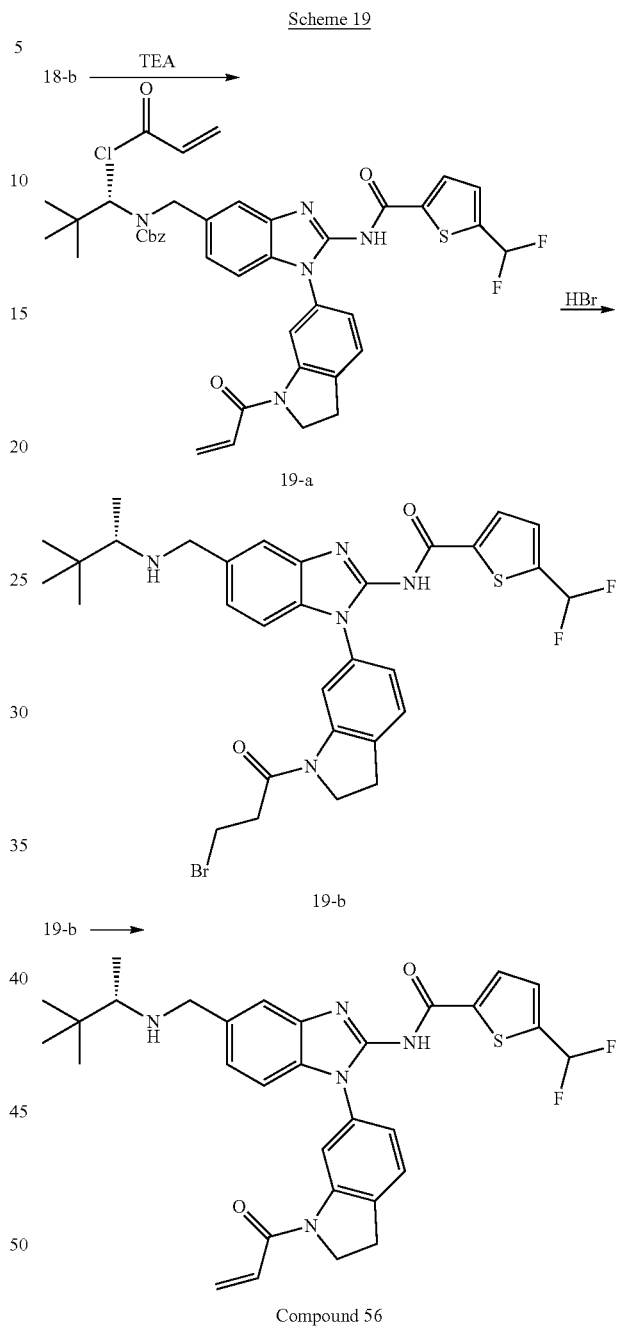

Step 1: Intermediate 18-a

To a solution of 5-(difluoromethyl)thiophene-2-carboxylic acid 2-a (137 mg, 0.8 mmol) in DMF (3.2 ml) cooled to 0° C. was added HATU (317 mg, 0.8 mmol) and after stirring for 30 minutes a solution of Intermediate 17-f (383 mg, 0.6 mmol) and DIPEA (336 µl, 1.9 mmol) in DMF (1.2 ml) was added dropwise. The reaction was then stirred at room temperature for 1 day. A saturated aqueous solution of ammonium chloride and ethyl acetate were then added, the organic layer was separated, washed with a saturated aqueous solution of ammonium chloride and brine, dried over anhydrous MgSO₄, filtered and concentrated under reduced pressure. Purification by silica gel chromatography provided Intermediate 18-a as a yellow solid.

Step 2: Intermediate 18-b

To a solution of Intermediate 18-a (177 mg, 0.2 mmol) in MeOH (1 ml) was added 4N HCl in dioxane (4.0 ml, 16.0 mmol) at room temperature and the solution was stirred for 1 hour. Volatiles were removed under reduced pressure, diethyl ether was added, a precipitate formed and was collected by filtration, dried under vacuum to provide Intermediate 18-b.HCl as a white solid.

Step 1: Intermediate 19-a

To a solution of Intermediate 18-b.HCl (138 mg, 0.2 mmol) in THF (20.0 mL) cooled to −78° C. were sequentially added TEA (277 µl, 1.2 mmol) and acryloyl chloride (24 µL, 0.3 mmol) and the solution was stirred at −78° C. for 30 minutes. A saturated aqueous solution of ammonium chloride and ethyl acetate were then added, the organic layer was separated, and the aqueous phase was extracted twice with ethyl acetate. The combined organic extracts were washed with brine, dried over MgSO₄, filtered and concentrated under reduced pressure to provide Intermediate 19-a as an off white foam.

Step 2: Intermediate 19-b

To a solution of Intermediate 19-a (130 mg, 0.2 mmol) in dichloromethane (2.0 ml) was added a solution of 33% HBr in AcOH (2.0 ml, 12.1 mmol) at 0° C. and the solution was then stirred at room temperature until completion. Diethyl ether was added; a precipitate formed and was collected by filtration then dried under vacuum to provide Intermediate 19-b as a white solid.

Step 3: Compound 56

To a solution of Intermediate 19-b (120 mg, 0.2 mmol) in THF was added cesium carbonate (475 mg, 1.5 mmol) and the reaction was heated at 60° C. overnight then cooled to room temperature and filtered. The filtrate was concentrated under reduced pressure. Purification by silica gel chromatography provided Compound 56 as a white solid.

Compounds 57 was prepared in a similar manner to compound 56 by replacing tert-butyl 6-aminoindoline-1-carboxylate with tert-butyl 6-amino-2H-benzo[b][1,4]oxazine-4(3H)-carboxylate for the synthesis of Intermediate 17-f.

Synthesis of Intermediate 20-e:

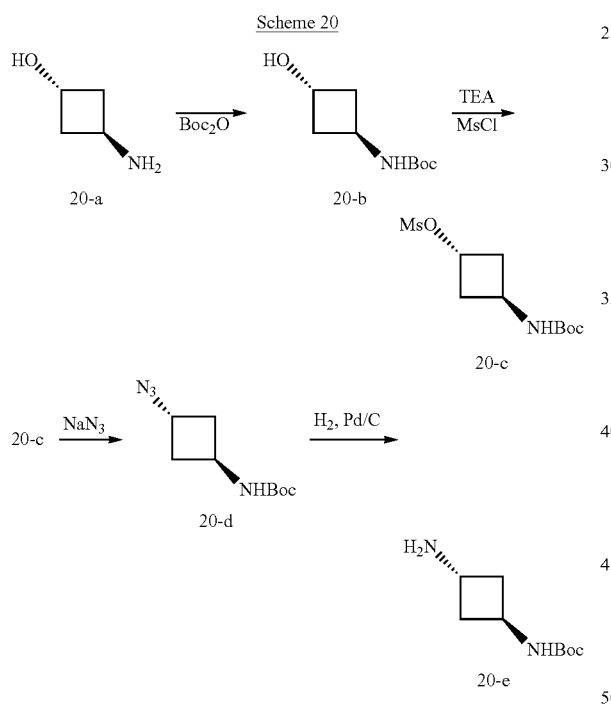

Step 1: Intermediate 20-b

To a solution of 3-aminocyclobutanol.HCl.H$_2$O 20-a (25.0 g, 177.0 mmol) in EtOH (88 ml) were sequentially added TEA (88.0 ml) and Boc$_2$O (53.3 ml, 230.0 mmol) and the mixture was stirred at room temperature overnight. Volatiles were removed under reduced pressure. Water and ethyl acetate were added to the residue, the organic layer was separated, washed with a saturated aqueous solution of ammonium chloride, 10% aqueous citric acid, a saturated aqueous solution of NaHCO$_3$ and brine, dried over anhydrous MgSO$_4$, filtered and concentrated under reduced pressure to provide Intermediate 20-b as a white solid.

Step 2: Intermediate 20-c

To a solution of Intermediate 20-b (2.0 g, 10.7 mmol) in dichloromethane (42.7 ml) were sequentially added TEA (3.0 ml, 21.4 mmol) and methanesulfonyl chloride (1.3 ml, 16.0 mmol) at 0° C. and the reaction was then stirred at room temperature for 1 hour. A saturated aqueous solution of ammonium chloride was added, the organic layer was separated, washed with brine, dried over anhydrous MgSO$_4$, filtered and concentrated under reduced pressure to provide Intermediate 20-c as a white solid.

Step 3: Intermediate 20-d

To a solution of Intermediate 20-c (2.8 g, 10.7 mmol) in DMF (42.7 ml) was added sodium azide (1.0 g, 16.0 mmol) and the reaction was stirred at 85° C. overnight and then cooled to room temperature. A saturated aqueous solution of ammonium chloride and diethyl ether were added, the organic layer was separated, washed with a saturated aqueous solution of ammonium chloride and brine, dried over anhydrous MgSO$_4$, filtered and concentrated under reduced pressure to provide Intermediate 20-d as white solid.

Step 4: Intermediate 20-e

To a solution of Intermediate 20-d (2.1 g, 9.9 mmol) in methanol (30 ml) and stirred under nitrogen was added 10% Pd/C (211 g, 0.2 mmol). The reaction mixture was purged with H$_2$ and stirred for 3 hours under H$_2$. The reaction was then filtered through celite and the filtrate was concentrated in vacuo to provide Intermediate 20-e as a white solid.

Synthesis of Intermediate 21-f:

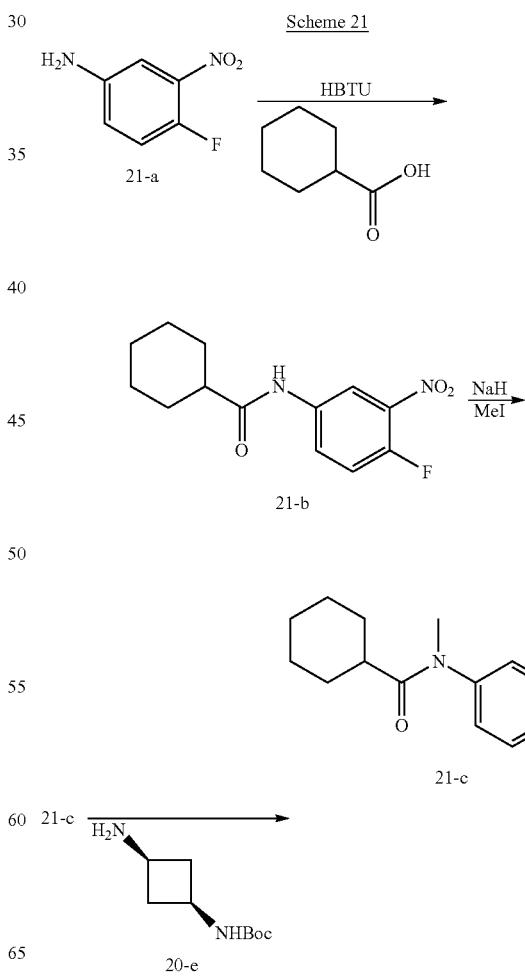

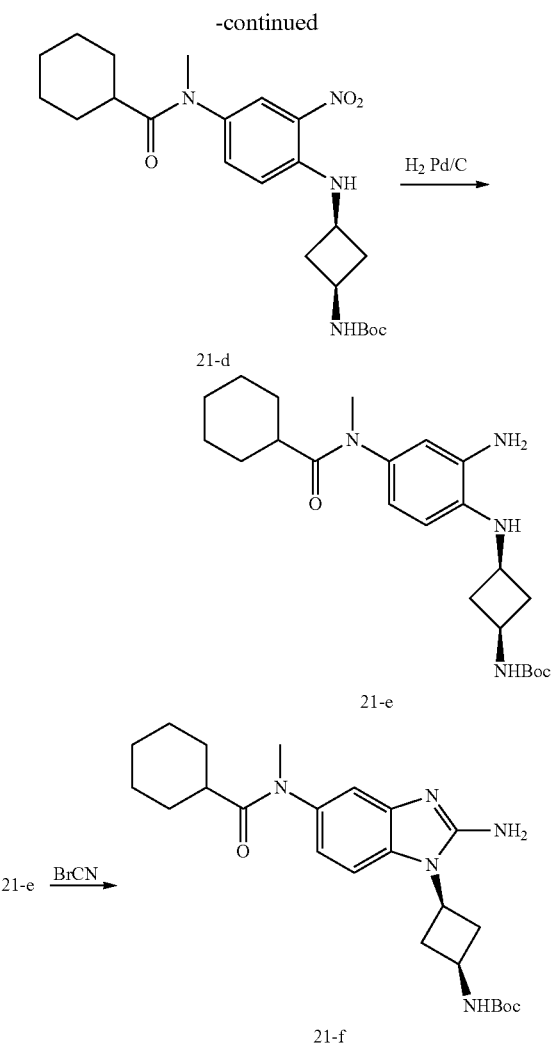

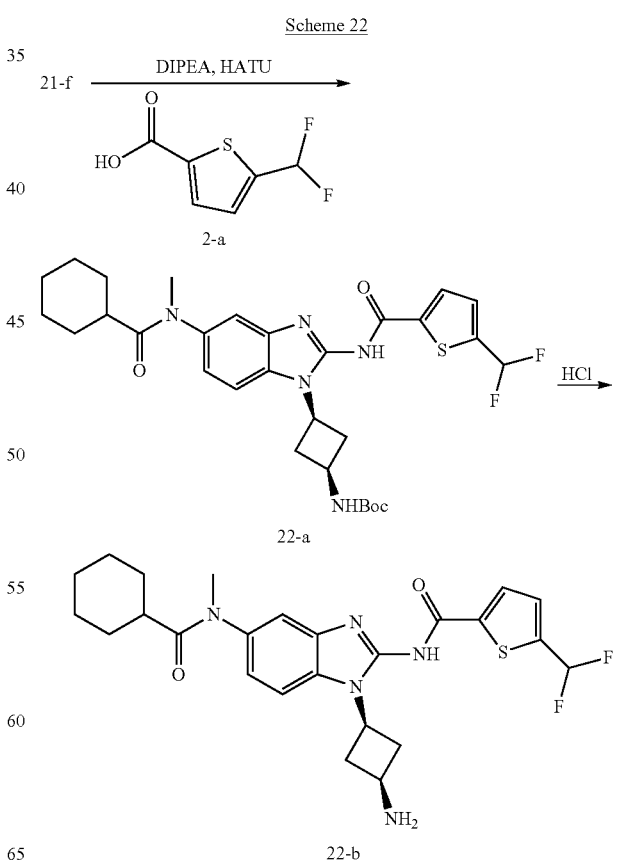

anhydrous MgSO$_4$, filtered and concentrated under reduced pressure to provide Intermediate 21-c as a beige oil.

Step 3: Intermediate 21-d

A solution of Intermediate 21-c (205 mg, 0.7 mmol), Intermediate 20-e (136 mg, 9.3 mmol) and DIPEA (382 µl, 2.2 mmol) in DMSO was heated at 100° C. for 1 h 30 minutes and then cooled to room temperature. A saturated aqueous solution of ammonium chloride and ethyl acetate were added, the organic layer was separated, washed with a saturated aqueous solution of ammonium chloride and brine, dried over anhydrous MgSO$_4$, filtered and concentrated under reduced pressure to provide Intermediate 21-d as a yellow solid.

Step 4: Intermediate 21-e

To a solution of Intermediate 21-d (330 mg, 0.7 mmol) in methanol and stirred under nitrogen was added 10% Pd/C (16 mg, 0.15 mmol). The reaction mixture was purged with H$_2$ and stirred for 1 day under H$_2$. The reaction was then filtered through celite and the filtrate was concentrated in vacuo to provide Intermediate 21-e as a beige solid.

Step 4: Intermediate 21-f

To a solution of Intermediate 21-e (310 mg, 0.7 mmol) in EtOH (7.4 ml) was added cyanogen bromide (95 mg, 0.9 mmol) and the reaction was stirred for 5 hours at room temperature. Volatiles were removed under reduced pressure. A saturated aqueous solution of ammonium chloride and ethyl acetate were then added to the residue, the organic layer was separated, washed with a saturated aqueous solution of NaHCO$_3$ and brine, dried over anhydrous MgSO$_4$, filtered and concentrated under reduced pressure to provide Intermediate 21-f as a beige solid.

Synthesis of Intermediate 22-b:

Scheme 22

Step 1: Intermediate 21-b

To a solution of cyclohexanecarboxylic acid (6.9 g, 53.8 mmol) in DMF (160 ml) cooled to 0° C. were sequentially added, HBTU (22.1 g, 58.3 mmol) and after stirring for 30 minutes, a solution of 4-fluoro-3-nitroaniline 21-a (7.0 g, 44.8 mmol) and DiPEA (23.4 ml, 135.0 mmol) in DMF (80 ml) was added. The reaction was then stirred for 5 days at room temperature. A saturated aqueous solution of ammonium chloride and ethyl acetate were added, the organic layer was separated, washed with a saturated aqueous solution of ammonium chloride and brine, dried over anhydrous MgSO$_4$, filtered and concentrated under reduced pressure. Purification by silica gel chromatography provided Intermediate 21-b as a yellow solid.

Step 2: Intermediate 21-c

To a suspension of NaH (60% dispersion in mineral oil, 265 mg, 6.6 mmol) in DMF was added Intermediate 21-b (1.0 g, 3.8 mmol) and after stirring for 15 minutes at room temperature iodomethane (552 µl, 8.9 mmol) was added. After the addition was completed, the reaction was stirred at 60° C. for 2 hours and then cooled to room temperature. Volatiles were removed under reduced pressure. An aqueous solution of 1N HCl and ethyl acetate were added to the residue, the organic layer was separated, washed with a saturated aqueous solution of NaHCO$_3$ and brine, dried over Step 1: Intermediate 22-a To a solution of 5-(difluoromethyl)thiophene-2-carboxylic acid 2-a (200 mg, 1.1 mmol) in DMF (3.2 ml) cooled to 0° C. was added HATU (483 mg, 1.3 mmol) and after stirring for 30 minutes a solution of Intermediate 21-f (330 mg, 0.7 mmol) and DIPEA (522 µl, 3.0 mmol) in DMF (3.2 ml) was added dropwise. The reaction was then stirred at room temperature overnight. A saturated aqueous solution of ammonium chloride and ethyl acetate were then added, the organic layer was separated, washed with a saturated aqueous solution of ammonium chloride and brine, dried over anhydrous MgSO₄, filtered and concentrated under reduced pressure. Purification by silica gel chromatography provided Intermediate 22-a as a beige solid.

Step 2: Intermediate 22-b

To a solution of Intermediate 22-a (253 mg, 0.4 mmol) in MeOH (1 ml) was added 4N HCl in 1,4-dioxane (13.8 ml, 55.1 mmol) at room temperature and the solution was stirred at room temperature overnight. Volatiles were removed under reduced pressure and the residue was dried under vacuum to provide Intermediate 22-b.HCl as beige solid.

Synthesis of Compound 63:

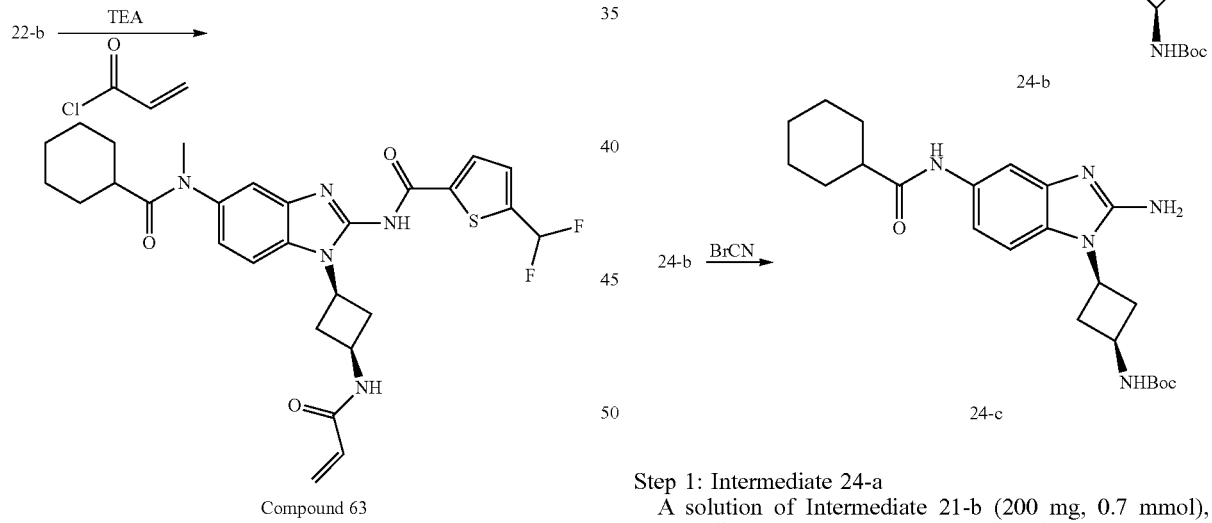

Compound 63

To a solution of Intermediate 22-b.HCl (211 mg, 0.4 mmol) in tetrahydrofuran (4.2 ml) and NMP (1 ml) cooled to −78° C. were sequentially added DIPEA (733 µl, 4.2 mmol) and acryloyl chloride (41 µl, 0.5 mmol) and the reaction was stirred at −78° C. for 2 hours. Water (20 mL) and ethyl acetate (20 mL) were added; the organic layer was separated, washed with a saturated aqueous solution of NaHCO₃ and brine, dried over anhydrous MgSO₄, filtered and concentrated under reduced pressure. Purification by silica gel chromatography provided Compound 63 as a white solid.

Synthesis of Intermediate 24-c:

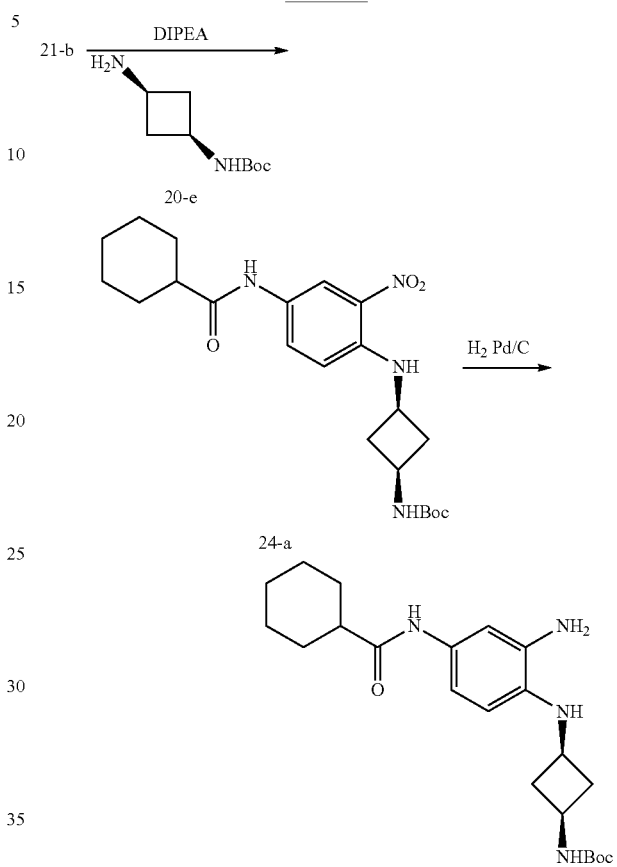

Step 1: Intermediate 24-a

A solution of Intermediate 21-b (200 mg, 0.7 mmol), Intermediate 20-e (140 mg, 07 mmol) and DIPEA (392 µl, 2.2 mmol) in DMSO was heated at 100° C. for 3 h 30 minutes and then cooled to room temperature. A saturated aqueous solution of ammonium chloride and ethyl acetate were added, the organic layer was separated, washed with a saturated aqueous solution of ammonium chloride and brine, dried over anhydrous MgSO₄, filtered and concentrated under reduced pressure to provide Intermediate 24-a as a yellow solid.

Step 2: Intermediate 24-b

To a solution of Intermediate 24-a (270 mg, 0.6 mmol) in methanol and stirred under nitrogen was added 10% Pd/C (30 mg, 0.03 mmol). The reaction mixture was purged with H₂ and stirred for 24 hours under H₂. The reaction was then filtered through celite and the filtrate was concentrated under reduced pressure to provide Intermediate 24-b as a beige solid.

Step 3: Intermediate 24-c

To a solution of Intermediate 24-b (230 mg, 0.6 mmol) in EtOH (5.7 ml) was added cyanogen bromide (73 mg, 0.7 mmol) and the reaction was stirred for 3 hours at room temperature. Volatiles were removed under reduced pressure. A saturated aqueous solution of ammonium chloride and ethyl acetate were then added to the residue, the organic layer was separated, washed with a saturated aqueous solution of NaHCO$_3$ and brine, dried over anhydrous MgSO$_4$, filtered and concentrated under reduced pressure to provide Intermediate 24-c as a beige solid.

Synthesis of Intermediate 25-b:

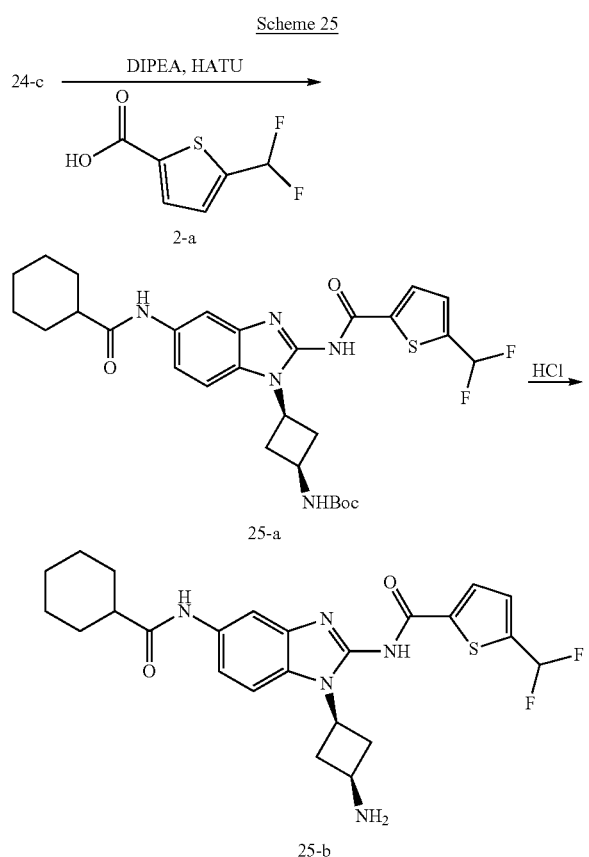

Step 1: Intermediate 25-a

To a solution of 5-(difluoromethyl)thiophene-2-carboxylic acid 2-a (75 mg, 0.4 mmol) in DMF (1.2 ml) cooled to 0° C. was added HATU (181 mg, 0.4 mmol) and after stirring for 30 minutes a solution of Intermediate 24-c (120 mg, 0.3 mmol) and DIPEA (196 µl, 1.1 mmol) in DMF (1.2 ml) was added dropwise. The reaction was then stirred at room temperature for 1 day. A saturated aqueous solution of ammonium chloride and ethyl acetate were then added, the organic layer was separated, washed with a saturated aqueous solution of ammonium chloride and brine, dried over anhydrous MgSO$_4$, filtered and concentrated under reduced pressure. Purification by silica gel chromatography provided Intermediate 25-a as a beige solid.

Step 2: Intermediate 25-b

To a solution of Intermediate 25-a (18 mg, 0.02 mmol) in MeOH (500 µl) was added 4N HCl in dioxane (1.0 ml, 4.0 mmol) at room temperature and the solution was stirred overnight. Volatiles were removed under reduced pressure and the residue was dried under vacuum to provide Intermediate 25-b.HCl as beige solid.

Synthesis of Compound 64:

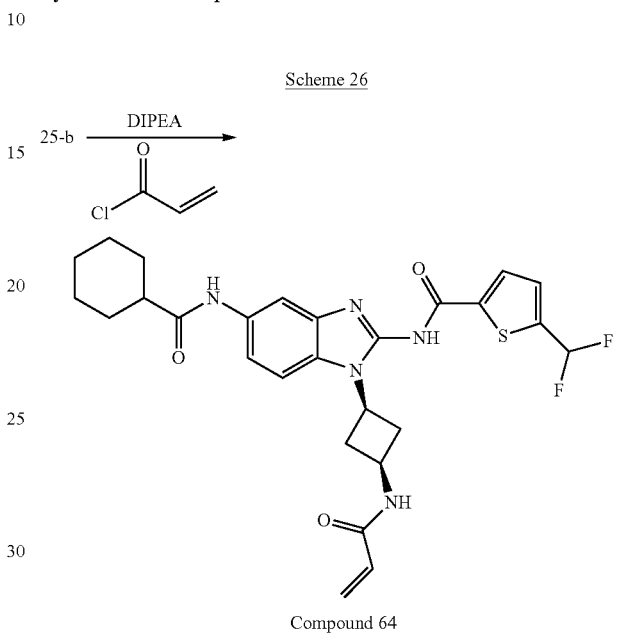

To a solution of Intermediate 25-b.HCl (18 mg, 0.04 mmol) in tetrahydrofuran (370 µl) cooled to −78° C. were sequentially added DIPEA (64 µl, 0.4 mmol) and acryloyl chloride (3.6 µl, 0.04 mmol) and the reaction was stirred at −78° C. for 30 minutes. Water (20 mL) and ethyl acetate (20 mL) were added; the organic layer was separated, washed with a saturated aqueous solution of NaHCO$_3$ and brine, dried over anhydrous MgSO$_4$, filtered and concentrated under reduced pressure. Purification by silica gel chromatography provided Compound 64 as a white solid.

Synthesis of Intermediate 27-f:

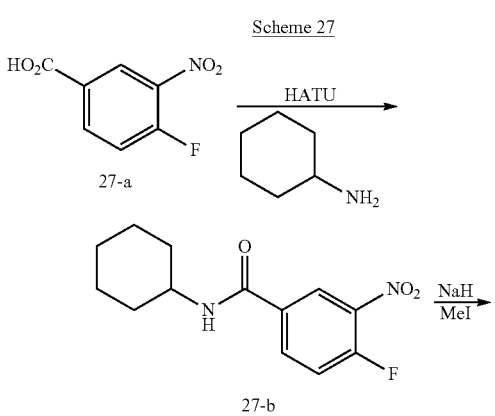

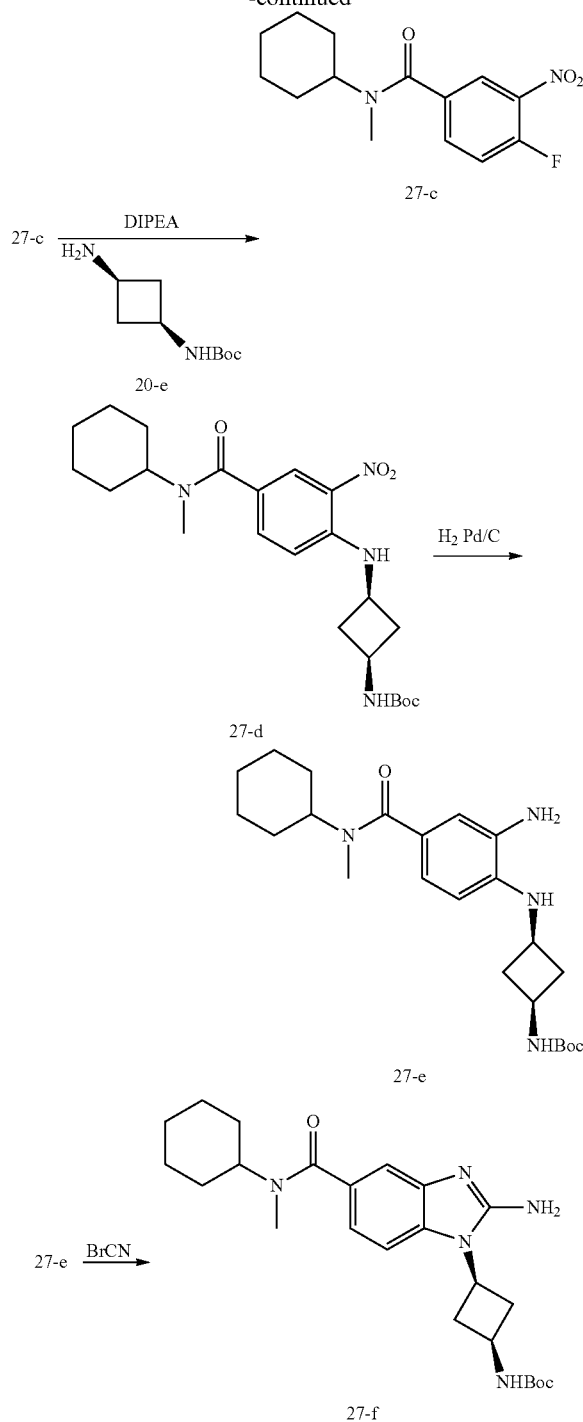

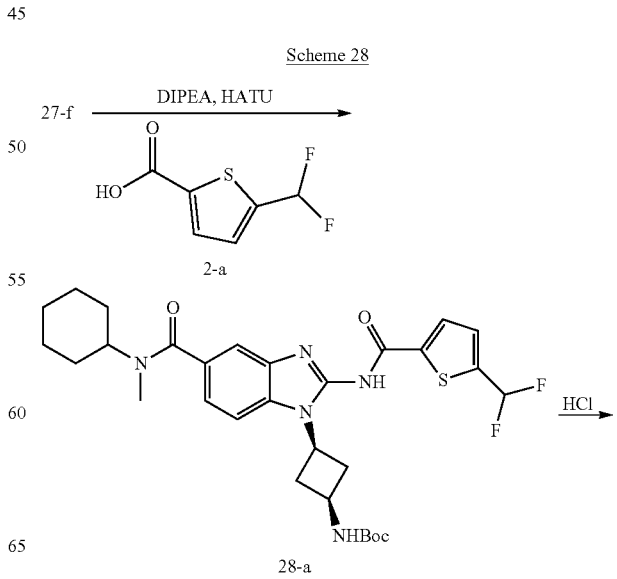

centrated under reduced pressure. Purification by silica gel chromatography provided Intermediate 27-b as a yellow solid.

Step 2: Intermediate 27-c

To a suspension of NaH (60% dispersion in mineral oil, 397 mg, 9.9 mmol) in DMF was added Intermediate 27-b (1.5 g, 5.6 mmol) and after stirring for 15 minutes at room temperature iodomethane (828 μl, 13.3 mmol) was added. After the addition was completed, the reaction was stirred at 60° C. for 1 hour and then cooled to room temperature. Volatiles were removed under reduced pressure. An aqueous solution of 1N HCl and ethyl acetate were added to the residue, the organic layer was separated, washed with a saturated aqueous solution of $NaHCO_3$ and brine, dried over anhydrous $MgSO_4$, filtered and concentrated under reduced pressure to provide Intermediate 27-c as an orange oil.

Step 3: Intermediate 27-d

A solution of Intermediate 27-c (211 mg, 0.7 mmol), Intermediate 20-e (140 mg, 0.7 mmol) and DIPEA (393 μl, 2.2 mmol) in acetonitrile was stirred at room temperature for 1 day. A saturated aqueous solution of ammonium chloride and ethyl acetate were added, the organic layer was separated, washed with a saturated aqueous solution of ammonium chloride and brine, dried over anhydrous $MgSO_4$, filtered and concentrated under reduced pressure to provide Intermediate 27-d as an orange solid.

Step 4: Intermediate 27-e

To a solution of Intermediate 27-d (336 mg, 0.7 mmol) in methanol and stirred under nitrogen was added 10% Pd/C (40 mg, 0.04 mmol). The reaction mixture was purged with $H_2$ and stirred for 1 day under $H_2$. The reaction was then filtered through celite and the filtrate was concentrated in vacuo to provide Intermediate 27-e as a purple oil.

Step 5: Intermediate 27-f

To a solution of Intermediate 27-e (270 mg, 0.6 mmol) in EtOH (6.5 ml) was added cyanogen bromide (82 mg, 0.8 mmol) and the reaction was stirred for 3 hours at room temperature. Volatiles were removed under reduced pressure. A saturated aqueous solution of ammonium chloride and ethyl acetate were then added to the residue, the organic layer was separated, washed with a saturated aqueous solution of $NaHCO_3$ and brine, dried over anhydrous $MgSO_4$, filtered and concentrated under reduced pressure to provide Intermediate 27-f as a beige solid.

Synthesis of Intermediate 28-b:

Step 1: Intermediate 27-b

To a solution of 4-fluoro-3-nitrobenzoic acid 27-a (10.0 g, 54.0 mmol) in DMF (160 ml) cooled to 0° C. were sequentially added HATU (22.2 g, 58.5 mmol), cyclohexanamine (5.2 ml, 45.0 mmol) and DIPEA (23.5 ml, 135.0 mmol). The reaction was stirred at room temperature for 1 day. A saturated aqueous solution of ammonium chloride and ethyl acetate were added, the organic layer was separated, washed with a saturated aqueous solution of ammonium chloride and brine, dried over anhydrous $MgSO_4$, filtered and con-

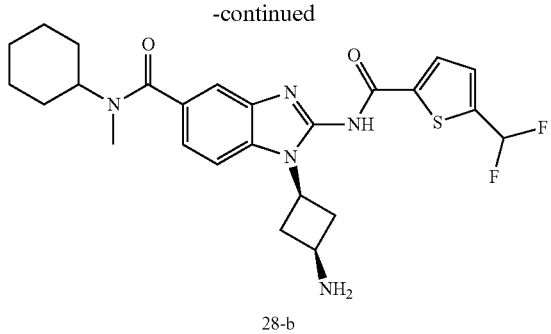

28-b

Step 1: Intermediate 28-a

To a solution of 5-(difluoromethyl)thiophene-2-carboxylic acid 2-a (61 mg, 0.34 mmol) in DMF (1.0 ml) cooled to 0° C. was added HATU (146 mg, 0.38 mmol) and after stirring for 30 minutes a solution of Intermediate 27-f (100 mg, 0.22 mmol) and DIPEA (119 µl, 0.68 mmol) in DMF (1.0 ml) was added dropwise. The reaction was then stirred at room temperature for 1 day. A saturated aqueous solution of ammonium chloride and ethyl acetate were then added, the organic layer was separated, washed with a saturated aqueous solution of ammonium chloride and brine, dried over anhydrous MgSO$_4$, filtered and concentrated under reduced pressure. Purification by silica gel chromatography provided Intermediate 28-a as a white solid.

Step 2: Intermediate 28-b

To a solution of Intermediate 28-a (73 mg, 0.12 mmol) in MeOH (500 µl) was added 4N HCl in 1,4-dioxane (3.0 ml, 12.0 mmol) at room temperature and the solution was stirred overnight. Volatiles were removed under reduced pressure and the residue was dried under vacuum to provide Intermediate 28-b.HCl as white solid.

Synthesis of Compound 65:

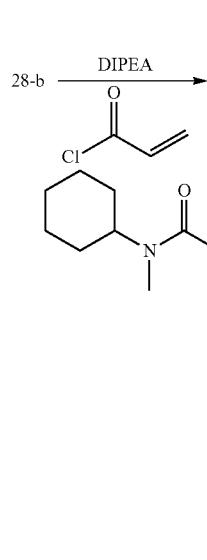

Compound 65

To a solution of Intermediate 28-b.HCl (60 mg, 0.12 mmol) in tetrahydrofuran (1.2 ml) cooled to −78° C. were sequentially added DIPEA (208 µl, 1.2 mmol) and acryloyl chloride (xx µl, 0.14 mmol) and the reaction was stirred at −78° C. for 30 minutes. Water (20 mL) and ethyl acetate (20 mL) were added; the organic layer was separated, washed with a saturated aqueous solution of NaHCO$_3$ and brine, dried over anhydrous MgSO$_4$, filtered and concentrated under reduced pressure. Purification by silica gel chromatography provided Compound 65 as a white solid.

Compound 48 was prepared in a similar manner to Compound 65 by replacing Intermediate 20-e with tert-butyl 3-aminophenylcarbamate 1-b for the synthesis of Intermediate 27-f.

Synthesis of Intermediate 30-c:

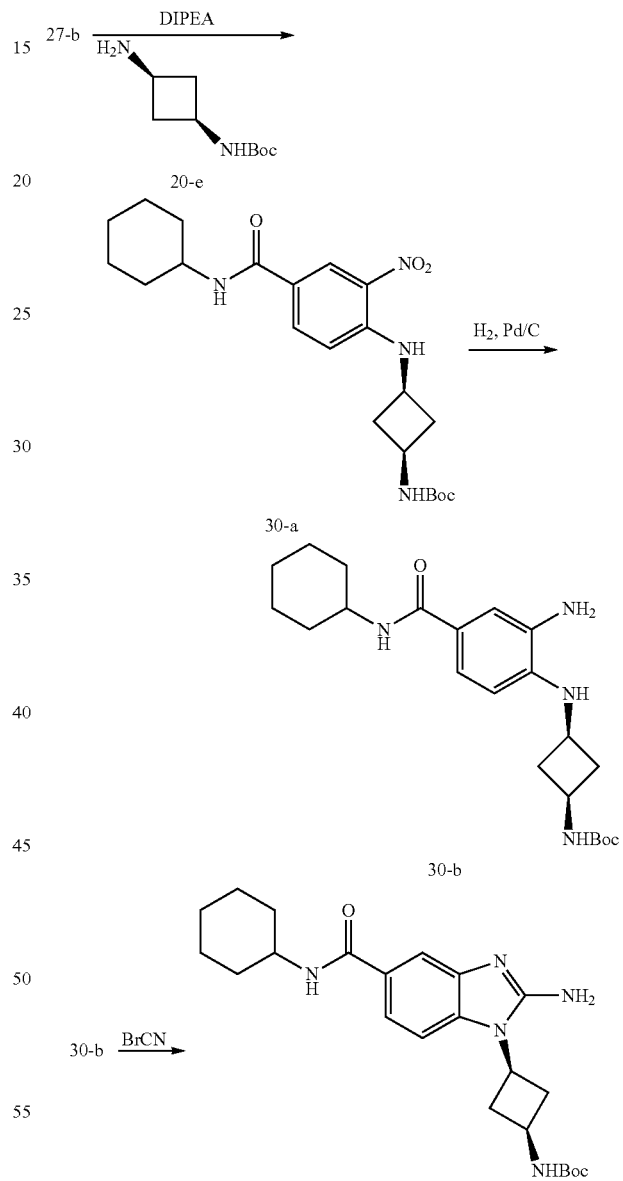

Step 1: Intermediate 30-a

A solution of Intermediate 27-b (1.0 g, 3.8 mmol), Intermediate 20-e (699 mg, 3.8 mmol) and DIPEA (1.9 ml, 11.3 mmol) in acetonitrile was stirred at room temperature for 1 day. A saturated aqueous solution of ammonium chloride and ethyl acetate were added, the organic layer was separated, washed with a saturated aqueous solution of ammonium chloride and brine, dried over anhydrous MgSO₄, filtered and concentrated under reduced pressure to provide Intermediate 30-a as a yellow solid.

Step 2: Intermediate 30-b

To a solution of Intermediate 30-a (1.2 g, 2.8 mmol) in methanol (28.0 ml) and stirred under nitrogen was added 10% Pd/C (300 mg, 0.28 mmol). The reaction mixture was purged with H₂ and stirred for 1 day under H₂. The reaction was then filtered through celite and the filtrate was concentrated under reduced pressure to provide Intermediate 30-b as a beige solid.

Step 3: Intermediate 30-c

To a solution of Intermediate 30-b (410 mg, 1.0 mmol) in EtOH (10.2 ml) was added cyanogen bromide (129 mg, 1.2 mmol) and the reaction was stirred for 4 hours at room temperature. Volatiles were removed under reduced pressure. A saturated aqueous solution of ammonium chloride and ethyl acetate were then added to the residue, the organic layer was separated, washed with a saturated aqueous solution of NaHCO₃ and brine, dried over anhydrous MgSO₄, filtered and concentrated under reduced pressure to provide Intermediate 30-c as a beige solid.

Synthesis of Intermediate 31-b:

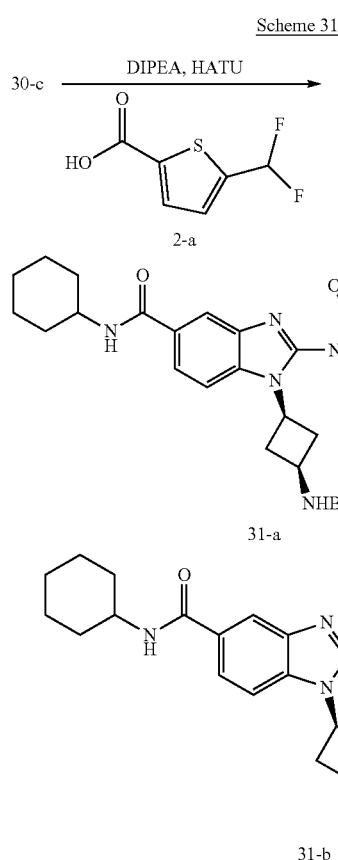

Step 1: Intermediate 31-a

To a solution of 5-(difluoromethyl)thiophene-2-carboxylic acid 2-a (275 mg, 1.5 mmol) in DMF (4.4 ml) cooled to 0° C. was added HATU (665 mg, 1.8 mmol) and after stirring for 30 minutes a solution of Intermediate 30-c (440 mg, 1.0 mmol) and DIPEA (719 µl, 4.1 mmol) in DMF (4.4 ml) was added dropwise. The reaction was then stirred at room temperature for 1 day. A saturated aqueous solution of ammonium chloride and ethyl acetate were then added, the organic layer was separated, washed with a saturated aqueous solution of ammonium chloride and brine, dried over anhydrous MgSO₄, filtered and concentrated under reduced pressure. Purification by silica gel chromatography provided Intermediate 31-a as a yellow solid.

Step 2: Intermediate 31-b

To a solution of Intermediate 31-a (17 mg, 0.03 mmol) in MeOH (500 µl) was added 4N HCl in dioxane (947 µl, 3.8 mmol) at room temperature and the solution was stirred overnight. Volatiles were removed under reduced pressure and the residue was dried under vacuum to provide Intermediate 31-b.HCl as white solid.

Synthesis of Compound 70:

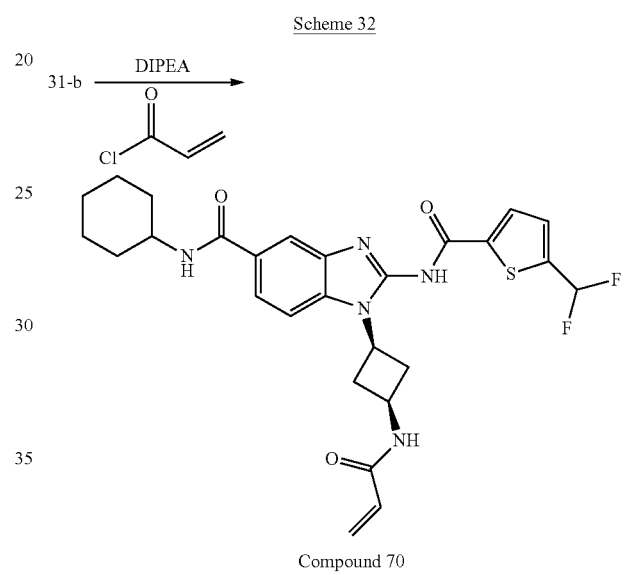

To a solution of Intermediate 31-b (15 mg, 0.03 mmol) in tetrahydrofuran (300 µl) cooled to −78° C. were sequentially added DIPEA (54 µl, 0.3 mmol) and acryloyl chloride (3.0 µl, 0.04 mmol) and the reaction was stirred at −78° C. for 30 minutes. Water (20 mL) and ethyl acetate (20 mL) were added; the organic layer was separated, washed with a saturated aqueous solution of NaHCO₃ and brine, dried over anhydrous MgSO₄, filtered and concentrated under reduced pressure. Purification by silica gel chromatography provided Compound 70 as a white solid.

Compounds 53 was prepared in a similar manner to Compound 70 by replacing Intermediate 20-e with tert-butyl 3-aminophenylcarbamate 1-b for the synthesis of Intermediate 30-c.

Synthesis of Intermediate 33-f:

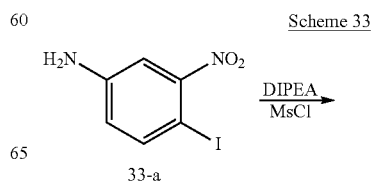

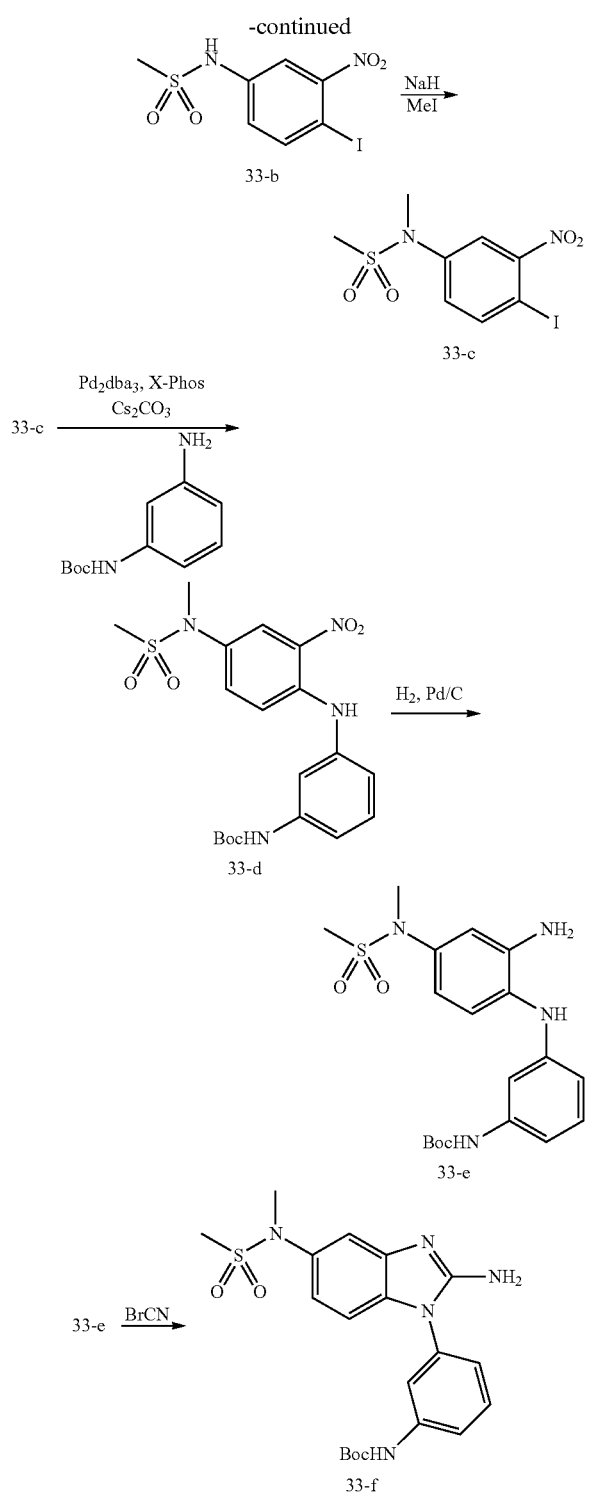

filtered and concentrated under reduced pressure. Ethyl acetate was added; the organic layer was separated, washed with brine, dried over anhydrous $MgSO_4$, filtered and concentrated under reduced pressure to provide Intermediate 33-b as a white solid.

Step 2: Intermediate 33-c

To a solution of Intermediate 33-b (520 mg, 1.5 mmol) in acetonitrile (4.3 ml) were sequentially added $K_2CO_3$ (630 mg, 4.6 mmol) and methyl iodide (285 μl, 4.6 mmol). The reaction was stirred at room temperature for 2 days and then filtered. The filtrate was concentrated to half volume under reduced pressure, a saturated aqueous solution of ammonium chloride and dichloromethane were added; the organic layer was separated, washed with brine, dried over anhydrous $MgSO_4$, filtered and concentrated under reduced pressure to provide Intermediate 33-c as a yellow solid.

Step 3: Intermediate 33-d

A degassed solution of tert-butyl 3-aminophenylcarbamate 1-b (639 mg, 3.1 mmol), Intermediate 33-c (500 mg, 1.5 mmol), $Cs_2CO_3$ (1.4 g, 4.4 mmol), X-Phos (70 mg, 0.15 mmol) and $Pd_2dba_3$ (37 mg, 0.07 mmol) in 1,4-dioxane (14.6 ml) was heated at 100° C. for 1 day and then cooled to room temperature. A saturated aqueous solution of ammonium chloride and ethyl acetate were then added, the organic layer was separated, washed with a saturated aqueous solution of ammonium chloride and brine, dried over anhydrous $MgSO_4$, filtered and concentrated under reduced pressure. Purification by silica gel chromatography provided Intermediate 33-d as beige solid.

Step 4: Intermediate 33-e

To a solution of Intermediate 33-d (349 mg, 0.8 mmol) in methanol and stirred under nitrogen was added 10% Pd/C (17 mg, 0.08 mmol). The reaction mixture was purged with $H_2$ and stirred for 1 day under $H_2$. The reaction was then filtered through celite and the filtrate was concentrated in vacuo to provide Intermediate 33-e as a beige solid.

Step 5: Intermediate 33-f

To a solution of Intermediate 33-e (322 mg, 0.8 mmol) in EtOH (7.9 ml) was added cyanogen bromide (105 mg, 1.0 mmol) and the reaction was stirred at room temperature overnight. Volatiles were removed under reduced pressure. A saturated aqueous solution of ammonium chloride and ethyl acetate were then added to the residue, the organic layer was separated, washed with a saturated aqueous solution of $NaHCO_3$ and brine, dried over anhydrous $MgSO_4$, filtered and concentrated under reduced pressure. Purification by silica gel chromatography provided Intermediate 33-f as purple foam.

Synthesis of Intermediate 34-b:

Scheme 34

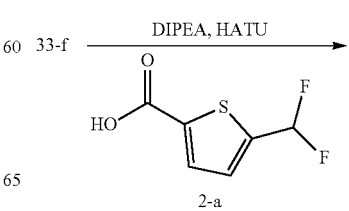

Step 1: Intermediate 33-b

To a solution of 4-iodo-3-nitroaniline 33-a (1.0 g, 3.8 mmol) in dichloromethane (10.8 ml) were sequentially added DIPEA (1320 μl, 7.6 mmol) and methanesulfonyl chloride (650 μl, 8.4 mmol). After the addition was completed, the reaction was stirred for 1 hour at room temperature. A saturated aqueous solution of ammonium chloride and ethyl acetate were added; the organic layer was separated, washed with brine, dried over anhydrous $MgSO_4$,

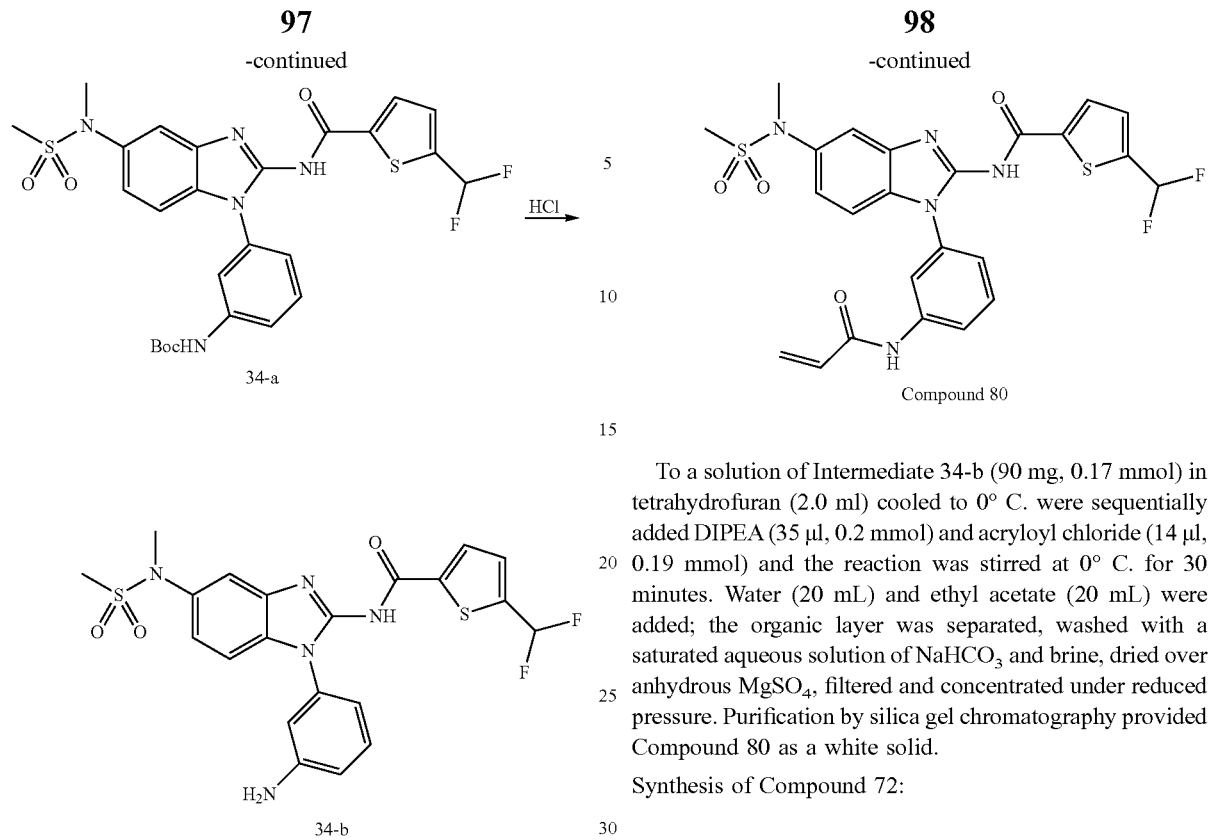

34-a 34-b

Step 1: Intermediate 34-a

To a solution of 5-(difluoromethyl)thiophene-2-carboxylic acid 2-a (52 mg, 0.3 mmol) in DMF (1.3 ml) was added HATU (132 mg, 0.3 mmol) and after stirring for 30 minutes a solution of Intermediate 33-f (115 mg, 0.3 mmol) and DIPEA (140 µl, 0.8 mmol) in DMF (2.0 ml) was added dropwise. The reaction was then stirred at room temperature for 1 day. A saturated aqueous solution of ammonium chloride and ethyl acetate were then added, the organic layer was separated, washed with a saturated aqueous solution of ammonium chloride and brine, dried over anhydrous MgSO$_4$, filtered and concentrated under reduced pressure. Purification by silica gel chromatography provided Intermediate 34-a as a purple solid.

Step 2: Intermediate 34-b

To a solution of Intermediate 34-a (100 mg, 0.17 mmol) in MeOH (2 mL) was added 4N solution of HCl in dioxane (3 ml) and the reaction was stirred at room temperature for 30 minutes. Volatiles were removed under reduced pressure. Diethyl ether was added to the residue; a precipitate formed and was collected by filtration to provide Intermediate 34-b.HCl as a purple solid.

Synthesis of Compound 80:

Scheme 35

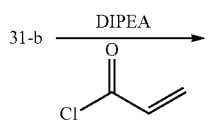

Compound 80

To a solution of Intermediate 34-b (90 mg, 0.17 mmol) in tetrahydrofuran (2.0 ml) cooled to 0° C. were sequentially added DIPEA (35 µl, 0.2 mmol) and acryloyl chloride (14 µl, 0.19 mmol) and the reaction was stirred at 0° C. for 30 minutes. Water (20 mL) and ethyl acetate (20 mL) were added; the organic layer was separated, washed with a saturated aqueous solution of NaHCO$_3$ and brine, dried over anhydrous MgSO$_4$, filtered and concentrated under reduced pressure. Purification by silica gel chromatography provided Compound 80 as a white solid.

Synthesis of Compound 72:

Scheme 36

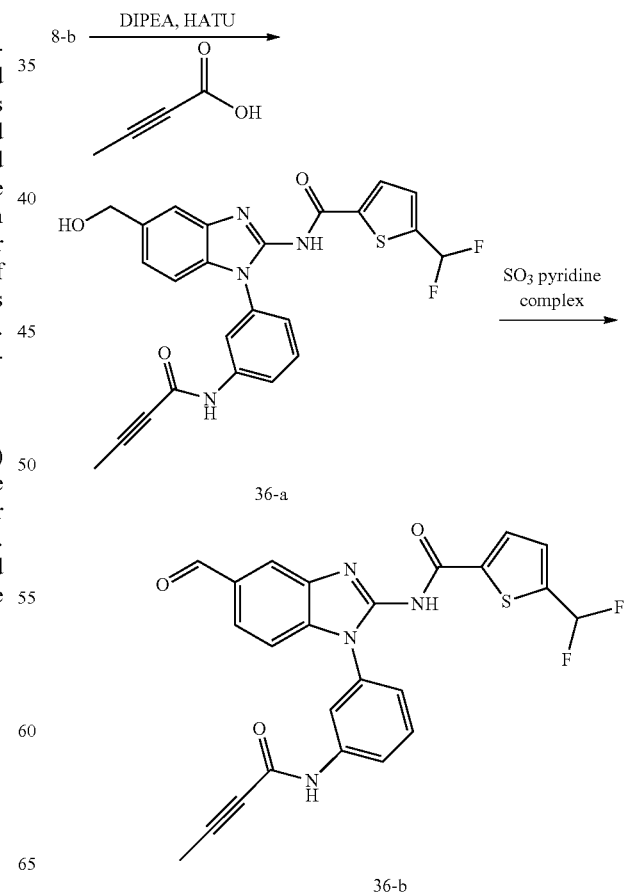

36-a 36-b

-continued

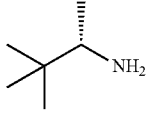

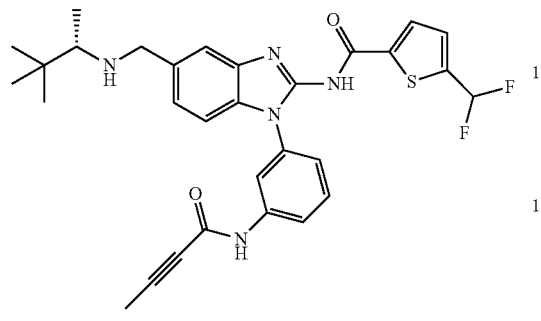

Compound 72

Step 1: Intermediate 36-a

To a solution of Intermediate 8-b (100 mg, 0.2 mmol) and but-2-ynoic acid (20 mg, 0.2 mmol) in DMF (2.2 ml) were sequentially added DIPEA (194 μl, 1.1 mmol) and HATU (110 mg, 0.3 mmol) and the reaction was then stirred at room temperature for 1 day. A saturated aqueous solution of ammonium chloride and ethyl acetate were then added, the organic layer was separated, washed with a saturated aqueous solution of ammonium chloride and brine, dried over anhydrous MgSO$_4$, filtered and concentrated under reduced pressure. Purification by silica gel chromatography provided Intermediate 36-a as an off-white solid.

Step 2: Intermediate 36-b

To a solution of Intermediate 36-a (50 mg, 0.1 mmol) in THF (1.0 ml) and DMSO (74 μl) cooled to 0° C. were sequentially added DIPEA (73 μl, 0.4 mmol) and a solution of SO$_3$ pyridine complex (50 mg, 0.3 mmol) in DMSO (1 mL). The mixture was then stirred at 0'C for 1 day. Volatiles were removed under reduced pressure, water was added, a precipitate formed and was collected by filtration, washed with water and dried under vacuum to provide Intermediate 36-b as beige solid.

Step 3: Compound 72

To a solution of Intermediate 36-b (25 mg, 0.05 mmol) and (S)-3,3-dimethylbutan-2-amine (7.1 μl, 0.05 mmol) in THF (1.0 ml) and acetonitrile (1 ml), were sequentially added 1 drop of acetic acid and sodium triacetoxyborohydride (17 mg, 0.07 mmol) and the reaction was stirred overnight at room temperature. Volatiles were removed under reduced pressure. Purification by silica gel chromatography provided Compound 72 as white solid.

Compounds 83 and 84 were prepared in a similar manner to Compound 72 by replacing

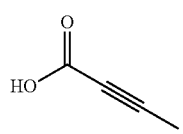

with

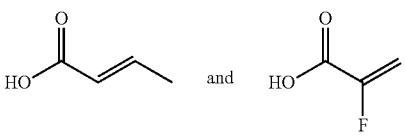

respectively.

Synthesis of Compound 78:

Scheme 37

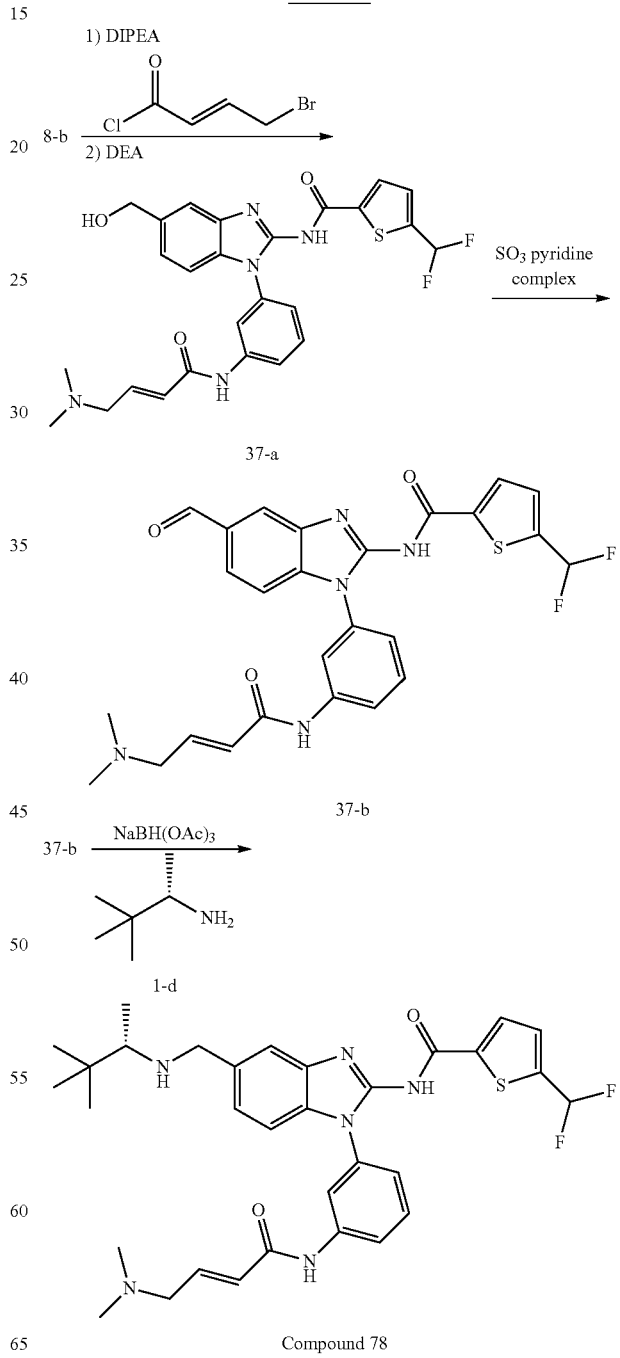

Compound 78

Step 1: Intermediate 37-a

To a solution of (E)-4-bromobut-2-enoic acid (51 mg, 0.3 mmol) in dichloromethane cooled to −78° C. were sequentially added oxalyl chloride (49 μl, 0.6 mmol) and DMF (217 μl, 2.8 mmol) and the reaction was stirred at −78° C. for 1 hour. Volatiles were removed under reduced pressure and the residue was dissolved in dichloromethane.

To a solution of Intermediate 8-b (116 mg, 0.3 mmol) in THF (2 ml) cooled to −78° C. was added DIPEA (245 μl, 1.4 mmol) and a solution of (E)-4-bromobut-2-enoyl chloride prepared above and after completion, a 1M solution of dimethylamine in THF (2.8 ml, 2.8 mmol) was added and the reaction was then stirred at room temperature overnight. Volatiles were removed under reduced pressure. Purification by silica gel chromatography provided Intermediate 37-a as a beige solid.

Step 2: Intermediate 37-b

To a solution of Intermediate 37-a (110 mg, 0.2 mmol) in THF (1.7 ml) and DMSO (122 μl) cooled to 0° C. were sequentially added DIPEA (150 μl, 0.8 mmol) and a solution of $SO_3$ pyridine complex (82 mg, 0.5 mmol) in DMSO (1 mL). The mixture was then stirred at 0'C overnight. Volatiles were removed under reduced pressure, water was added, a precipitate formed and was collected by filtration, washed with water and dried under vacuum to provide Intermediate 37-b as a beige solid.

Step 3: Compound 78

To a solution of Intermediate 37-b (90 mg, 0.2 mmol) and (S)-3,3-dimethylbutan-2-amine 1-d (27 μl, 0.2 mmol) in 1,2-dichloroethane (2.0 ml), were sequentially added 1 drop of acetic acid and sodium triacetoxyborohydride (55 mg, 0.2 mmol) and the reaction was stirred overnight at room temperature. Volatiles were removed under reduced pressure. Purification by silica gel chromatography provided Compound 78 as white solid.

Synthesis of Intermediate 38-e:

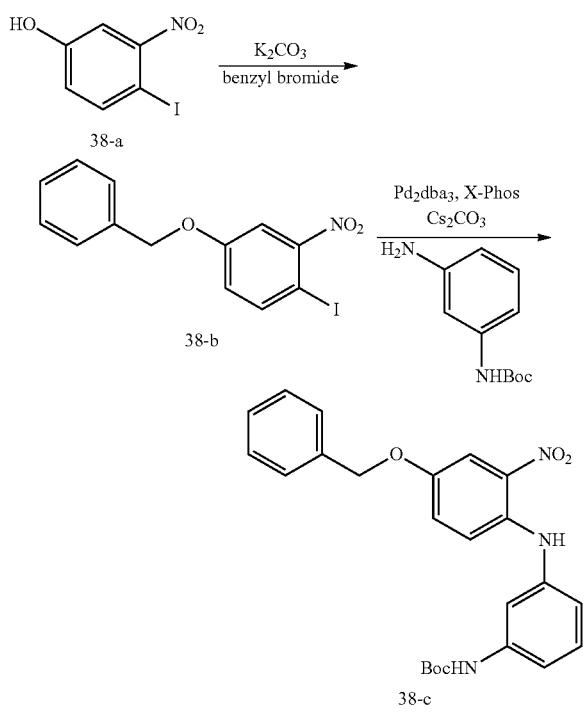

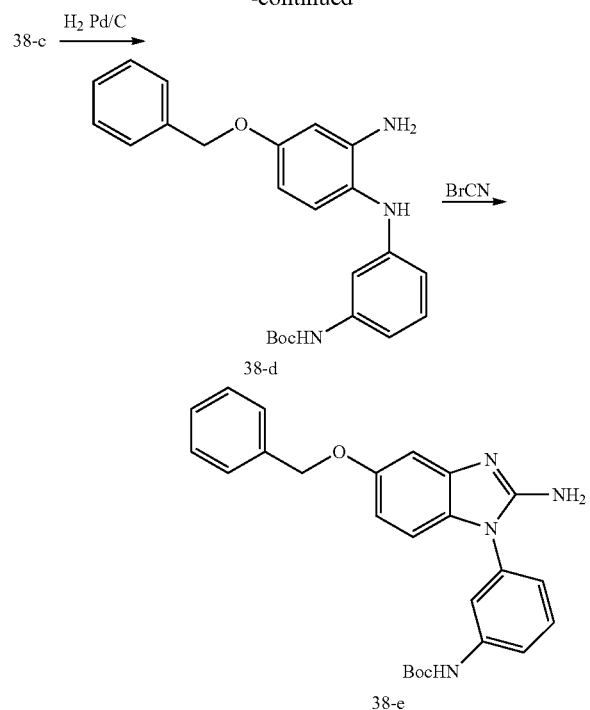

Step 1: Intermediate 38-b

To a solution of 4-iodo-3-nitrophenol 38-a (3.0 g, 11.3 mmol) in acetone (113 ml) was added potassium carbonate (1.5 g, 11.3 mmol) and after stirring for 5 minutes, benzyl bromide (1.3 ml, 11.3 mmol) was added. The reaction was stirred at reflux for 4 hours, then cooled to room temperature and filtered. Volatiles were removed under reduced pressure to provide Intermediate 38-b as a yellow solid.

Step 2: Intermediate 38-c

A degassed solution of tert-butyl 3-aminophenylcarbamate 1-b (1.2 g, 5.9 mmol), Intermediate 38-b (1.0 g, 2.8 mmol), $Cs_2CO_3$ (2.7 g, 8.4 mmol), X-Phos (100 mg, 0.3 mmol) and $Pd_2dba_3$ (129 mg, 0.14 mmol) in dioxane (28.1 ml) was heated at 100° C. for 1 day and then cooled to room temperature. A saturated aqueous solution of ammonium chloride and ethyl acetate were then added, the organic layer was separated, washed with a saturated aqueous solution of ammonium chloride and brine, dried over anhydrous $MgSO_4$, filtered and concentrated under reduced pressure. Purification by silica gel chromatography provided Intermediate 38-c as a red solid.

Step 3: Intermediate 38-d

To a solution of Intermediate 38-c (1.2 g, 2.8 mmol) in methanol (28.0 ml) and stirred under nitrogen was added 10% Pd/C (298 mg, 0.28 mmol). The reaction mixture was purged with $H_2$ and stirred for 1 day under $H_2$. The reaction was then filtered through celite and the filtrate was concentrated in vacuo. Purification by silica gel chromatography provided Intermediate 38-d as purple solid.

Step 4: Intermediate 38-e

To a solution of Intermediate 38-d (470 mg, 1.1 mmol) in EtOH (11.6 ml) was added cyanogen bromide (184 mg, 1.7 mmol) and the reaction was stirred for 6 hours at room temperature. Volatiles were removed under reduced pressure. A saturated aqueous solution of ammonium chloride and ethyl acetate were then added to the residue, the organic layer was separated, washed with a saturated aqueous solution of NaHCO₃ and brine, dried over anhydrous MgSO₄, filtered and concentrated under reduced pressure to provide Intermediate 38-e as a purple solid.

Synthesis of Intermediate 39-b:

Scheme 39

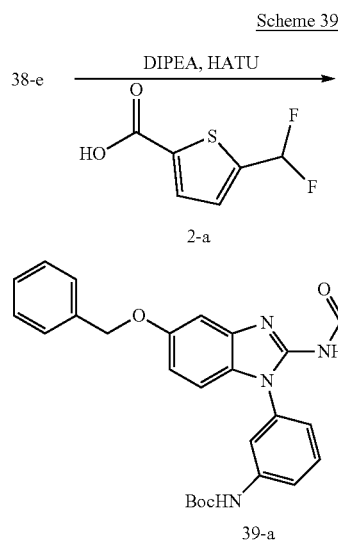

Step 1: Intermediate 39-a

To a solution of 5-(difluoromethyl)thiophene-2-carboxylic acid 2-a (214 mg, 1.2 mmol) in DMF (10.0 ml) cooled to 0° C. was added HATU (494 mg, 1.3 mmol) and after stirring for 30 minutes a solution of Intermediate 38-e (430 mg, 1.0 mmol) and DIPEA (523 µl, 3.0 mmol) in DMF (2.0 ml) was added dropwise. The reaction was then stirred at room temperature for 1 day. A saturated aqueous solution of ammonium chloride and ethyl acetate were then added, the organic layer was separated, washed with a saturated aqueous solution of ammonium chloride and brine, dried over anhydrous MgSO₄, filtered and concentrated under reduced pressure. Purification by silica gel chromatography provided Intermediate 39-a as a purple solid.

Step 2: Intermediate 39-b

To a solution of Intermediate 39-a (100 mg, 0.1 mmol) in dichloromethane (1.0 ml) was added TFA (1.0 ml, 13.1 mmol) at 0° C. and the solution was stirred at room temperature for 30 minutes. Volatiles were removed under reduced pressure to provide Intermediate 39-b.TFA as a beige oil.

Synthesis of Compound 79

Scheme 40

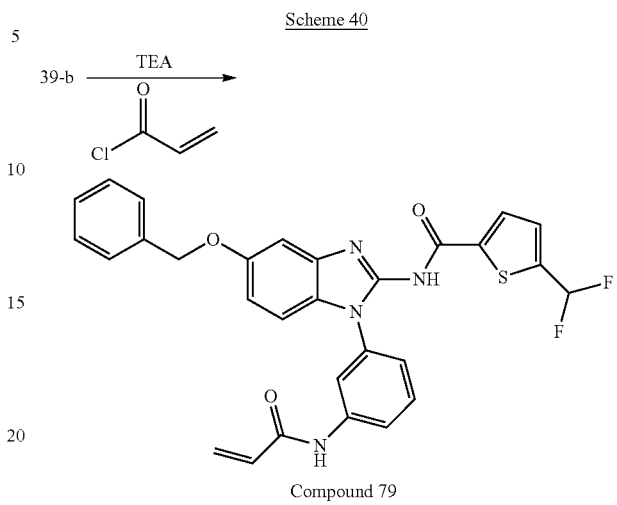

To a solution of Intermediate 39-b.TFA (25 mg, 0.05 mmol) in tetrahydrofuran (510 µl) cooled to 0° C. were sequentially added DIPEA (89 µl, 0.5 mmol) and acryloyl chloride (8.2 µl, 0.1 mmol) and the reaction was stirred at 0° C. for 30 minutes. Water (20 mL) and ethyl acetate (20 mL) were added; the organic layer was separated, washed with a saturated aqueous solution of NaHCO₃ and brine, dried over anhydrous MgSO₄, filtered and concentrated under reduced pressure. Purification by silica gel chromatography provided Compound 79 as an off-white solid.

Synthesis of Intermediate 41-e:

Scheme 41

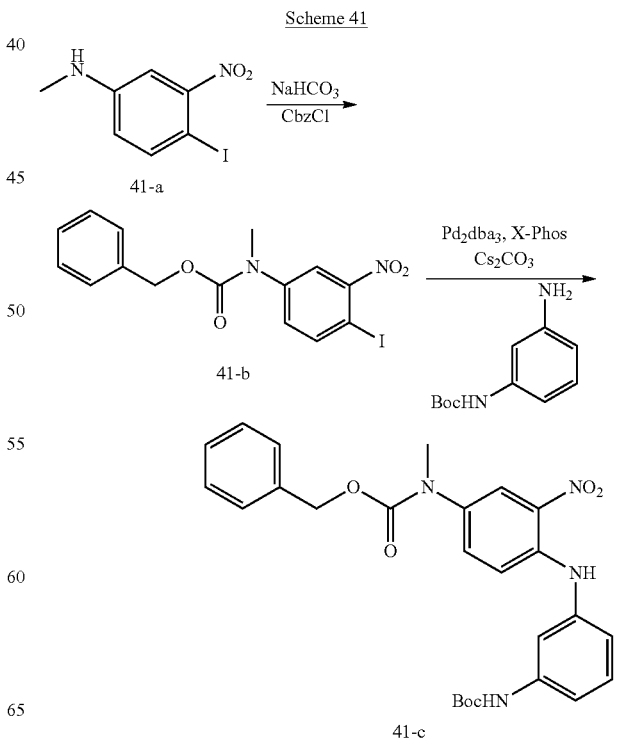

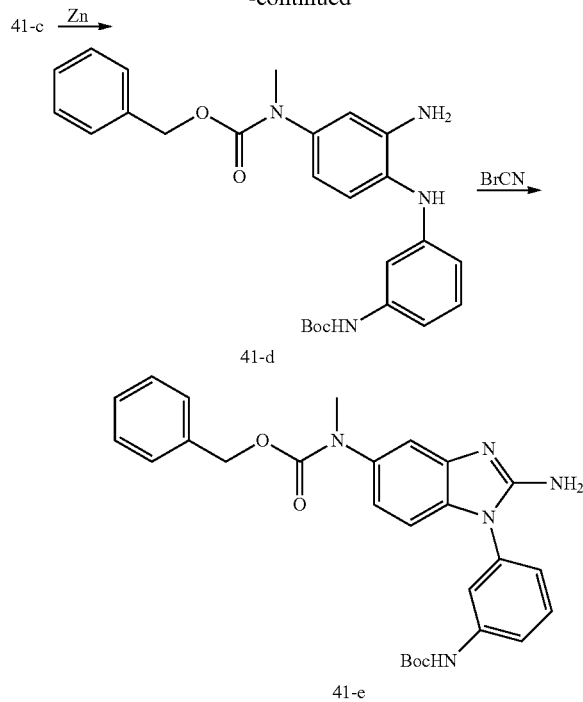

Step 1: Intermediate 41-b

To a solution of Intermediate 41-a (1.4 g, 5.0 mmol) in dichloromethane (25 ml) were sequentially added a saturated aqueous solution of NaHCO$_3$ (25.0 ml) and benzyl chloroformate (1.4 ml, 10.1 mmol) and the reaction was then stirred at room temperature until completion. A saturated aqueous ammonium chloride solution and ethyl acetate were added; the organic layer was separated, washed with a saturated aqueous solution of ammonium chloride and brine, dried over anhydrous MgSO$_4$, filtered and concentrated under reduced pressure to provide Intermediate 41-b as a yellow solid.

Step 2: Intermediate 41-c

A degassed solution of tert-butyl 3-aminophenylcarbamate 1-b (2.1 g, 10.2 mmol), Intermediate 41-b (2.0 g, 4.8 mmol), Cs$_2$CO$_3$ (4.7 g, 14.6 mmol), X-Phos (231 mg, 0.5 mmol) and Pd$_2$dba$_3$ (222 mg, 0.24 mmol) in dioxane (48.5 ml) was heated at 100° C. for 1 day and then cooled to room temperature. A saturated aqueous solution of ammonium chloride and ethyl acetate were then added, the organic layer was separated, washed with a saturated aqueous solution of ammonium chloride and brine, dried over anhydrous MgSO$_4$, filtered and concentrated under reduced pressure. Purification by silica gel chromatography provided Intermediate 41-c as yellow solid.

Step 3: Intermediate 41-d

To a solution of Intermediate 41-c (820 mg, 1.7 mmol) in MeOH (11.1 ml) was added a saturated aqueous solution of ammonium chloride (3.0 ml) and zinc dust (544 mg, 8.3 mmol) portion wise. The reaction was then stirred at 50° C. for 2 hours, then cooled to room temperature and filtered over celite. The filtrate was concentrated under reduced pressure. Diethyl ether and a saturated aqueous solution of ammonium chloride were added to the residue, the organic layer was separated, washed with brine, dried over MgSO$_4$, filtered and concentrated under reduced pressure. Purification by silica gel chromatography provided Intermediate 41-d as a purple solid.

Step 3: Intermediate 41-e

To a solution of Intermediate 41-d (468 mg, 1.0 mmol) in EtOH (20.2 ml) was added cyanogen bromide (129 mg, 1.2 mmol) and the reaction was stirred overnight at room temperature. Volatiles were removed under reduced pressure. A saturated aqueous solution of ammonium chloride and ethyl acetate were then added to the residue, the organic layer was separated, washed with a saturated aqueous solution of NaHCO$_3$ and brine, dried over anhydrous MgSO$_4$, filtered and concentrated under reduced pressure to provide Intermediate 41-e as a purple foam.

Synthesis of Intermediate 42-b:

Scheme 42

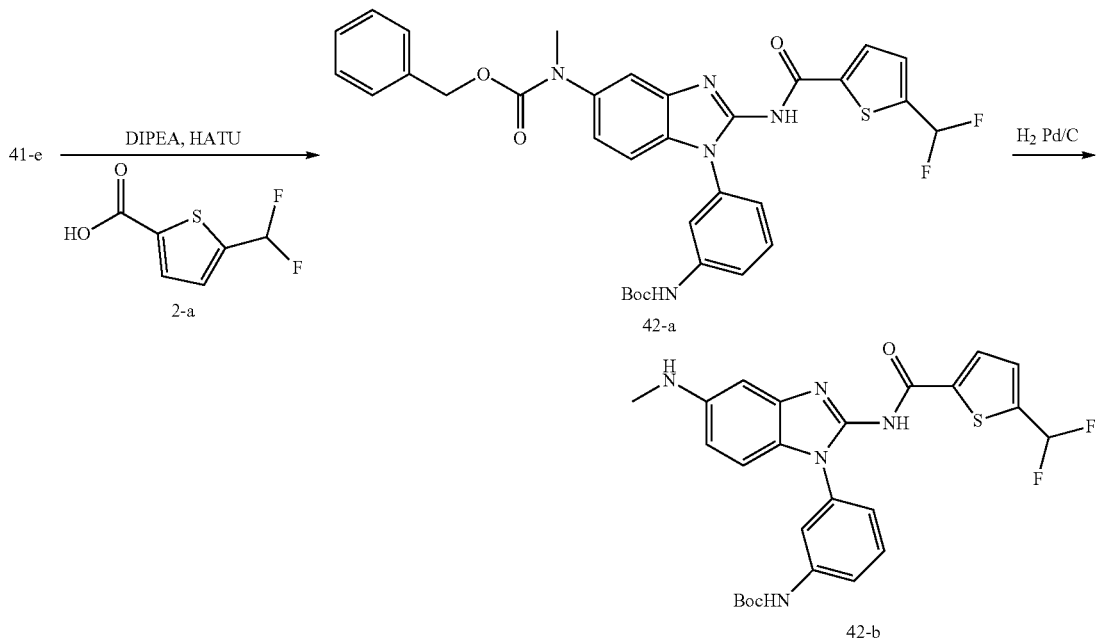

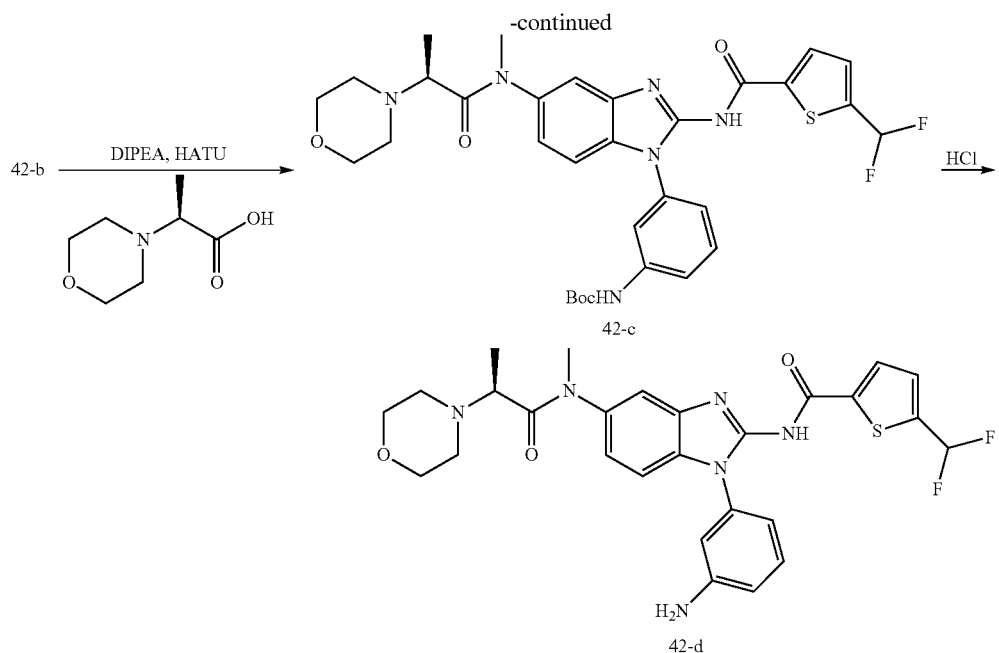

To a solution of 5-(difluoromethyl)thiophene-2-carboxylic acid 2-a (67 mg, 0.4 mmol) in DMF (1.7 ml) cooled to 0° C. was added HATU (168 mg, 0.4 mmol) and after stirring for 30 minutes a solution of Intermediate 41-e (166 mg, 0.3 mmol) and DIPEA (178 μl, 0.4 mmol) in DMF (2.0 ml) was added dropwise. The reaction was then stirred at room temperature for 4 hours. A saturated aqueous solution of ammonium chloride and ethyl acetate were then added, the organic layer was separated, washed with a saturated aqueous solution of ammonium chloride and brine, dried over anhydrous MgSO$_4$, filtered and concentrated under reduced pressure. Purification by silica gel chromatography provided Intermediate 42-a as a purple solid.

Step 2: Intermediate 42-b

To a solution of Intermediate 42-a (125 mg, 0.2 mmol) in methanol (5.0 ml) and stirred under nitrogen was added 10% Pd/C (41 mg, 0.02 mmol). The reaction mixture was purged with H$_2$ and stirred for 24 hours under H$_2$. The reaction was then filtered through celite and the filtrate was concentrated under reduced pressure to provide Intermediate 42-b as beige solid.

Step 3: Intermediate 42-c

To a solution of (S)-2-morpholinopropanoic acid (15 mg, 0.09 mmol) in DMF (400 μl) cooled to 0° C. was added HATU (41 mg, 0.1 mmol) and after stirring for 30 minutes a solution of Intermediate 42-b (52 mg, 0.08 mmol) and DIPEA (43 μl, 0.2 mmol) in DMF (2.0 ml) was added dropwise. The reaction was then stirred at room temperature for 1 week. A saturated aqueous solution of ammonium chloride and ethyl acetate were then added, the organic layer was separated, washed with a saturated aqueous solution of ammonium chloride and brine, dried over anhydrous MgSO$_4$, filtered and concentrated under reduced pressure. Purification by silica gel chromatography provided Intermediate 42-c as a purple solid.

Step 4: Intermediate 42-d

To a solution of Intermediate 42-c (50 mg, 0.07 mmol) in methanol (2.0 ml) was added a 4.0 N solution of HCl in 1,4-dioxane (5 ml, 20 mmol) at 0° C. and the solution was stirred at room temperature for 30 minutes. Volatiles were removed under reduced pressure to provide Intermediate 42-d.HCl as a purple solid.

Synthesis of Compound 77:

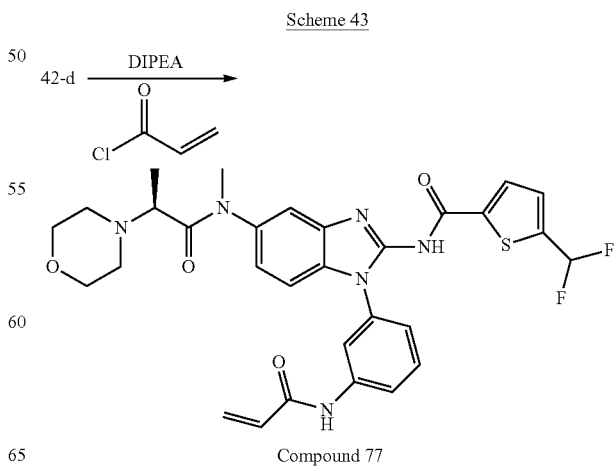

Scheme 43

Compound 77

To a solution of Intermediate 42-d.HCl (50 mg, 0.08 mmol) in tetrahydrofuran (2.0 ml) cooled to 0° C. were sequentially added DIPEA (69 µl, 0.4 mmol) and acryloyl chloride (6.4 µl, 0.08 mmol) and the reaction was stirred at 0° C. for 30 minutes. Water and ethyl acetate were added; the organic layer was separated, washed with a saturated aqueous solution of NaHCO₃ and brine, dried over anhydrous MgSO₄, filtered and concentrated under reduced pressure. Purification by silica gel chromatography provided Compound 77 as a white solid.

Synthesis of Compound 36:

Scheme 44

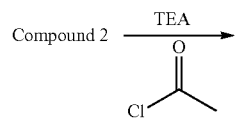

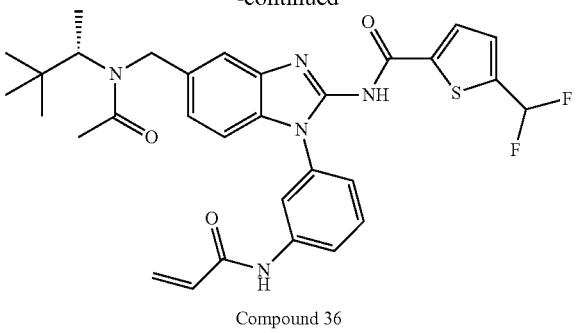

Compound 36

To a solution of compound 2 (80 mg, 0.1 mmol) in dichloromethane (1.5 ml) cooled to 0'C were sequentially added TEA (201 µl, 1.5 mmol) and acetyl chloride (12 µl, 0.17 mmol) and the reaction was then stirred at room temperature for 3 hours. Water (20 mL) and ethyl acetate (20 mL) were added; the organic layer was separated, washed with a saturated aqueous solution of NaHCO₃ and brine, dried over anhydrous MgSO₄, filtered and concentrated under reduced pressure. Purification by silica gel chromatography provided Compound 36 as a beige solid.

TABLE 1

Example Compounds of Formula I

| Compound | Structure | MS (m/z) |
|---|---|---|
| 1 | [structure] | [M + H]⁺ = 530.3 |
| 2 | [structure] | [M + H]⁺ = 552.3 |

TABLE 1-continued

Example Compounds of Formula I

| Compound | Structure | MS (m/z) |
|---|---|---|
| 3 | 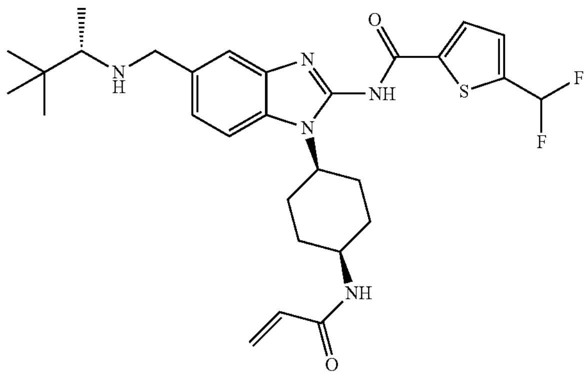 [SMILES: C=CC(=O)N[C@H]1CC[C@@H](n2c(NC(=O)c3ccc(C(F)F)s3)nc3cc(CN[C@@H](C)C(C)(C)C)ccc32)CC1] | [M + H]⁺ = 558.3 |
| 4 | 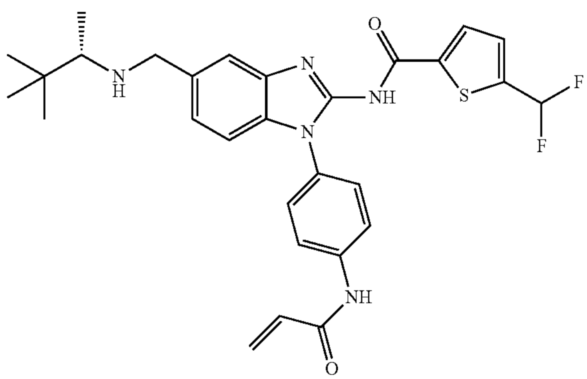 [SMILES: C=CC(=O)Nc1ccc(-n2c(NC(=O)c3ccc(C(F)F)s3)nc3cc(CN[C@@H](C)C(C)(C)C)ccc32)cc1] | [M + H]⁺ = 552.4 |
| 5 | 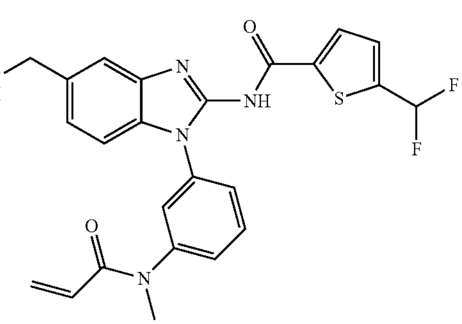 | [M + H]⁺ = 566.4 |
| 6 | 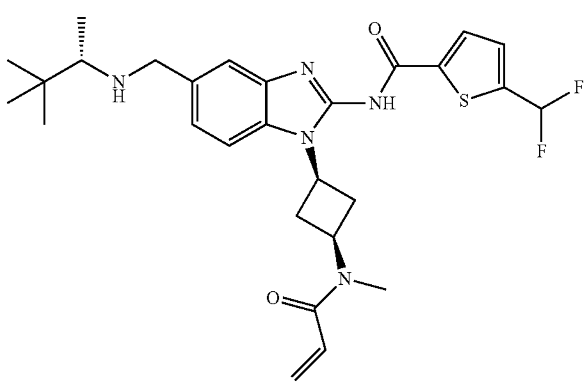 [SMILES: C=CC(=O)N(C)[C@H]1C[C@@H](n2c(NC(=O)c3ccc(C(F)F)s3)nc3cc(CN[C@@H](C)C(C)(C)C)ccc32)C1] | [M + H]⁺ = 544.3 |

TABLE 1-continued
Example Compounds of Formula I
| Compound | Structure | MS (m/z) |
|---|---|---|
| 7 | 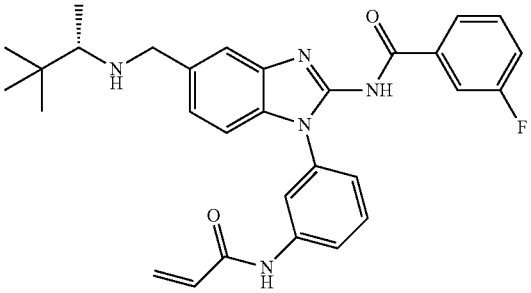 [SMILES: C=CC(=O)Nc1cccc(-n2c(NC(=O)c3cccc(F)c3)nc3cc(CN[C@@H](C)C(C)(C)C)ccc32)c1] | [M + H]⁺ = 514.3 |
| 8 | 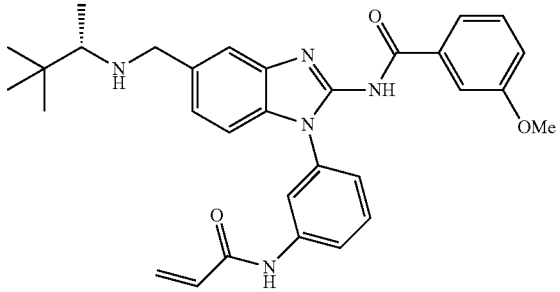 [SMILES: C=CC(=O)Nc1cccc(-n2c(NC(=O)c3cccc(OC)c3)nc3cc(CN[C@@H](C)C(C)(C)C)ccc32)c1] | [M + H]⁺ = 526.4 |
| 9 | 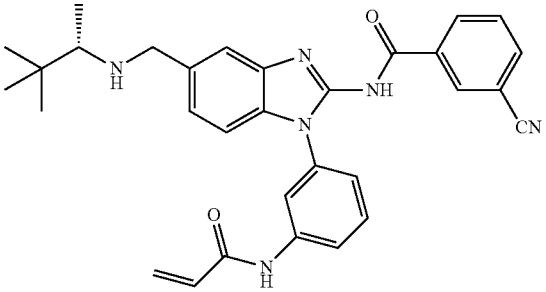 [SMILES: C=CC(=O)Nc1cccc(-n2c(NC(=O)c3cccc(C#N)c3)nc3cc(CN[C@@H](C)C(C)(C)C)ccc32)c1] | [M + H]⁺ = 521.2 |
| 10 | 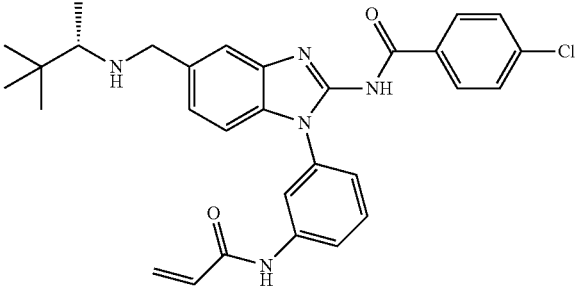 [SMILES: C=CC(=O)Nc1cccc(-n2c(NC(=O)c3ccc(Cl)cc3)nc3cc(CN[C@@H](C)C(C)(C)C)ccc32)c1] | [M + H]⁺ = 530.6 |
| 11 | 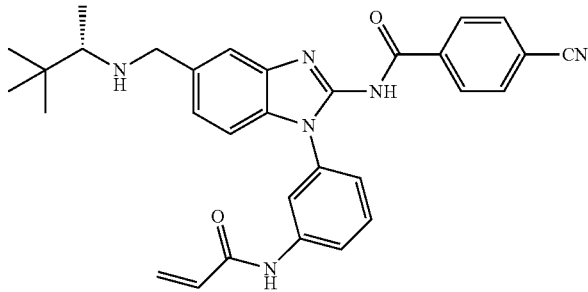 [SMILES: C=CC(=O)Nc1cccc(-n2c(NC(=O)c3ccc(C#N)cc3)nc3cc(CN[C@@H](C)C(C)(C)C)ccc32)c1] | [M + H]⁺ = 521.4 |

TABLE 1-continued
Example Compounds of Formula I
| Compound | Structure | MS (m/z) |
|---|---|---|
| 12 | 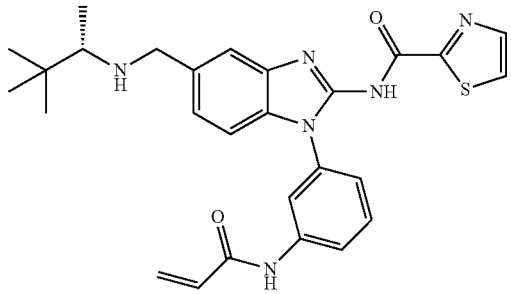 [SMILES: C=CC(=O)Nc1cccc(-n2c(NC(=O)c3nccs3)nc3cc(CN[C@@H](C)C(C)(C)C)ccc32)c1] | [M + H]⁺ = 503.3 |
| 13 | 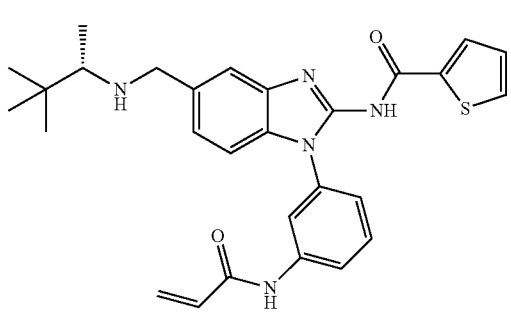 [SMILES: C=CC(=O)Nc1cccc(-n2c(NC(=O)c3cccs3)nc3cc(CN[C@@H](C)C(C)(C)C)ccc32)c1] | [M + H]⁺ = 502.3 |
| 14 | 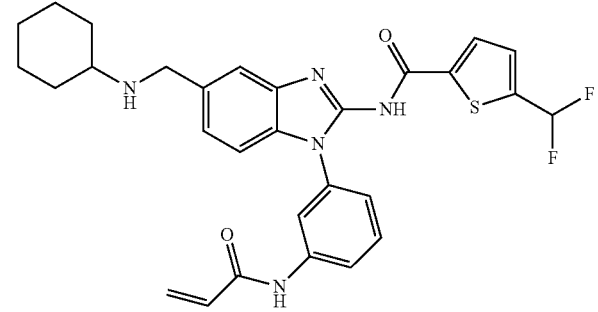 [SMILES: C=CC(=O)Nc1cccc(-n2c(NC(=O)c3ccc(C(F)F)s3)nc3cc(CNC4CCCCC4)ccc32)c1] | [M + H]⁺ = 550.3 |
| 15 | 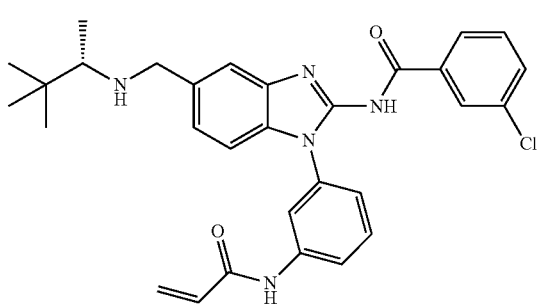 [SMILES: C=CC(=O)Nc1cccc(-n2c(NC(=O)c3cccc(Cl)c3)nc3cc(CN[C@@H](C)C(C)(C)C)ccc32)c1] | [M + H]⁺ = 531.2 |
| 16 | 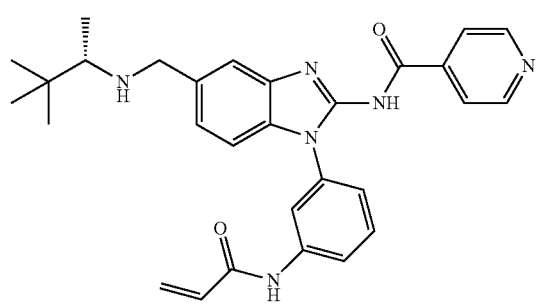 [SMILES: C=CC(=O)Nc1cccc(-n2c(NC(=O)c3ccncc3)nc3cc(CN[C@@H](C)C(C)(C)C)ccc32)c1] | [M + H]⁺ = 497.2 |

TABLE 1-continued

Example Compounds of Formula I

| Compound | Structure | MS (m/z) |
|---|---|---|
| 17 | 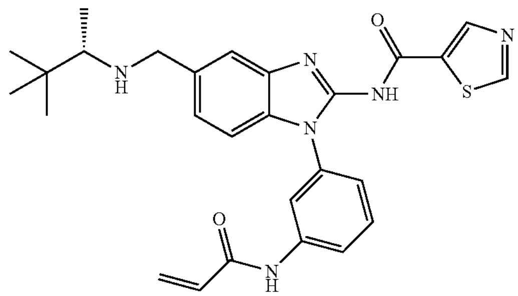 [SMILES: C=CC(=O)Nc1cccc(-n2c(NC(=O)c3cncs3)nc3cc(CN[C@@H](C)C(C)(C)C)ccc32)c1] | [M + H]⁺ = 503.3 |
| 18 | 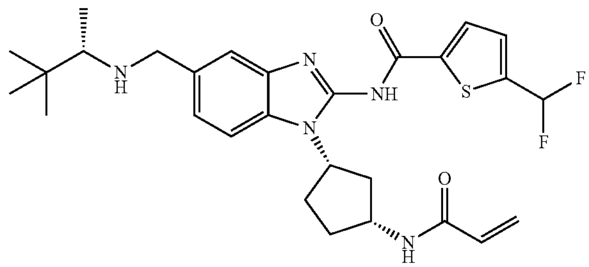 [SMILES: C=CC(=O)N[C@@H]1CC[C@H](n2c(NC(=O)c3ccc(C(F)F)s3)nc3cc(CN[C@@H](C)C(C)(C)C)ccc32)C1] | [M + H]⁺ = 544.2 |
| 19 | 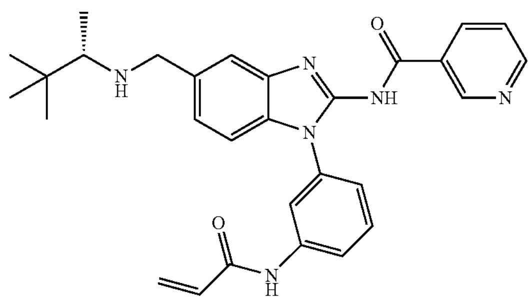 | [M + H]⁺ = 497.4 |
| 20 | 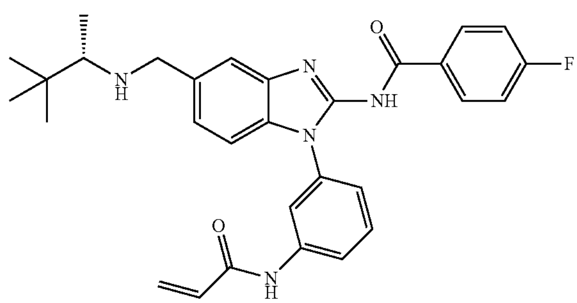 [SMILES: C=CC(=O)Nc1cccc(-n2c(NC(=O)c3ccc(F)cc3)nc3cc(CN[C@@H](C)C(C)(C)C)ccc32)c1] | [M + H]⁺ = 514.3 |
| 21 | 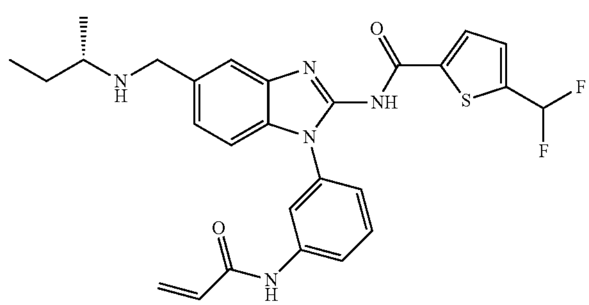 [SMILES: C=CC(=O)Nc1cccc(-n2c(NC(=O)c3ccc(C(F)F)s3)nc3cc(CN[C@@H](C)CC)ccc32)c1] | [M + H]⁺ = 524.3 |

TABLE 1-continued
Example Compounds of Formula I
| Compound | Structure | MS (m/z) |
|---|---|---|
| 22 | 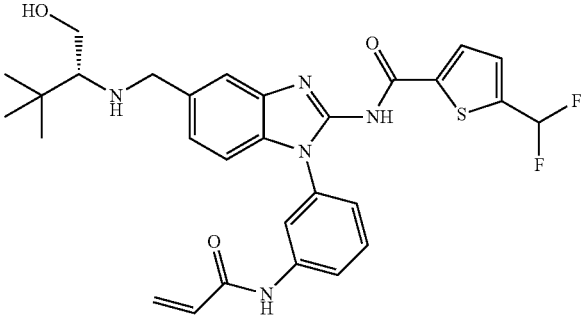 [SMILES: C=CC(=O)Nc1cccc(-n2c(NC(=O)c3ccc(C(F)F)s3)nc3cc(CN[C@@H](CO)C(C)(C)C)ccc32)c1] | [M + H]⁺ = 568.3 |
| 23 | 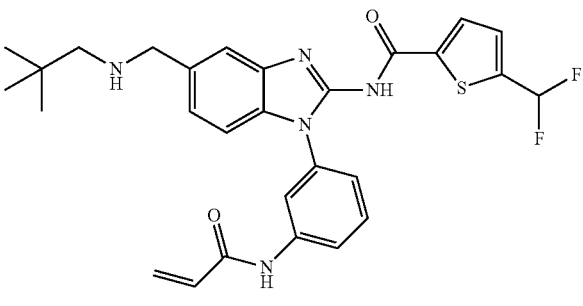 [SMILES: C=CC(=O)Nc1cccc(-n2c(NC(=O)c3ccc(C(F)F)s3)nc3cc(CNCC(C)(C)C)ccc32)c1] | [M + H]⁺ = 538.3 |
| 24 | 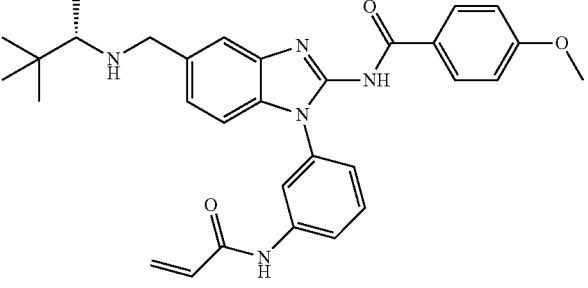 | [M + H]⁺ = 526.4 |
| 25 | 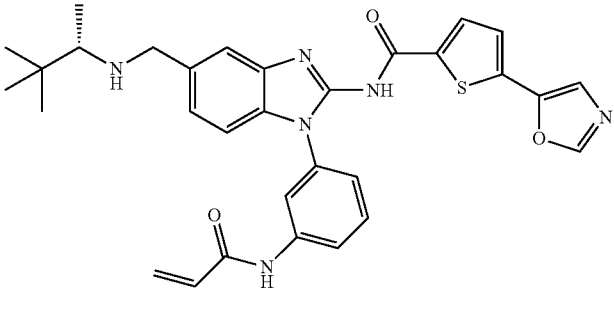 [SMILES: C=CC(=O)Nc1cccc(-n2c(NC(=O)c3ccc(-c4cnco4)s3)nc3cc(CN[C@@H](C)C(C)(C)C)ccc32)c1] | [M + H]⁺ = 569.3 |
| 26 | 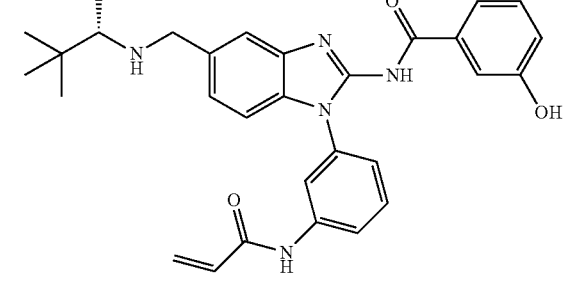 | [M + H]⁺ = 512.3 |

TABLE 1-continued
Example Compounds of Formula I
| Compound | Structure | MS (m/z) |
|---|---|---|
| 27 | 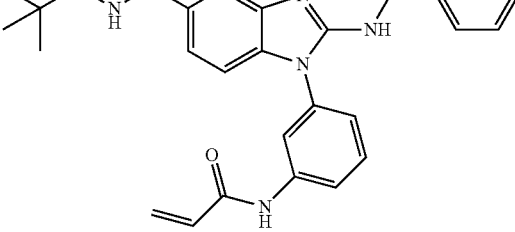 | [M + H]⁺ = 497.3 |
| 28 | 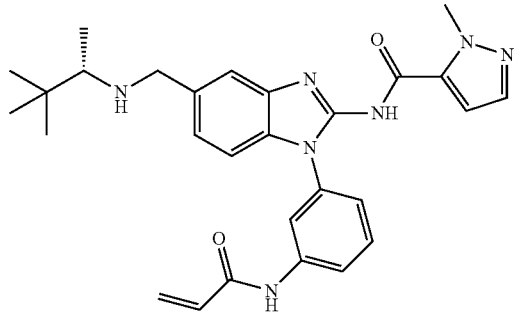 [SMILES: C=CC(=O)Nc1cccc(-n2c(NC(=O)c3ccnn3C)nc3cc(CN[C@@H](C)C(C)(C)C)ccc32)c1] | [M + H]⁺ = 500.4 |
| 29 | 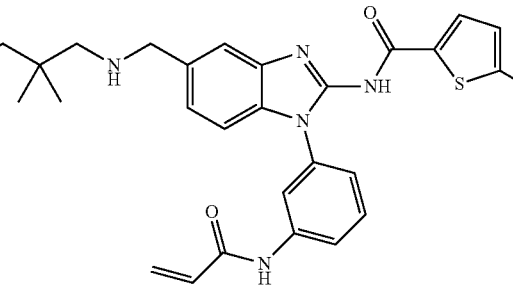 | [M + H]⁺ = 554.3 |
| 30 | 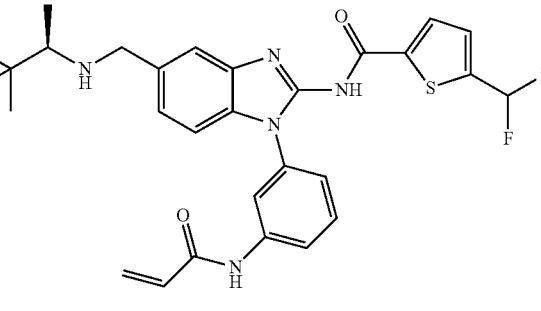 | [M + H]⁺ = 552.3 |
| 31 | 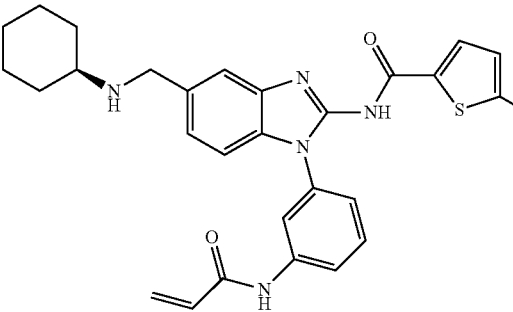 | [M + H]⁺ = 566.3 |

TABLE 1-continued

Example Compounds of Formula I

| Compound | Structure | MS (m/z) |
|---|---|---|
| 32 | 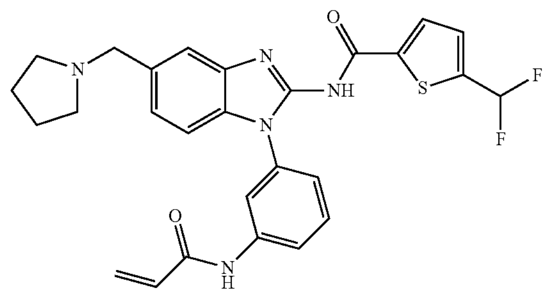 [SMILES: C=CC(=O)Nc1cccc(-n2c(NC(=O)c3ccc(C(F)F)s3)nc3cc(CN4CCCC4)ccc32)c1] | [M + H]⁺ = 522.3 |
| 33 | 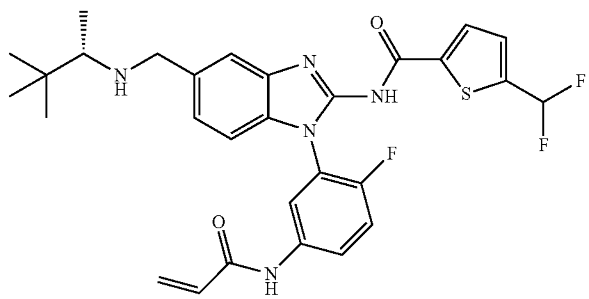 [SMILES: C=CC(=O)Nc1ccc(F)c(-n2c(NC(=O)c3ccc(C(F)F)s3)nc3cc(CN[C@@H](C)C(C)(C)C)ccc32)c1] | [M + H]⁺ = 570.3 |
| 34 | 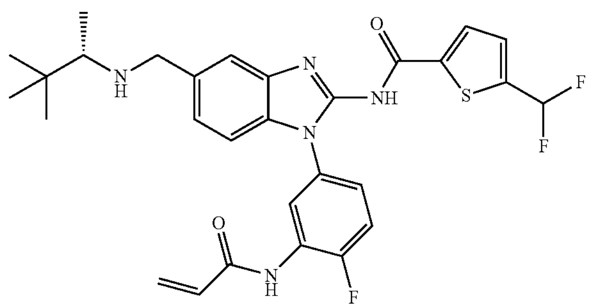 [SMILES: C=CC(=O)Nc1cc(-n2c(NC(=O)c3ccc(C(F)F)s3)nc3cc(CN[C@@H](C)C(C)(C)C)ccc32)ccc1F] | [M + H]⁺ = 570.3 |
| 35 | 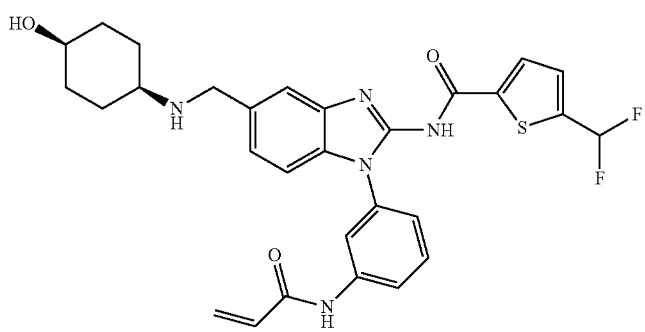 [SMILES: C=CC(=O)Nc1cccc(-n2c(NC(=O)c3ccc(C(F)F)s3)nc3cc(CN[C@H]4CC[C@@H](O)CC4)ccc32)c1] | [M + H]⁺ = 566.3 |
| 36 | 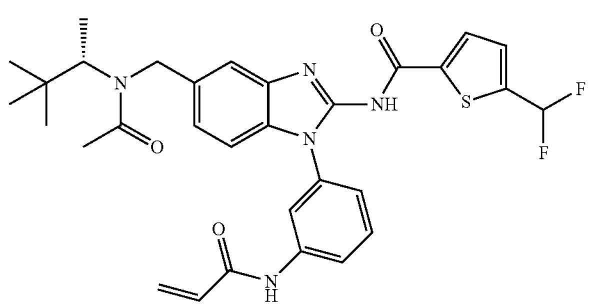 [SMILES: C=CC(=O)Nc1cccc(-n2c(NC(=O)c3ccc(C(F)F)s3)nc3cc(CN(C(C)=O)[C@@H](C)C(C)(C)C)ccc32)c1] | [M + H]⁺ = 594.3 |

TABLE 1-continued

Example Compounds of Formula I

| Compound | Structure | MS (m/z) |
|---|---|---|
| 37 | 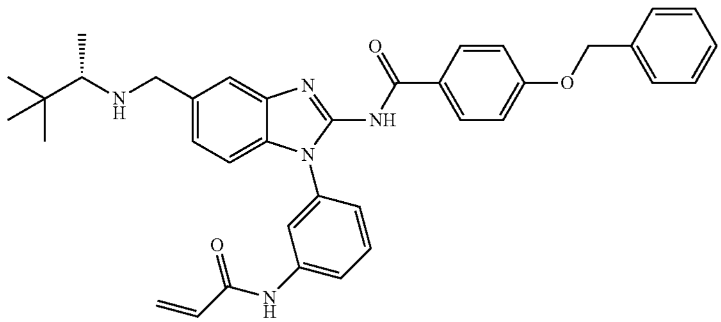 [SMILES: C=CC(=O)Nc1cccc(-n2c(NC(=O)c3ccc(OCc4ccccc4)cc3)nc3cc(CN[C@@H](C)C(C)(C)C)ccc32)c1] | [M + H]⁺ = 602.3 |
| 38 | 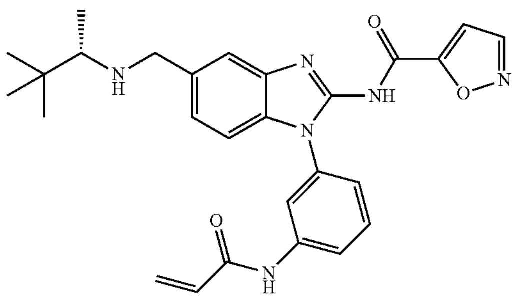 | [M + H]⁺ = 487.3 |
| 39 | 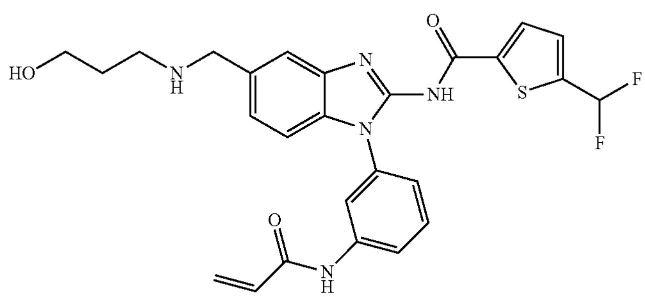 [SMILES: C=CC(=O)Nc1cccc(-n2c(NC(=O)c3ccc(C(F)F)s3)nc3cc(CNCCCO)ccc32)c1] | [M + H]⁺ = 526.7 |
| 40 | 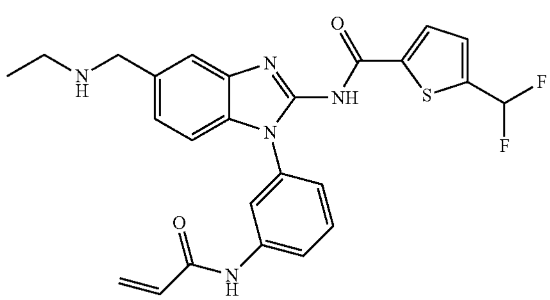 [SMILES: C=CC(=O)Nc1cccc(-n2c(NC(=O)c3ccc(C(F)F)s3)nc3cc(CNCC)ccc32)c1] | [M + H]⁺ = 496.2 |
| 41 | 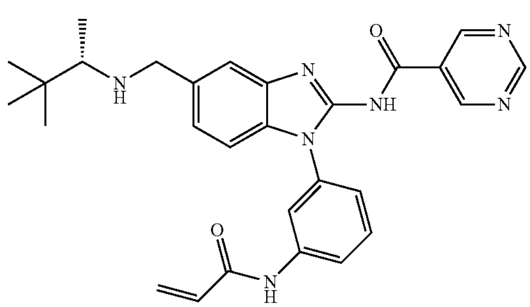 [SMILES: C=CC(=O)Nc1cccc(-n2c(NC(=O)c3cncnc3)nc3cc(CN[C@@H](C)C(C)(C)C)ccc32)c1] | [M + H]⁺ = 498.3 |

TABLE 1-continued

Example Compounds of Formula I

| Compound | Structure | MS (m/z) |
|---|---|---|
| 42 | 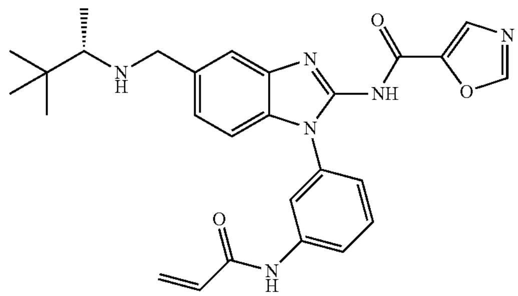 [SMILES: C=CC(=O)Nc1cccc(-n2c(NC(=O)c3cnco3)nc3cc(CN[C@@H](C)C(C)(C)C)ccc32)c1] | [M + H]⁺ = 487.1 |
| 43 | 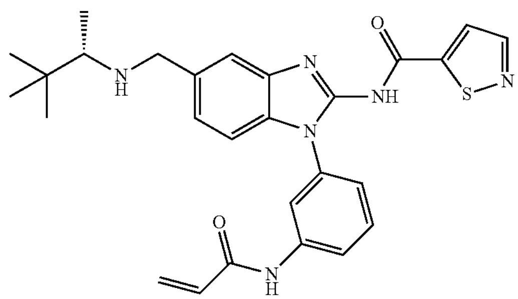 [SMILES: C=CC(=O)Nc1cccc(-n2c(NC(=O)c3ccns3)nc3cc(CN[C@@H](C)C(C)(C)C)ccc32)c1] | [M + H]⁺ = 503.3 |
| 44 | 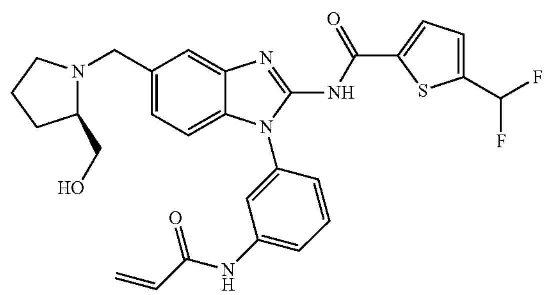 [SMILES: C=CC(=O)Nc1cccc(-n2c(NC(=O)c3ccc(C(F)F)s3)nc3cc(CN4CCC[C@@H]4CO)ccc32)c1] | [M + H]⁺ = 552.3 |
| 45 | 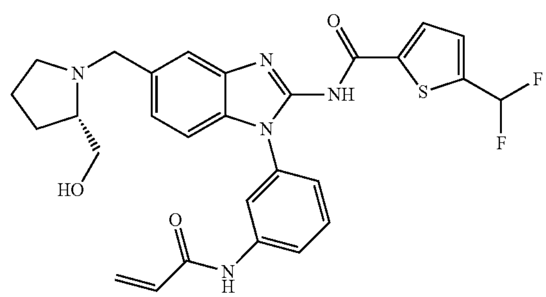 [SMILES: C=CC(=O)Nc1cccc(-n2c(NC(=O)c3ccc(C(F)F)s3)nc3cc(CN4CCC[C@H]4CO)ccc32)c1] | [M + H]⁺ = 552.2 |
| 46 | 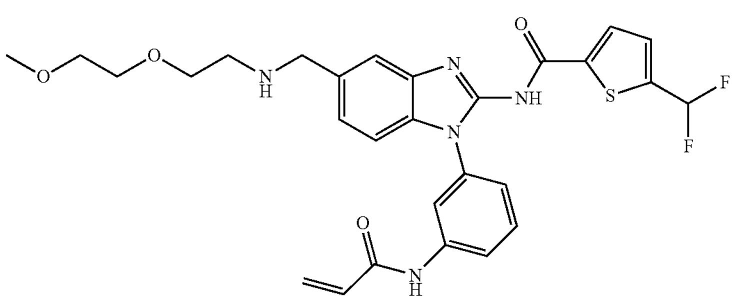 [SMILES: C=CC(=O)Nc1cccc(-n2c(NC(=O)c3ccc(C(F)F)s3)nc3cc(CNCCOCCOC)ccc32)c1] | [M + H]⁺ = 570.2 |

TABLE 1-continued
Example Compounds of Formula I
| Compound | Structure | MS (m/z) |
|---|---|---|
| 47 | 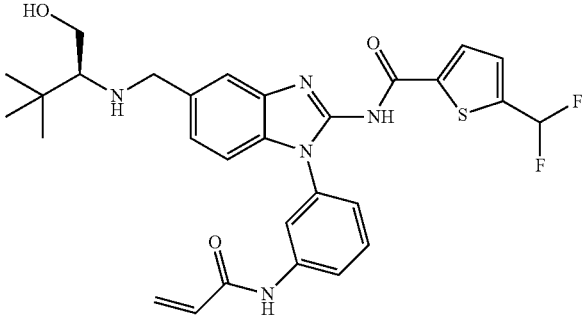 [SMILES: C=CC(=O)Nc1cccc(-n2c(NC(=O)c3ccc(C(F)F)s3)nc3cc(CN[C@H](CO)C(C)(C)C)ccc32)c1] | [M + H]⁺ = 568.2 |
| 48 | 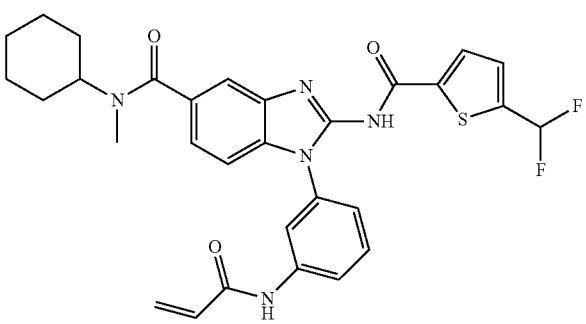 [SMILES: C=CC(=O)Nc1cccc(-n2c(NC(=O)c3ccc(C(F)F)s3)nc3cc(C(=O)N(C)C4CCCCC4)ccc32)c1] | [M + H]⁺ = 578.3 |
| 49 | 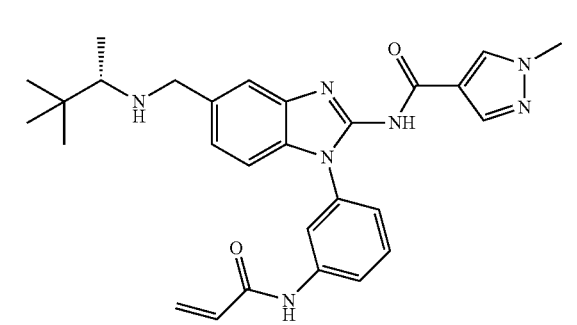 [SMILES: C=CC(=O)Nc1cccc(-n2c(NC(=O)c3cnn(C)c3)nc3cc(CN[C@@H](C)C(C)(C)C)ccc32)c1] | [M + H]⁺ = 500.2 |
| 50 | 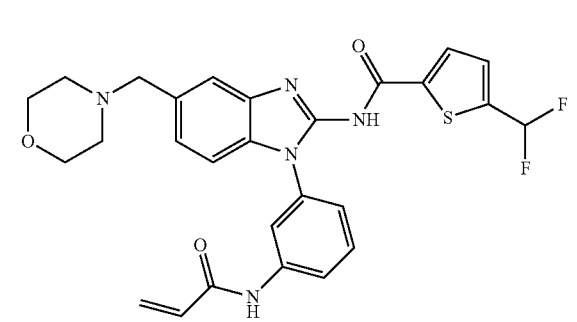 [SMILES: C=CC(=O)Nc1cccc(-n2c(NC(=O)c3ccc(C(F)F)s3)nc3cc(CN4CCOCC4)ccc32)c1] | [M + H]⁺ = 538.2 |

TABLE 1-continued

Example Compounds of Formula I

| Compound | Structure | MS (m/z) |
|---|---|---|
| 51 | 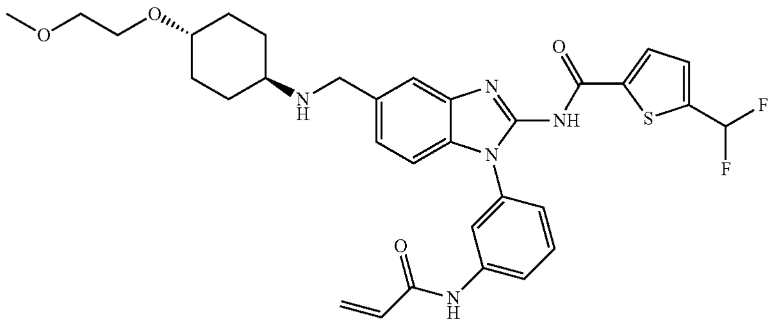 [SMILES: C=CC(=O)Nc1cccc(-n2c(NC(=O)c3ccc(C(F)F)s3)nc3cc(CN[C@H]4CC[C@H](OCCOC)CC4)ccc32)c1] | [M + H]⁺ = 624.1 |
| 52 | 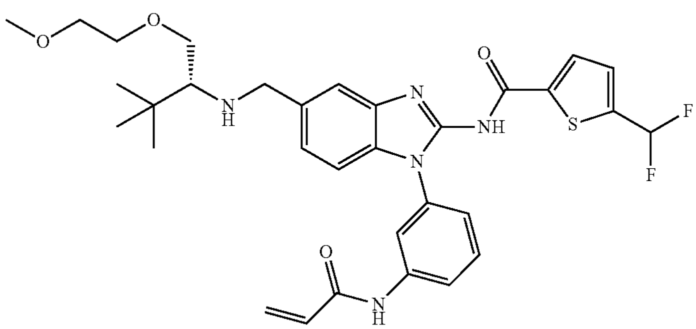 [SMILES: C=CC(=O)Nc1cccc(-n2c(NC(=O)c3ccc(C(F)F)s3)nc3cc(CN[C@@H](COCCOC)C(C)(C)C)ccc32)c1] | [M + H]⁺ = 624.1 |
| 53 | 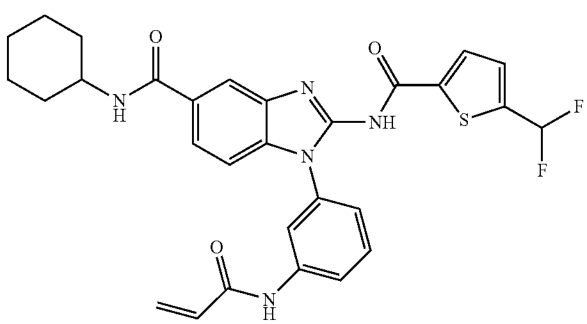 [SMILES: C=CC(=O)Nc1cccc(-n2c(NC(=O)c3ccc(C(F)F)s3)nc3cc(C(=O)NC4CCCCC4)ccc32)c1] | [M + H]⁺ = 564.2 |
| 54 | 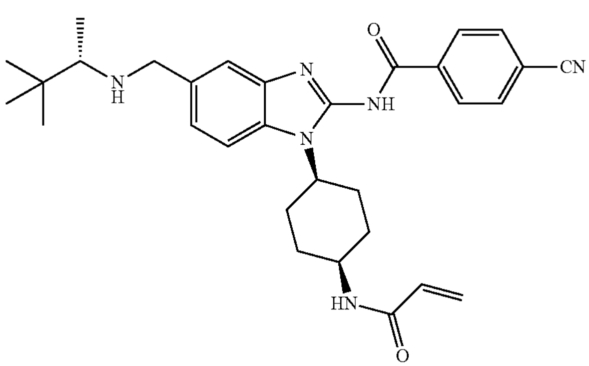 [SMILES: C=CC(=O)N[C@H]1CC[C@@H](n2c(NC(=O)c3ccc(C#N)cc3)nc3cc(CN[C@@H](C)C(C)(C)C)ccc32)CC1] | [M + H]⁺ = 527.4 |

TABLE 1-continued

Example Compounds of Formula I

| Compound | Structure | MS (m/z) |
| --- | --- | --- |
| 55 | 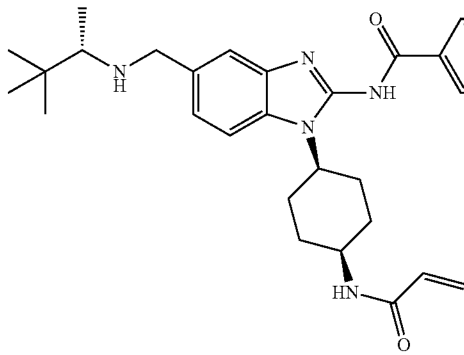 | [M + H]⁺ = 503.4 |
| 56 | 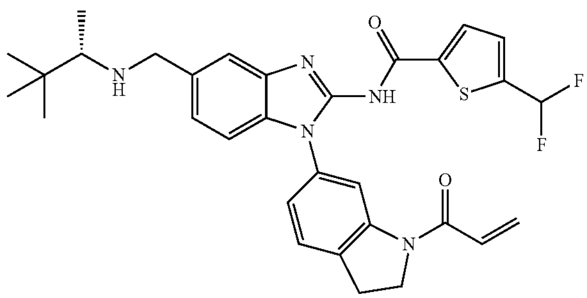 [SMILES: C=CC(=O)N1CCc2ccc(-n3c(NC(=O)c4ccc(C(F)F)s4)nc4cc(CN[C@@H](C)C(C)(C)C)ccc43)cc21] | [M + H]⁺ = 578.3 |
| 57 | 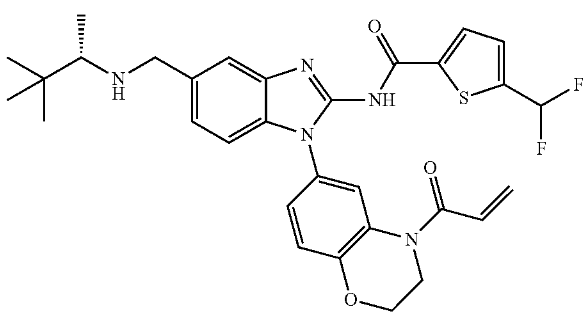 [SMILES: C=CC(=O)N1CCOc2ccc(-n3c(NC(=O)c4ccc(C(F)F)s4)nc4cc(CN[C@@H](C)C(C)(C)C)ccc43)cc21] | [M + H]⁺ = 594.4 |
| 58 | 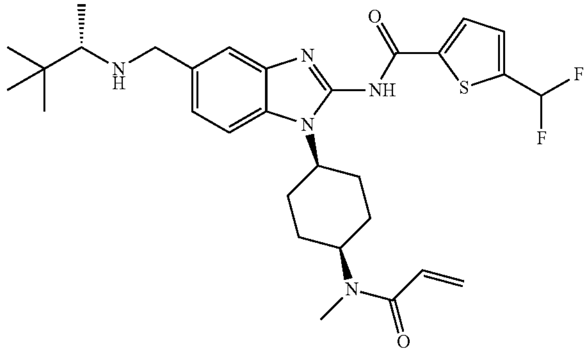 [SMILES: C=CC(=O)N(C)[C@H]1CC[C@@H](n2c(NC(=O)c3ccc(C(F)F)s3)nc3cc(CN[C@@H](C)C(C)(C)C)ccc32)CC1] | [M + H]⁺ = 572.3 |

TABLE 1-continued

Example Compounds of Formula I

| Compound | Structure | MS (m/z) |
|---|---|---|
| 59 | 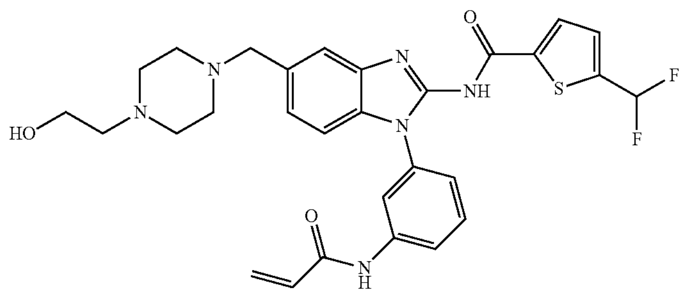 [SMILES: C=CC(=O)Nc1cccc(-n2c(NC(=O)c3ccc(C(F)F)s3)nc3cc(CN4CCN(CCO)CC4)ccc32)c1] | [M + H]⁺ = 581.2 |
| 60 | 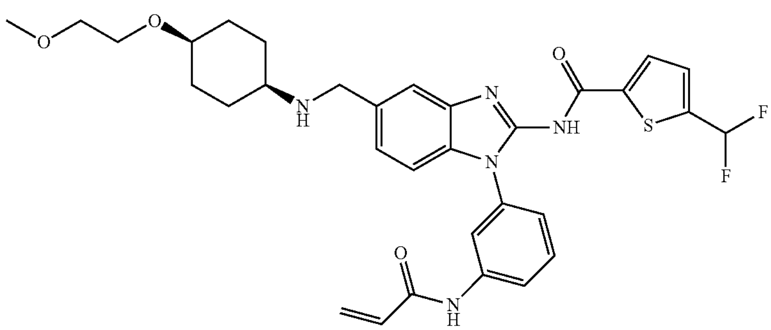 [SMILES: C=CC(=O)Nc1cccc(-n2c(NC(=O)c3ccc(C(F)F)s3)nc3cc(CN[C@H]4CC[C@@H](OCCOC)CC4)ccc32)c1] | [M + H]⁺ = 624.1 |
| 61 | 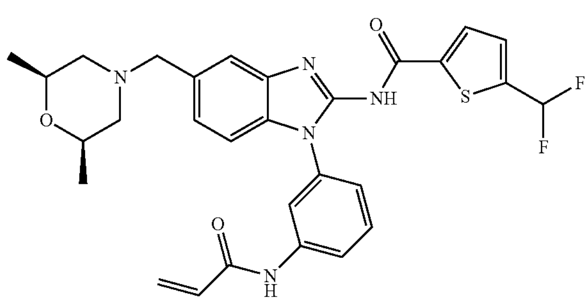 [SMILES: C=CC(=O)Nc1cccc(-n2c(NC(=O)c3ccc(C(F)F)s3)nc3cc(CN4C[C@@H](C)O[C@@H](C)C4)ccc32)c1] | [M + H]⁺ = 566.2 |
| 62 | 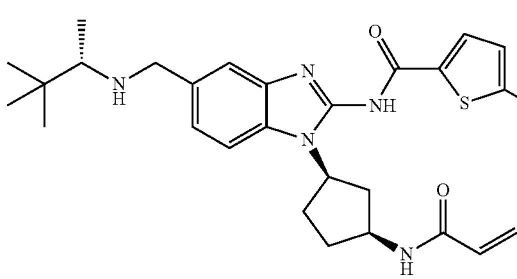 | [M + H]⁺ = 544.2 |

TABLE 1-continued

Example Compounds of Formula I

| Compound | Structure | MS (m/z) |
|---|---|---|
| 63 | 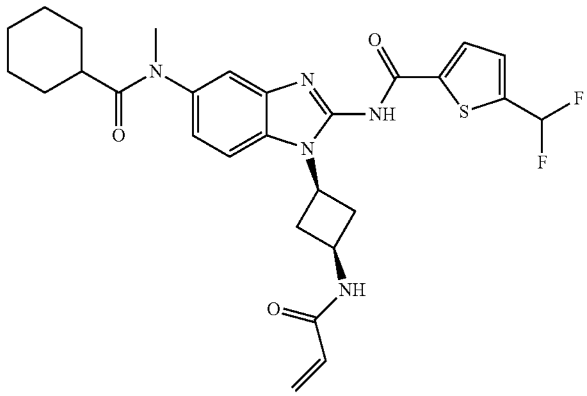 [SMILES: C=CC(=O)N[C@H]1C[C@@H](n2c(NC(=O)c3ccc(C(F)F)s3)nc3cc(N(C)C(=O)C4CCCCC4)ccc32)C1] | [M + H]⁺ = 556.3 |
| 64 | 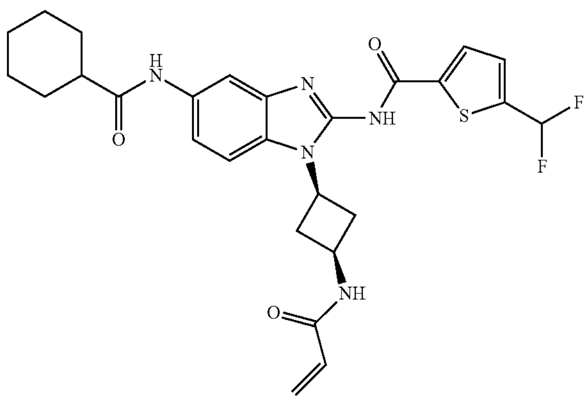 | [M + H]⁺ = 542.2 |
| 65 | 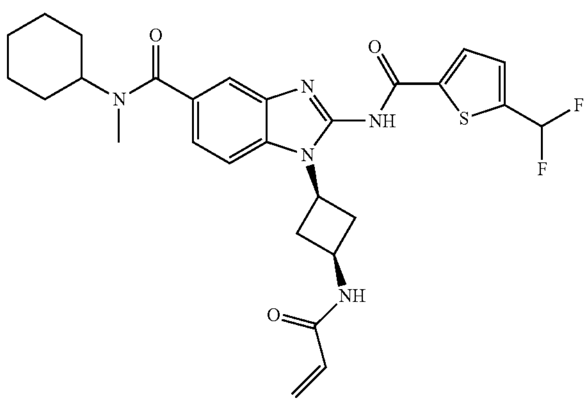 [SMILES: C=CC(=O)N[C@H]1C[C@@H](n2c(NC(=O)c3ccc(C(F)F)s3)nc3cc(C(=O)N(C)C4CCCCC4)ccc32)C1] | [M + H]⁺ = 556.2 |
| 66 | 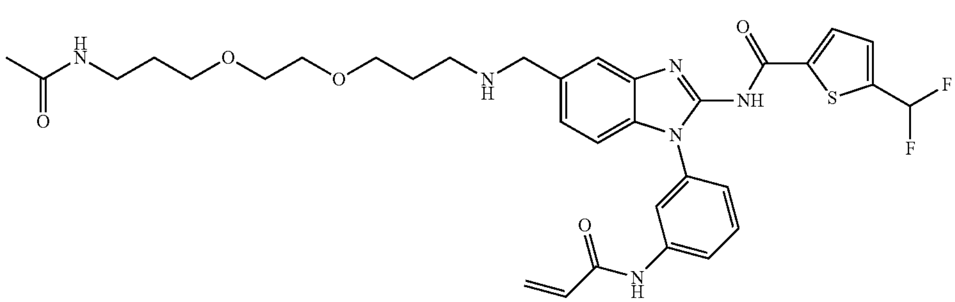 [SMILES: C=CC(=O)Nc1cccc(-n2c(NC(=O)c3ccc(C(F)F)s3)nc3cc(CNCCCOCCOCCCNC(C)=O)ccc32)c1] | [M + H]⁺ = 669.2 |

TABLE 1-continued

Example Compounds of Formula I

| Compound | Structure | MS (m/z) |
|---|---|---|
| 67 | 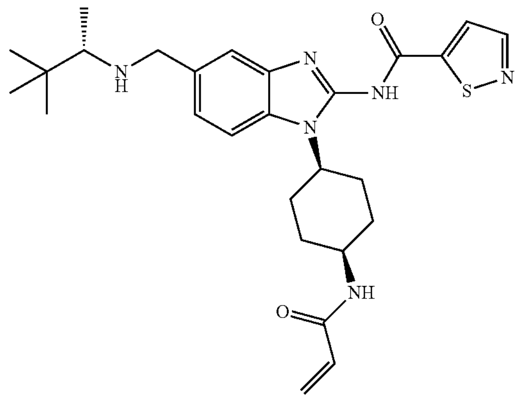 [SMILES: C=CC(=O)N[C@H]1CC[C@@H](n2c(NC(=O)c3ccns3)nc3cc(CN[C@@H](C)C(C)(C)C)ccc32)CC1] | [M + H]⁺ = 509.3 |
| 68 | 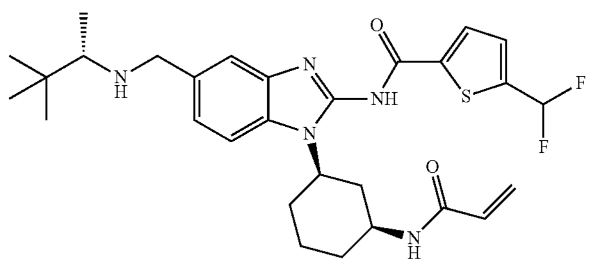 [SMILES: C=CC(=O)N[C@H]1CCC[C@@H](n2c(NC(=O)c3ccc(C(F)F)s3)nc3cc(CN[C@@H](C)C(C)(C)C)ccc32)C1] | [M + H]⁺ = 558.3 |
| 69 | 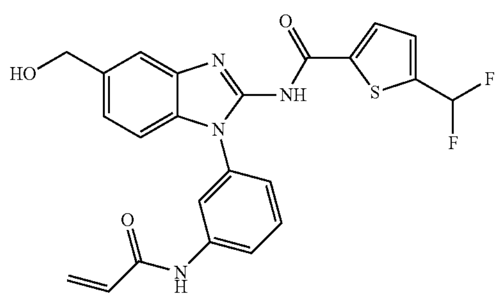 [SMILES: C=CC(=O)Nc1cccc(-n2c(NC(=O)c3ccc(C(F)F)s3)nc3cc(CO)ccc32)c1] | [M + H]⁺ = 469.2 |
| 70 | 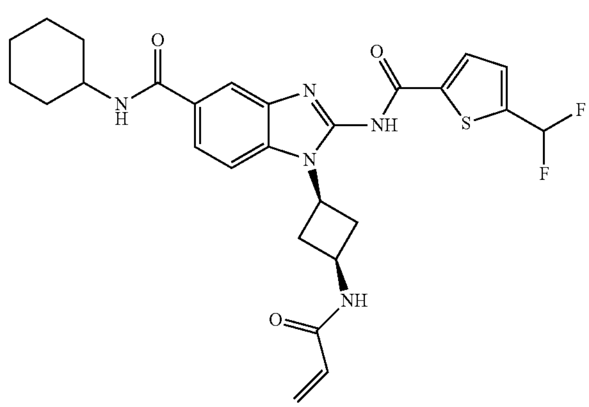 [SMILES: C=CC(=O)N[C@H]1C[C@@H](n2c(NC(=O)c3ccc(C(F)F)s3)nc3cc(C(=O)NC4CCCCC4)ccc32)C1] | [M + H]⁺ = 542.2 |

TABLE 1-continued

Example Compounds of Formula I

| Compound | Structure | MS (m/z) |
|---|---|---|
| 71 | 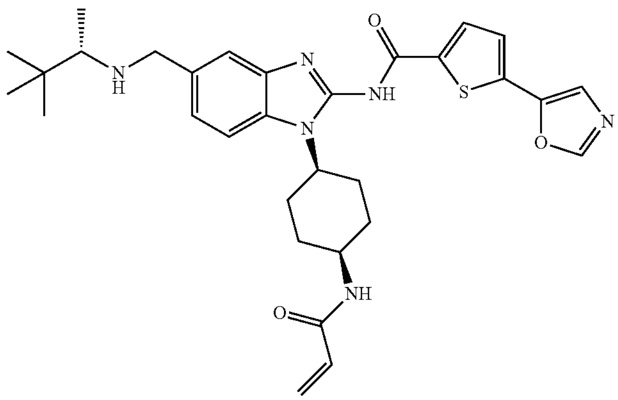 [SMILES: C=CC(=O)N[C@H]1CC[C@@H](n2c(NC(=O)c3ccc(-c4cnco4)s3)nc3cc(CN[C@@H](C)C(C)(C)C)ccc32)CC1] | [M + H]⁺ = 575.4 |
| 72 | 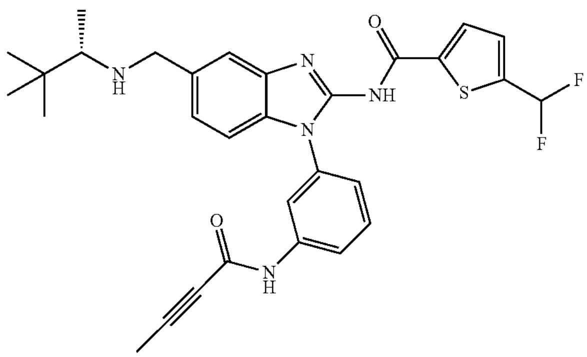 [SMILES: CC#CC(=O)Nc1cccc(-n2c(NC(=O)c3ccc(C(F)F)s3)nc3cc(CN[C@@H](C)C(C)(C)C)ccc32)c1] | [M + H]⁺ = 564.3 |
| 73 | 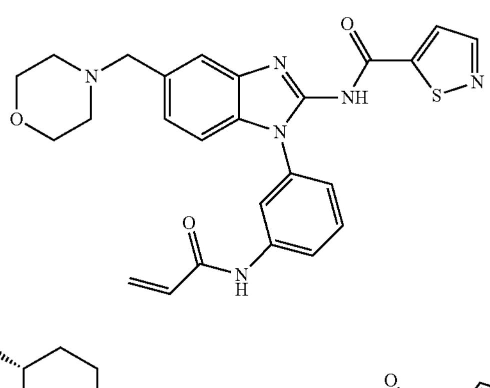 | [M + H]⁺ = 489.2 |
| 74 | 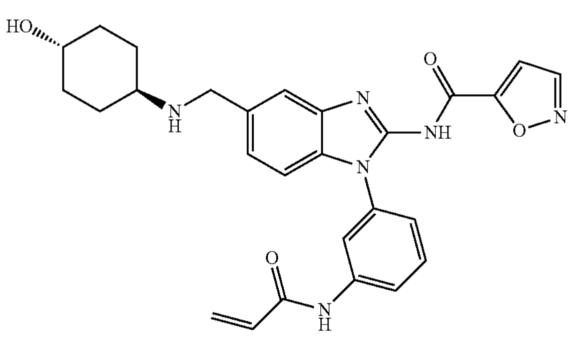 [SMILES: C=CC(=O)Nc1cccc(-n2c(NC(=O)c3ccno3)nc3cc(CN[C@H]4CC[C@H](O)CC4)ccc32)c1] | [M + H]⁺ = 501.2 |

TABLE 1-continued
Example Compounds of Formula I
| Compound | Structure | MS (m/z) |
|---|---|---|
| 75 | 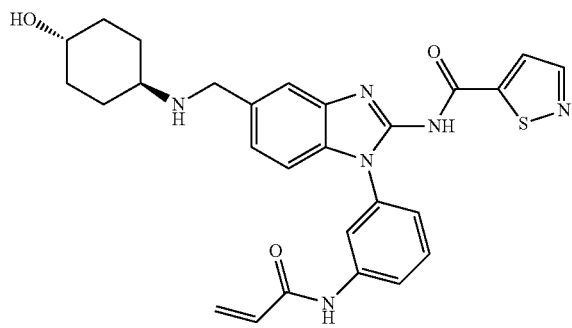 [SMILES: C=CC(=O)Nc1cccc(-n2c(NC(=O)c3ccns3)nc3cc(CN[C@H]4CC[C@H](O)CC4)ccc32)c1] | [M + H]+ = 517.2 |
| 76 | 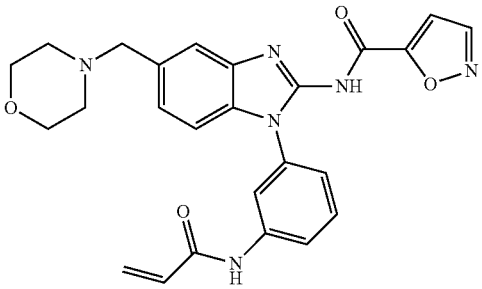 [SMILES: C=CC(=O)Nc1cccc(-n2c(NC(=O)c3ccno3)nc3cc(CN4CCOCC4)ccc32)c1] | [M + H]+ = 473.3 |
| 77 | 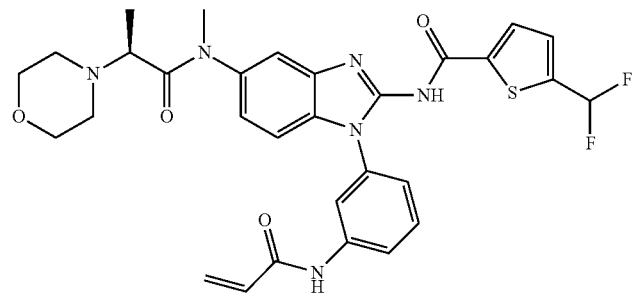 [SMILES: C=CC(=O)Nc1cccc(-n2c(NC(=O)c3ccc(C(F)F)s3)nc3cc(N(C)C(=O)[C@H](C)N4CCOCC4)ccc32)c1] | [M + H]+ = 609.2 |
| 78 | 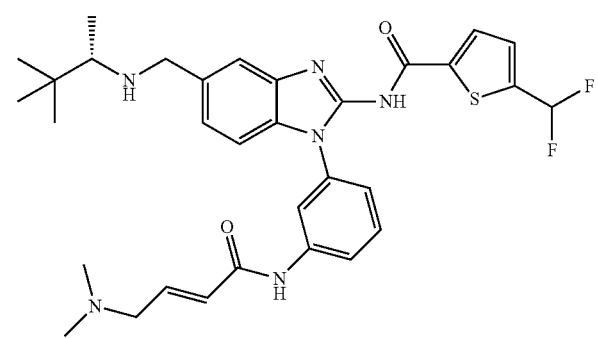 [SMILES: C[C@H](NCc1ccc2c(c1)nc(NC(=O)c1ccc(C(F)F)s1)n2-c1cccc(NC(=O)/C=C/CN(C)C)c1)C(C)(C)C] | [M + H]+ = 609.2 |

TABLE 1-continued

Example Compounds of Formula I

| Compound | Structure | MS (m/z) |
|---|---|---|
| 79 | 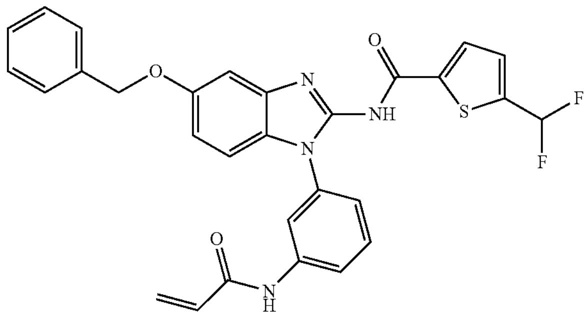 [SMILES: C=CC(=O)Nc1cccc(-n2c(NC(=O)c3ccc(C(F)F)s3)nc3cc(OCc4ccccc4)ccc32)c1] | [M + H]⁺ = 545.1 |
| 80 | 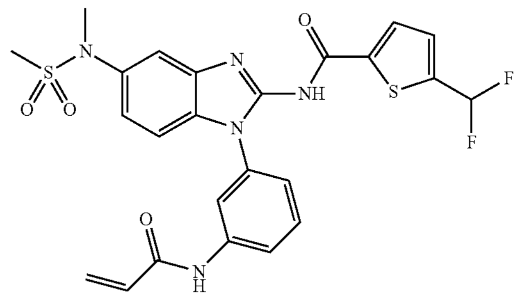 [SMILES: C=CC(=O)Nc1cccc(-n2c(NC(=O)c3ccc(C(F)F)s3)nc3cc(N(C)S(C)(=O)=O)ccc32)c1] | [M + H]⁺ = 546.1 |
| 81 | 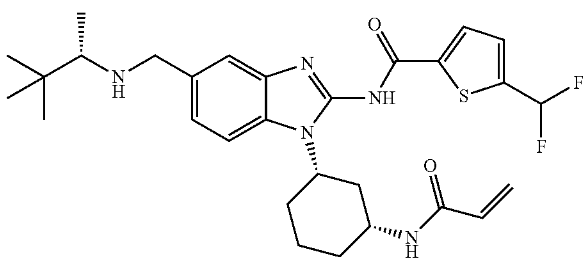 [SMILES: C=CC(=O)N[C@@H]1CCC[C@H](n2c(NC(=O)c3ccc(C(F)F)s3)nc3cc(CN[C@@H](C)C(C)(C)C)ccc32)C1] | [M + H]⁺ = 558.3 |
| 82 | 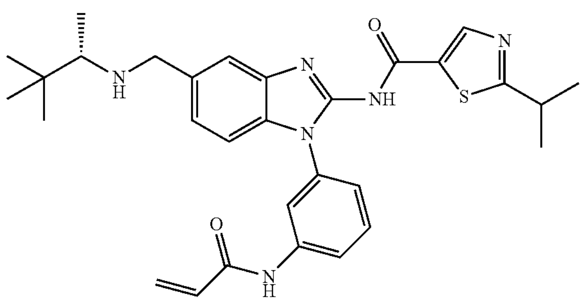 [SMILES: C=CC(=O)Nc1cccc(-n2c(NC(=O)c3cnc(C(C)C)s3)nc3cc(CN[C@@H](C)C(C)(C)C)ccc32)c1] | [M + H]⁺ = 545.3 |
| 83 | 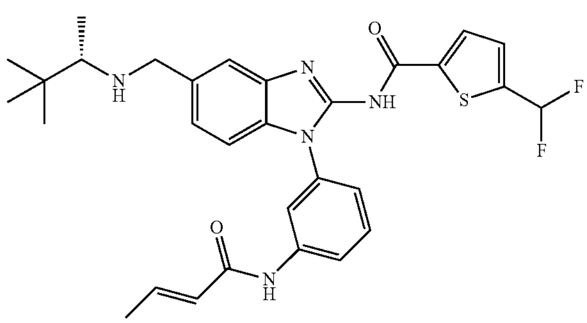 [SMILES: C/C=C/C(=O)Nc1cccc(-n2c(NC(=O)c3ccc(C(F)F)s3)nc3cc(CN[C@@H](C)C(C)(C)C)ccc32)c1] | [M + H]⁺ = 566.2 |

TABLE 1-continued

Example Compounds of Formula I

| Compound | Structure | MS (m/z) |
|---|---|---|
| 84 | 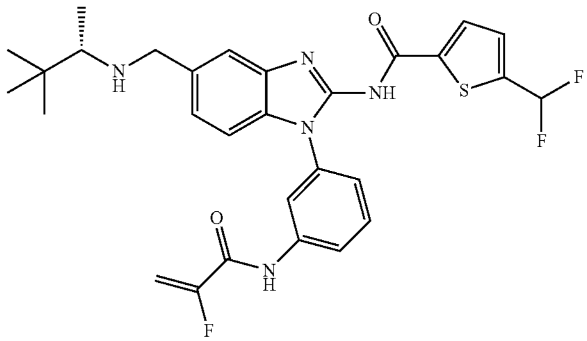 [SMILES: C=C(F)C(=O)Nc1cccc(-n2c(NC(=O)c3ccc(C(F)F)s3)nc3cc(CN[C@@H](C)C(C)(C)C)ccc32)c1] | [M + H]⁺ = 570.2 |
| 85 | 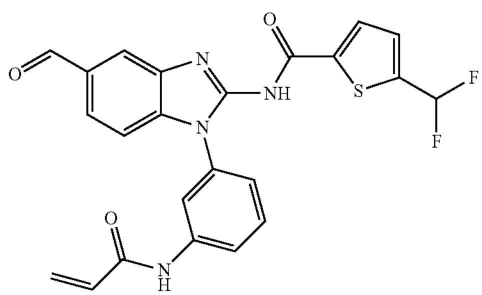 [SMILES: C=CC(=O)Nc1cccc(-n2c(NC(=O)c3ccc(C(F)F)s3)nc3cc(C=O)ccc32)c1] | [M + H]⁺ = 467.1 |
| 86 | 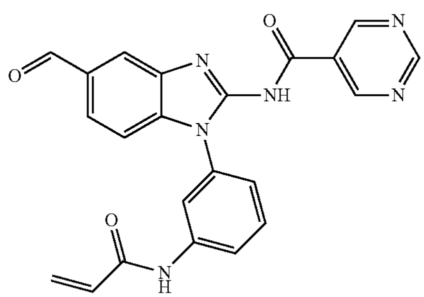 [SMILES: C=CC(=O)Nc1cccc(-n2c(NC(=O)c3cncnc3)nc3cc(C=O)ccc32)c1] | [M + H]⁺ = 413.4 |
| 87 | 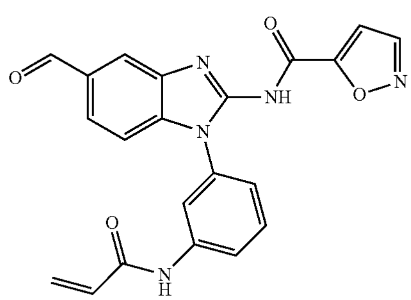 [SMILES: C=CC(=O)Nc1cccc(-n2c(NC(=O)c3ccno3)nc3cc(C=O)ccc32)c1] | [M + H]⁺ = 402.4 |
| 88 | 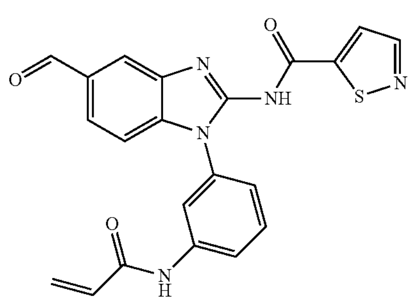 | [M + H]⁺ = 418.4 |

The compounds in the table above form part of the invention in addition to pharmaceutically acceptable salts thereof.

Some of the above compounds have one or more chiral centres, for example one or two chiral centres. All enantiomers and diastereomers of the above compounds are contemplated by the invention. In one embodiment the compounds of the invention have the (R)-configuration at the stereocentre. In an alternative embodiment the compounds of the invention have the (S)-configuration at the stereocentre. Where compounds have two stereocentres the stereocentres may have (R),(R) configuration, (S),(R) configuration, (R),(S) configuration or (S),(S) configuration. The invention also contemplates racemic mixtures of these compounds.

Assays for determining kinase activity are described in more detail in the accompanying examples.

Example 2: CD3/CD28 Mediated PBMC Proliferation Assay

Inhibition of cellular ITK was assessed by measuring proliferation of PBMCs following stimulation with anti-CD3 and anti-CD28 antibodies. Individual wells of 96 well tissue culture plates were coated with 50 μL of 5 μg/mL anti-CD3 (OKT3, eBiosciences) for 2 hours at 37° C. Human PBMCs (Stemcell Technologies catalog #70025.3) were plated in 96-well plates at a final concentration of 9.2×10e5 cells/mL in complete media (RPMI, 10% heat inactivated FBS, 55 uM β-mercaptoethanol) and pre-treated with compound curves for 30 minutes at 37° C., 5% $CO_2$. Pre-treated cells plus compounds were transferred to washed anti-CD3 coated plates. Soluble anti-CD28 (CD28.2 eBiosciences) was added to each well at a final concentration of 2 μg/mL. The cells were placed in a humidified 37° C. incubator with 5% $CO_2$ for 72 hours and metabolic viability was measured by quantification of ATP levels with Cell Titer-Glo (Promega catalog # G9242). Controls included unstimulated cells and vehicle alone. EC50 values (50% proliferation in the presence of compound as compared to vehicle treated controls) were calculated from dose response compound curves using GraphPad Prism Software.

TABLE 2

| Results | |
|---|---|
| Compound | $EC_{50}$ (nM) |
| 1 | b |
| 2 | b |
| 3 | c |
| 4 | c |
| 5 | b |
| 6 | b |
| 7 | b |
| 8 | c |
| 9 | b |
| 10 | b |
| 11 | b |
| 12 | c |
| 13 | b |
| 14 | b |
| 15 | b |
| 16 | b |
| 17 | b |
| 18 | b |
| 19 | b |
| 20 | c |
| 21 | a |
| 22 | a |
| 23 | a |
| 24 | c |
| 25 | a |
| 26 | c |
| 27 | c |
| 28 | b |
| 29 | a |
| 30 | a |
| 31 | a |
| 32 | a |
| 33 | a |
| 34 | c |
| 35 | a |
| 36 | b |
| 37 | c |
| 38 | b |
| 39 | a |
| 40 | a |
| 41 | b |
| 42 | b |
| 43 | a |
| 44 | a |
| 45 | a |
| 46 | b |
| 47 | a |
| 48 | b |
| 49 | c |
| 50 | a |
| 51 | a |
| 52 | a |
| 53 | b |
| 54 | c |
| 55 | c |
| 56 | b |
| 57 | b |
| 58 | c |
| 59 | a |
| 60 | a |
| 61 | a |
| 62 | c |
| 63 | c |
| 64 | c |
| 65 | c |
| 66 | b |
| 67 | c |
| 68 | a |
| 69 | b |
| 70 | c |
| 71 | b |
| 72 | c |
| 73 | b |
| 74 | c |
| 75 | c |
| 76 | b |
| 77 | b |
| 78 | c |
| 79 | c |
| 80 | b |
| 81 | b |
| 83 | c |
| 84 | b | a-$EC_{50}$ < 10 nM;
b-10 nM < $EC_{50}$ < 100 nM,
c-$EC_{50}$ > 100 nM

Example 3: Jurkat IL-2 Release Assay

Inhibition of cellular ITK was assessed by measuring release of IL-2 following stimulation with anti-CD3 and anti-CD28 antibodies. Individual wells of 96 well tissue culture plates were coated with 50 μL of 10 μg/mL anti-CD3 (OKT3, eBiosciences) for 2 hours at 37° C. Jurkat human acute T cell leukemia cells (ATCC) were plated in 96-well plates at a final concentration of 9.2×10e5 cells/mL in complete media (RPMI, 10% FBS, 1.5 g/L sodium bicarbonate, 10 mM Hepes, 1 mM sodium pyruvate, 4.5 g/L glucose) and pre-treated with compound curves for 30 minutes at 37° C., 5% $CO_2$. Pre-treated cells plus compounds were transferred to washed anti-CD3 coated plates. Soluble anti-CD28 (CD28.2 eBiosciences) was added to each well at a final concentration of 1 µg/mL. The cells were placed in a humidified 37° C. incubator with 5% $CO_2$ for 48 hours and IL-2 release was measured using a commercial ELISA (BD Bioscience catalog #555190). Controls included unstimulated cells and vehicle alone. EC50 values (50% IL-2 release in the presence of compound as compared to vehicle treated controls) were calculated from dose response compound curves using GraphPad Prism Software.

TABLE 4

Results

| Compound | $EC_{50}$ (nM) |
|---|---|
| 1 | b |
| 2 | a |
| 3 | b |
| 4 | b |
| 5 | a |
| 6 | a |
| 7 | b |
| 8 | b |
| 9 | b |
| 10 | b |
| 11 | c |
| 12 | c |
| 13 | b |
| 14 | a |
| 15 | b |
| 16 | b |
| 17 | b |
| 18 | a |
| 19 | a |
| 20 | b |
| 21 | b |
| 22 | a |
| 23 | a |
| 24 | c |
| 25 | a |
| 26 | b |
| 27 | c |
| 28 | a |
| 29 | a |
| 30 | b |
| 31 | a |
| 32 | a |
| 33 | a |
| 34 | c |
| 35 | b |
| 36 | b |
| 37 | c |
| 38 | a |
| 39 | b |
| 40 | b |
| 41 | a |
| 42 | a |
| 43 | a |
| 50 | a |
| 54 | c |
| 57 | b |
| 59 | a |
| 62 | b |
| 67 | b |
| 72 | b |
| 73 | a |
| 76 | a |
| 77 | a |

TABLE 4-continued

Results

| Compound | $EC_{50}$ (nM) |
|---|---|
| 78 | b |
| 80 | b |
| 81 | a |
| 82 | b |
| 84 | b | a-$EC_{50}$ < 10 nM;
b-10 nM < $EC_{50}$ < 100 nM,
c-$EC_{50}$ > 100 nM

Example 4: ITK Kinase Inhibition Assay

The in vitro kinase assays were performed at Nanosyn utilizing micro-fluidic detection technology. The test compounds were serially pre-diluted in DMSO and added, by the acoustic dispensing (Labcyte® 550), directly to 384 well assay plates into 10 uL of a buffer with enzyme comprising: 100 mM HEPES, pH7.5, 5 mM $MgCl_2$, 0.1% bovine serum albumin, 1 mM DTT, 0.01% Triton X-100 and the enzyme. Final DMSO concentration was maintained at 1% in all samples, including the controls. The reactions were initiated by addition of ATP (to the specified concentration) and the fluorescently labeled peptide substrate to a final concentration of 1 uM, and incubated for 3 hours at 25° C. Following incubation, the reactions were quenched by addition of 40 µL of termination buffer (100 mM HEPES, pH7.5, 0.01% Triton X-100, 50 mM EDTA). Terminated plates were analyzed using Caliper LabChip® 3000 microfluidic electrophoresis instrument (Caliper Life Sciences/Perkin Elmer). The enzymatic modification of the peptide substrate (phosphorylation) results in a change of net charge enabling electrophoretic separation of product from substrate. As substrate and product are separated by electrophoresis, two peaks of fluorescence are observed. Change in the relative fluorescence intensity of the substrate and product peaks was the parameter measured, reflecting enzyme activity. In the presence of inhibitor, the ratio between product and substrate is altered: signal of the product decreases, while the signal of the substrate increases. Activity in each test sample was determined as the product to sum ratio (PSR):P/(S+P), where P is the peak height of the product and S is the peak height of the FAM-cAMP substrate. For each compound, enzyme activity was measured at 12 concentrations spaced by 3× dilution intervals. Negative control samples (0%-inhibition in the absence of inhibitor, DMSO only) and positive control samples (100%-inhibition, in the absence of enzyme or in the presence of control inhibitor) were assembled in replicates of four and were used to calculate %-inhibition values in the presence of compounds. Percent inhibition ($P_{inh}$) was determined using the following equation: $P_{inh}=(PSR_{0\%}-PSR_{inh})/(PSR_{0\%}-PSR_{100\%})*100$, where $PSR_{inh}$ is the product sum ratio in the presence of inhibitor, $PSR_{0\%}$ is the product sum ratio in the absence of inhibitor and $PSR_{100\%}$ is the product sum ratio in 100%-inhibition control samples. To determine $IC_{50}$ values, the inhibition curves ($P_{inh}$ versus inhibitor concentration) were fitted by 4 parameter sigmoid dose-response model using XLfit software (IDBS).

TABLE 5

Results of ITK kinase inhibition

| Compound | $EC_{50}$ (nM) |
|---|---|
| 1 | a |
| 2 | a |
| 3 | b |
| 9 | a |
| 11 | a |
| 12 | c |
| 16 | a |
| 17 | b |
| 18 | a |
| 19 | a |
| 25 | a |
| 27 | c |
| 28 | a |
| 31 | a |
| 38 | a |
| 42 | b |
| 43 | a |
| 50 | a |
| 62 | a |
| 68 | a |
| 77 | a |
| 81 | a | a-$EC_{50}$ < 10 nM;
b-10 nM < $EC_{50}$ < 100 nM,
c-$EC_{50}$ > 100 nM

Example 5: RLK/TXK Kinase Inhibition Assay

The in vitro kinase assays were performed at Nanosyn utilizing micro-fluidic detection technology. The test compounds were serially pre-diluted in DMSO and added, by the acoustic dispensing (Labcyte® 550), directly to 384well assay plates into 10 uL of a buffer with enzyme comprising: 100 mM HEPES, pH7.5, 5 mM $MgCl_2$, 0.1% bovine serum albumin, 1 mM DTT, 0.01% Triton X-100 and the enzyme. Final DMSO concentration was maintained at 1% in all samples, including the controls. The reactions were initiated by addition of ATP (to the specified concentration) and the fluorescently labeled peptide substrate to a final concentration of 1 uM, and incubated for 3 hours at 25° C. Following incubation, the reactions were quenched by addition of 40 μL of termination buffer (100 mM HEPES, pH7.5, 0.01% Triton X-100, 50 mM EDTA). Terminated plates were analyzed using Caliper LabChip® 3000 microfluidic electrophoresis instrument (Caliper Life Sciences/Perkin Elmer). The enzymatic modification of the peptide substrate (phosphorylation) results in a change of net charge enabling electrophoretic separation of product from substrate. As substrate and product are separated by electrophoresis, two peaks of fluorescence are observed. Change in the relative fluorescence intensity of the substrate and product peaks was the parameter measured, reflecting enzyme activity. In the presence of inhibitor, the ratio between product and substrate is altered: signal of the product decreases, while the signal of the substrate increases. Activity in each test sample was determined as the product to sum ratio (PSR): P/(S+P), where P is the peak height of the product and S is the peak height of the FAM-cAMP substrate. For each compound, enzyme activity was measured at 12 concentrations spaced by 3× dilution intervals. Negative control samples (0%-inhibition in the absence of inhibitor, DMSO only) and positive control samples (100%-inhibition, in the absence of enzyme or in the presence of control inhibitor) were assembled in replicates of four and were used to calculate %-inhibition values in the presence of compounds. Percent inhibition ($P_{inh}$) was determined using the following equation: $P_{inh}=(PSR_{0\%}-PSR_{inh})/(PSR_{0\%}-PSR_{100\%})*100$, where $PSR_{inh}$ is the product sum ratio in the presence of inhibitor, $PSR_{0\%}$ is the product sum ratio in the absence of inhibitor and $PSR_{100\%}$ is the product sum ratio in 100%-inhibition control samples. To determine $IC_{50}$ values, the inhibition curves ($P_{inh}$ versus inhibitor concentration) were fitted by 4 parameter sigmoid dose-response model using XLfit software (IDBS).

TABLE 6

Results of RLK/TXK kinase inhibition

| Compound | $EC_{50}$ (nM) |
|---|---|
| 1 | b |
| 2 | a |
| 3 | b |
| 9 | a |
| 11 | a |
| 12 | b |
| 16 | a |
| 17 | a |
| 18 | a |
| 19 | b |
| 25 | a |
| 27 | c |
| 28 | a |
| 31 | a |
| 38 | a |
| 42 | b |
| 43 | a |
| 50 | a |
| 62 | b |
| 68 | a |
| 77 | a |
| 81 | b | a-$EC_{50}$ < 10 nM;
b-10 nM < $EC_{50}$ < 100 nM,
c-$EC_{50}$ > 100 nM

Example 6: Tec Kinase Inhibition Assay

The in vitro kinase assays were performed at Nanosyn utilizing micro-fluidic detection technology. The test compounds were serially pre-diluted in DMSO and added, by the acoustic dispensing (Labcyte® 550), directly to 384well assay plates into 10 uL of a buffer with enzyme comprising: 100 mM HEPES, pH7.5, 5 mM $MgCl_2$, 0.1% bovine serum albumin, 1 mM DTT, 0.01% Triton X-100 and the enzyme. Final DMSO concentration was maintained at 1% in all samples, including the controls. The reactions were initiated by addition of ATP (to the specified concentration) and the fluorescently labeled peptide substrate to a final concentration of 1 uM, and incubated for 3 hours at 25° C. Following incubation, the reactions were quenched by addition of 40 μL of termination buffer (100 mM HEPES, pH7.5, 0.01% Triton X-100, 50 mM EDTA). Terminated plates were analyzed using Caliper LabChip® 3000 microfluidic electrophoresis instrument (Caliper Life Sciences/Perkin Elmer). The enzymatic modification of the peptide substrate (phosphorylation) results in a change of net charge enabling electrophoretic separation of product from substrate. As substrate and product are separated by electrophoresis, two peaks of fluorescence are observed. Change in the relative fluorescence intensity of the substrate and product peaks was the parameter measured, reflecting enzyme activity. In the presence of inhibitor, the ratio between product and substrate is altered: signal of the product decreases, while the signal of the substrate increases. Activity in each test sample was determined as the product to sum ratio (PSR): P/(S+P), where P is the peak height of the product and S is the peak height of the FAM-cAMP substrate. For each compound, enzyme activity was measured at 12 concentrations spaced by 3× dilution intervals. Negative control samples (0%-inhibition in the absence of inhibitor, DMSO only) and positive control samples (100%-inhibition, in the absence of enzyme or in the presence of control inhibitor) were assembled in replicates of four and were used to calculate %-inhibition values in the presence of compounds. Percent inhibition ($P_{inh}$) was determined using the following equation: $P_{inh}=(PSR_{0\%}-PSR_{inh})/(PSR_{0\%}-PSR_{100\%})*100$, where $PSR_{inh}$ is the product sum ratio in the presence of inhibitor, $PSR_{0\%}$ is the product sum ratio in the absence of inhibitor and $PSR_{100\%}$ is the product sum ratio in 100%-inhibition control samples. To determine $IC_{50}$ values, the inhibition curves ($P_{inh}$ versus inhibitor concentration) were fitted by 4 parameter sigmoid dose-response model using XLfit software (IDBS).

TABLE 7

Results of Tec kinase inhibition

| Compound | $EC_{50}$ (nM) |
|---|---|
| 2 | b |
| 9 | b |
| 25 | a |
| 28 | b |
| 38 | b | a-$EC_{50}$ < 10 nM;
b-10 nM < $EC_{50}$ < 100 nM,
c-$EC_{50}$ > 100 nM

The invention claimed is:

1. A compound of Formula I:

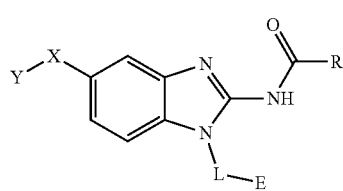

Formula I or pharmaceutically acceptable salt, stereoisomer, tautomer, isotope, prodrug, or complex thereof, wherein R is substituted or unsubstituted thiophenyl;

L is

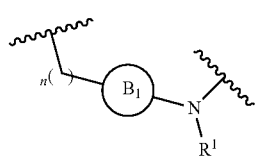

wherein
ring $B_1$ is substituted or unsubstituted cycloalkyl

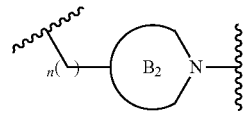

$R^1$ is hydrogen, lower alkyl or lower cycloalkyl; and
n is 0 or 1;
E is:

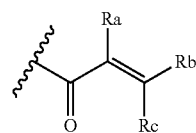

wherein
Ra, Rb and Rc are independently hydrogen, halogen, —CN, substituted or unsubstituted alkyl, substituted or unsubstituted heteroalkyl, substituted or unsubstituted cycloalkyl, or substituted or unsubstituted heterocyclyl; or
Ra and Rb taken together with the carbon atoms to which they are attached form a 3- to 8-membered substituted or unsubstituted cycloalkyl ring or form a 3- to 8-membered substituted or unsubstituted heterocyclic ring and Rc is selected as above; or
Rb and Rc taken together with the carbon atom to which they are attached form a 3- to 8-membered substituted or unsubstituted cycloalkyl ring or form a 3- to 8-substituted or unsubstituted membered heterocyclic ring and Ra is selected as above; or
Ra and Rb taken together with the carbon atoms to which they are attached form a triple bond and Rc is selected as above;
wherein L-E is:

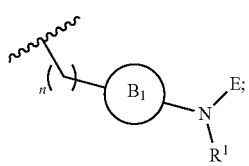

X is alkylene, -(alkylene)-$NR^2$—, -(alkylene)-$NR^3$—, -(alkylene)-O—, —O—, —S—, —S(O)$_m$—, —$NR^2$—, —$NR^3$—, —C(O)—, —C(O)O—, —C(O)$NR^2$—, —C(O)O$NR^2$—, or —S(O)$_m NR^2$—, wherein
$R^2$ is hydrogen, lower alkyl or lower cycloalkyl;
$R^3$ is —C(O)$R^4$, —C(O)O$R^4$ or —S(O)$_m R^4$;
$R^4$ is lower alkyl or lower cycloalkyl;
m is 1 or 2; or
X is a bond; and
Y is hydrogen, halogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocyclyl, substituted or unsubstituted aryl, substituted or unsubstituted heteroaryl, substituted or unsubstituted aralkyl, or substituted or unsubstituted heteroaralkyl.

2. The compound according to claim 1, wherein R is

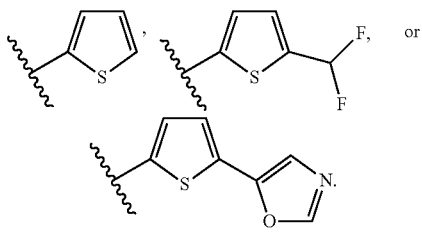

3. The compound according to claim 1, wherein

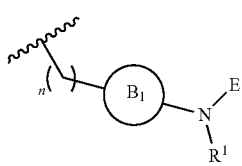

$R^1$ is hydrogen or methyl;
n is 0;
E is:

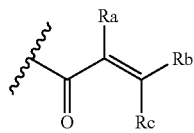

wherein
  Ra, Rb and Rc are independently hydrogen, halogen, —CN, or $C_1$ to $C_3$ substituted or unsubstituted alkyl, substituted or unsubstituted heteroalkyl, or substituted or unsubstituted cycloalkyl

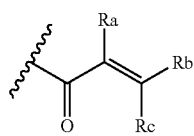

4. The compound according to claim 3, wherein L-E is

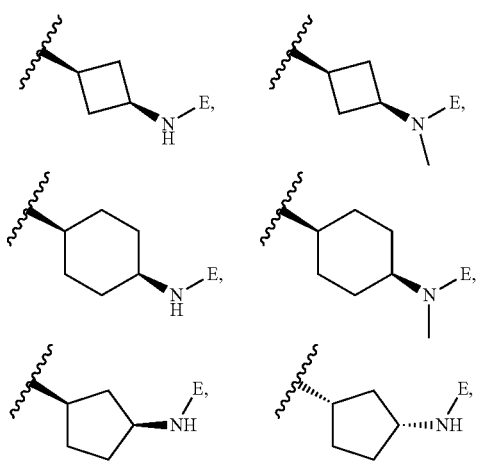

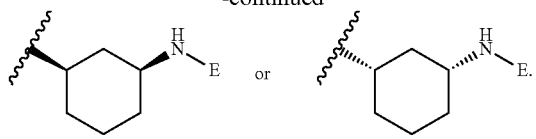

5. The compound according to claim 1, wherein E is

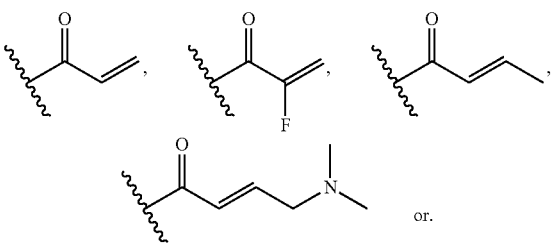

6. The compound according to claim 1, wherein X—Y is:
(a) —CH$_2$—NH—Y, where
Y is selected from the group consisting of hydrogen, halogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocyclyl, substituted or unsubstituted aryl, substituted or unsubstituted heteroaryl, substituted or unsubstituted aralkyl, and substituted or unsubstituted heteroaralkyl; or
(b) —CH$_2$—NR$^2$—Y, where
$R^2$ is hydrogen, lower alkyl or lower cycloalkyl, and;
Y is selected from the group consisting of hydrogen, halogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocyclyl, substituted or unsubstituted aryl, substituted or unsubstituted heteroaryl, substituted or unsubstituted aralkyl, and substituted or unsubstituted heteroaralkyl; or
(c) —C(O)—NR$^2$—Y, where
$R^2$ is hydrogen, lower alkyl or lower cycloalkyl, and
Y is selected from the group consisting of: hydrogen, halogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocyclyl, substituted or unsubstituted aryl, substituted or unsubstituted heteroaryl, substituted or unsubstituted aralkyl, and substituted or unsubstituted heteroaralkyl; or
(d) —NR$^2$C(O)—Y, where
$R^2$ is hydrogen, lower alkyl or lower cycloalkyl and;
Y is selected from the group consisting of: hydrogen, halogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocyclyl, substituted or unsubstituted aryl, substituted or unsubstituted heteroaryl, substituted or unsubstituted aralkyl, and substituted or unsubstituted heteroaralkyl; or (e) —NR²SO₂—Y, where
R² is hydrogen, lower alkyl or lower cycloalkyl, and
Y is selected from the group consisting of: hydrogen, halogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocyclyl, substituted or unsubstituted aryl, substituted or unsubstituted heteroaryl, substituted or unsubstituted aralkyl, and substituted or unsubstituted heteroaralkyl; or (f) —O—CH₂—Y, where
Y is selected from the group consisting of: hydrogen, halogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocyclyl, substituted or unsubstituted aryl, substituted or unsubstituted heteroaryl, substituted or unsubstituted aralkyl, and substituted or unsubstituted heteroaralkyl; or (g) —CH₂—NR³—Y, where
R³ is —C(O)R⁴, —C(O)OR⁴ or —S(O)ₘR⁴, wherein m is an integer from 1 to 2;
R⁴ is lower alkyl or lower cycloalkyl; and
Y is selected from the group consisting of: hydrogen, halogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocyclyl, substituted or unsubstituted aryl, substituted or unsubstituted heteroaryl, substituted or unsubstituted aralkyl, and substituted or unsubstituted heteroaralkyl; or (h) —CH₂—Y where
Y is selected from the group consisting of: hydrogen, halogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocyclyl, substituted or unsubstituted aryl, substituted or unsubstituted heteroaryl, substituted or unsubstituted aralkyl, and substituted or unsubstituted heteroaralkyl.

7. A compound of Formula IIa:

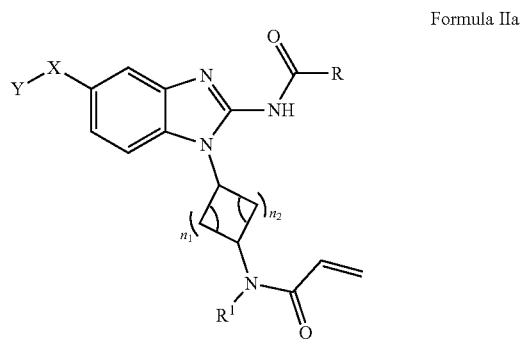

Formula IIa or pharmaceutically acceptable salt, stereoisomer, tautomer, isotope, prodrug, or complex thereof, wherein
R is substituted or unsubstituted thiophenyl;
X-Y is selected —CH₂—NH—Y, —CH₂—NR²—Y, —CH₂—NR³—Y, —NR²C(O)—Y, —C(O)NR²—Y, or and —CH₂—Y;
wherein
R² is hydrogen, lower alkyl or lower cycloalkyl;
R³ is —C(O)R⁴, —C(O)OR⁴ or —S(O)ₘR⁴, wherein m is 1 or 2;
R⁴ is lower alkyl or lower cycloalkyl;
Y is hydrogen, halogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocyclyl, substituted or unsubstituted aryl, substituted or unsubstituted heteroaryl, substituted or unsubstituted aralkyl, or substituted or unsubstituted heteroaralkyl,
n₁ is 0, 1, 2 or 3;
n₂ is 1, 2 or 3; and
R¹ is hydrogen, lower alkyl or lower cycloalkyl.

8. A compound having one of the following structures:

| Compound | Structure |
|---|---|
| 1 | 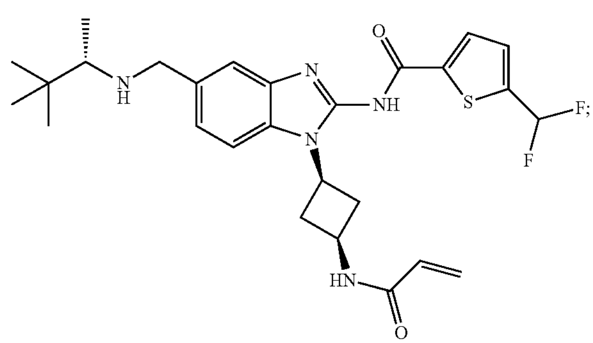 [SMILES: C=CC(=O)N[C@H]1C[C@@H](n2c(NC(=O)c3ccc(C(F)F)s3)nc3cc(CN[C@@H](C)C(C)(C)C)ccc32)C1] |

-continued
| Compound | Structure |
|---|---|
| 3 | 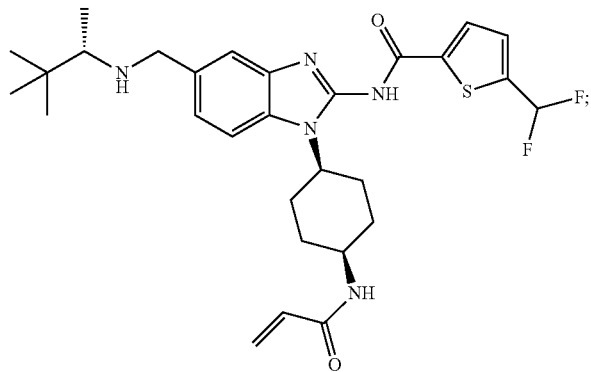 [SMILES: C=CC(=O)N[C@H]1CC[C@@H](n2c(NC(=O)c3ccc(C(F)F)s3)nc3cc(CN[C@@H](C)C(C)(C)C)ccc32)CC1] |
| 6 | 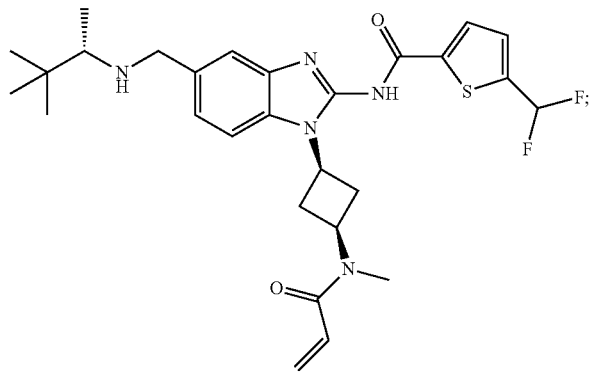 [SMILES: C=CC(=O)N(C)[C@H]1C[C@@H](n2c(NC(=O)c3ccc(C(F)F)s3)nc3cc(CN[C@@H](C)C(C)(C)C)ccc32)C1] |
| 18 | 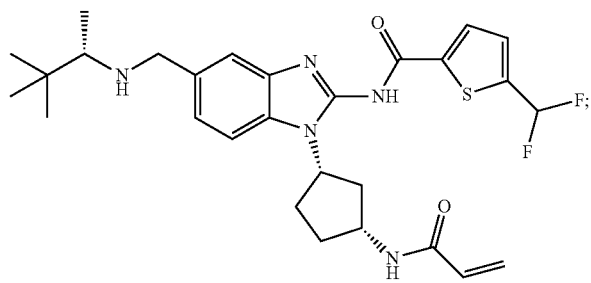 [SMILES: C=CC(=O)N[C@@H]1CC[C@H](n2c(NC(=O)c3ccc(C(F)F)s3)nc3cc(CN[C@@H](C)C(C)(C)C)ccc32)C1] |
| 58 | 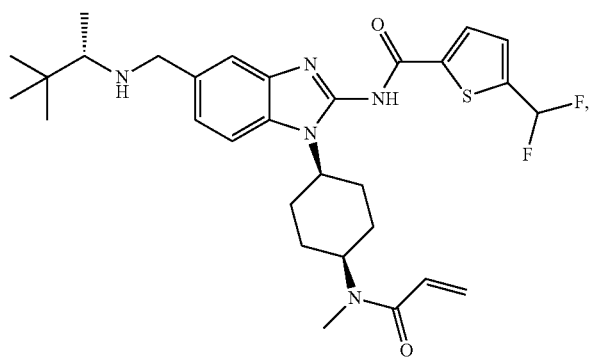 [SMILES: C=CC(=O)N(C)[C@H]1CC[C@@H](n2c(NC(=O)c3ccc(C(F)F)s3)nc3cc(CN[C@@H](C)C(C)(C)C)ccc32)CC1] |

| Compound | Structure |
|---|---|
| 62 | 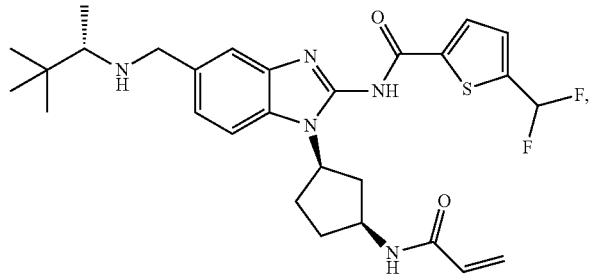 [SMILES: C=CC(=O)N[C@H]1CC[C@@H](n2c(NC(=O)c3ccc(C(F)F)s3)nc3cc(CN[C@@H](C)C(C)(C)C)ccc32)C1] |
| 63 | 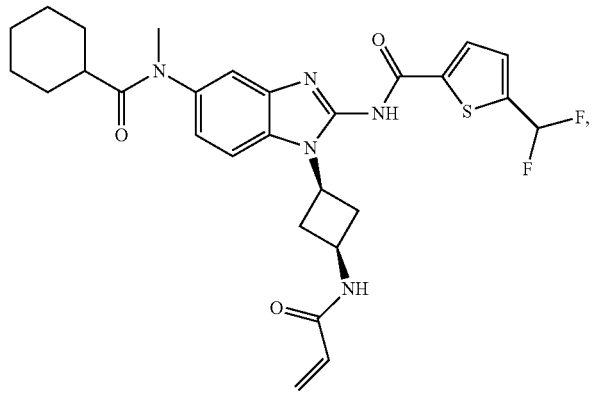 [SMILES: C=CC(=O)N[C@H]1C[C@@H](n2c(NC(=O)c3ccc(C(F)F)s3)nc3cc(N(C)C(=O)C4CCCCC4)ccc32)C1] |
| 64 | 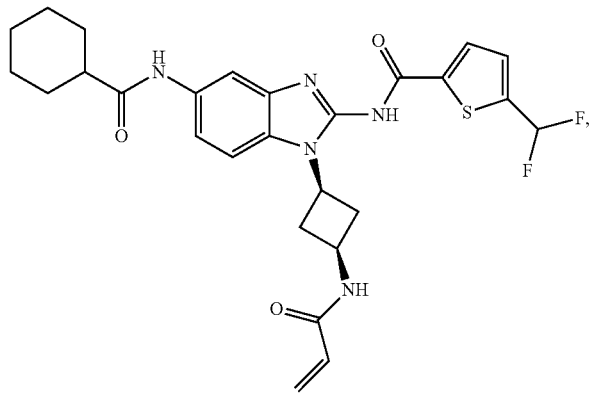 [SMILES: C=CC(=O)N[C@H]1C[C@@H](n2c(NC(=O)c3ccc(C(F)F)s3)nc3cc(NC(=O)C4CCCCC4)ccc32)C1] |
| 65 | 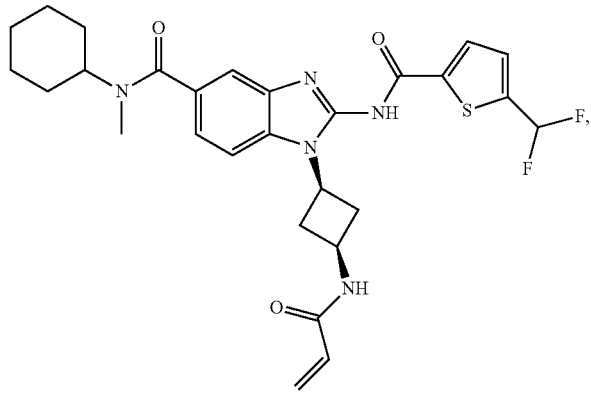 [SMILES: C=CC(=O)N[C@H]1C[C@@H](n2c(NC(=O)c3ccc(C(F)F)s3)nc3cc(C(=O)N(C)C4CCCCC4)ccc32)C1] |

-continued

| Compound | Structure |
|---|---|
| 68 | 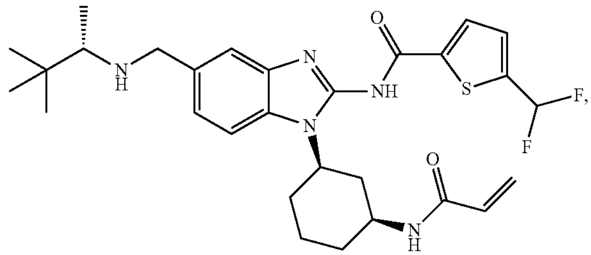 [SMILES: C=CC(=O)N[C@H]1CCC[C@@H](n2c(NC(=O)c3ccc(C(F)F)s3)nc3cc(CN[C@@H](C)C(C)(C)C)ccc32)C1] |
| 70 | 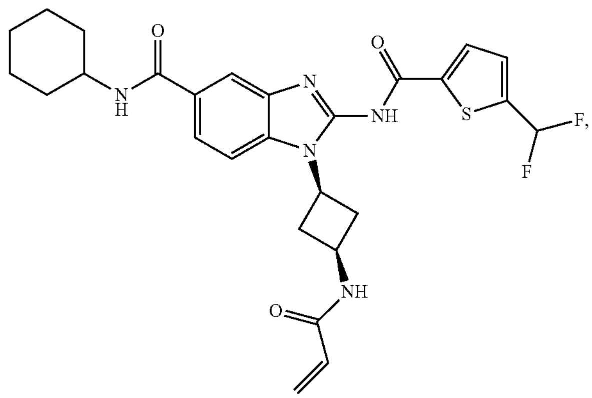 [SMILES: C=CC(=O)N[C@H]1C[C@@H](n2c(NC(=O)c3ccc(C(F)F)s3)nc3cc(C(=O)NC4CCCCC4)ccc32)C1] |
| 71 | 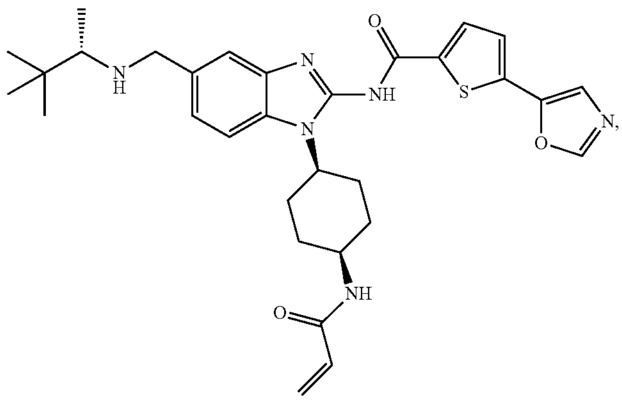 [SMILES: C=CC(=O)N[C@H]1CC[C@@H](n2c(NC(=O)c3ccc(-c4cnco4)s3)nc3cc(CN[C@@H](C)C(C)(C)C)ccc32)CC1] |
| 81 | | or a pharmaceutically acceptable salt, stereoisomer, tautomer, isotope, prodrug, or complex thereof.

9. A pharmaceutical composition comprising the compound of any one of claim 1, 2, 3, 4, 5, 6, 7, or 8, or a pharmaceutically acceptable salt, solvate, solvates of a salt, stereoisomer, tautomer, isotope, prodrug, or complex thereof in combination with at least one pharmaceutically acceptable carrier.

10. A probe comprising the compound of claim 1 covalently conjugated to a detectable label or affinity tag for said compound, wherein the detectable label is optionally selected from the group consisting of: a fluorescent moiety, a chemiluminescent moiety, a paramagnetic contrast agent, a metal chelate, a radioactive isotope-containing moiety and biotin.

* * * * *